United States Patent
Shi et al.

(10) Patent No.: US 11,345,665 B2
(45) Date of Patent: May 31, 2022

(54) CHIRAL 1,3-DIARYLIMIDAZOLIUM SALT CARBENE PRECURSOR, SYNTHESIS METHOD THEREFOR, METAL SALT COMPOUND AND APPLICATION THEREOF

(71) Applicant: SHANGHAI INSTITUTE OF ORGANIC CHEMISTRY, CHINESE ACADEMY OF SCIENCES, Shanghai (CN)

(72) Inventors: Shiliang Shi, Shanghai (CN); Yuan Cai, Shanghai (CN); Xintuo Yang, Shanghai (CN); Feng Li, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/764,303

(22) PCT Filed: Nov. 15, 2018

(86) PCT No.: PCT/CN2018/115661
§ 371 (c)(1),
(2) Date: May 14, 2020

(87) PCT Pub. No.: WO2019/096209
PCT Pub. Date: May 23, 2019

(65) Prior Publication Data
US 2020/0369620 A1   Nov. 26, 2020

(30) Foreign Application Priority Data

Nov. 15, 2017   (CN) .......................... 201711132279.9

(51) Int. Cl.
| | | |
|---|---|---|
| *C07D 233/60* | (2006.01) | |
| *B01J 31/22* | (2006.01) | |
| *C07D 233/58* | (2006.01) | |
| *C07D 235/02* | (2006.01) | |
| *C07D 239/06* | (2006.01) | |
| *C07F 5/04* | (2006.01) | |

(52) U.S. Cl.
CPC ........ *C07D 233/60* (2013.01); *B01J 31/2295* (2013.01); *C07D 233/58* (2013.01); *C07D 235/02* (2013.01); *C07D 239/06* (2013.01); *C07F 5/04* (2013.01); *C07B 2200/13* (2013.01)

(58) Field of Classification Search
None
See application file for complete search history.

(56) References Cited

PUBLICATIONS

Arduengo, A. J.; Harlow, R. L.; Kline, M., "A Stable Crystalline Carbene," J. Am. Chem. Soc. 1991, 113, 361.

Hahn, F. E.; Jahnke, M. C., "Heterocyclic Carbenes: Synthesis and Coordination Chemistry," Angew. Chem. Int. Ed. 2008, 47, 3122.
Kühl. O., "The chemistry of functionalised N-heterocyclic carbenes," Chem. Soc. Rev. 2007. 36. 592.
Guillen, F.; Winn, C. L.; Alexakis, A., "Enantioselective copper-catalyzed conjugate addition using chiral diaminocarbene ligands," Tetrahedron: Asymmetry. 2001, 12, 2083.
Yoshida, K.; Kamimura, T.; Kuwabara, H.; Yanagisawa, A., "Chiral bicyclic NHC/Ir complexes for catalytic asymmetric transfer hydrogenation of ketones," Chem. Commun. 2015, 51, 15442.
Kim, J. H.; Greßies, S.; Boultadakis-Arapinis, M.; Daniliuc, C.; Glorius, F., "Rh(I)NHC*-Catalyzed Site- and Enantioselective Functionalization of C(sp3)-H Bonds Toward Chiral Triarylmethanes," ACS Catal. 2016, 6, 7652.
Hartung, J.; Doman, P. K.; Grubbs, R. H., "Enantioselective Olefin Metathesis with Cyclometalated Ruthenium Complexes," J. Am. Chem. Soc. 2014, 136, 13029.
Brown, H. C.; Zweifel, G., "The Hydroboration of Cyclic and Bicyclic Olefins—Stereochemistry of the Hydroboration Reaction," J. Am. Chem. Soc. 1961, 83, 2544.
Smith, J. R.; Collins, B. S. L.; Hesse, M. J.; Graham, M. A.; Myers, E. L.; Aggarwal, V. K., "Enantioselective Rhodium (III)-Catalyzed Markovnikov Hydroboration of Unactivated Terminal Alkenes," J. Am. Chem. Soc. 2017,139, 9148.
Cai, Y. et al. "Copper-Catalyzed Enantioselective Markovnikov Protoboration of a-Olefins Enabled by a Buttressed N-Heterocyclic Carbene Ligand," Angew. Chem. Int. Ed., vol. 57, No. (5), (Dec. 12, 2017), ISSN: 1433-7851, 1376-1380.

(Continued)

*Primary Examiner* — Samantha L Shterengarts
(74) *Attorney, Agent, or Firm* — Ice Miller LLP

(57) ABSTRACT

Chiral 1, 3-diarylimidazole salt carbene precursors, their methods of preparation, particularly transition metal complexes and their use in chemical synthesis are provided. In particular, an air and moisture stable chiral 1, 3-diarylimidazole carbene precursor Cu (I) complex has been prepared and applied to highly regio- and enantioselective Markovnikov hydroboration of unactivated terminal alkenes to form chiral boronic esters. Moreover, these new chiral NHCs can be potentially applied in various metal-catalyzed asymmetric transformations.

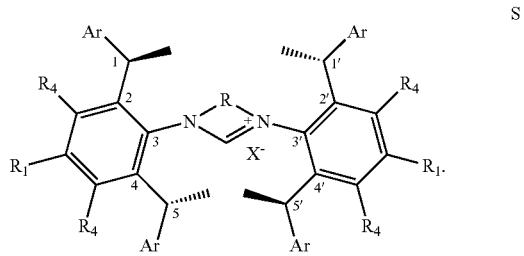

16 Claims, 1 Drawing Sheet

(56) References Cited

PUBLICATIONS

Diesel, J. et al. "Nickel-Catalyzed Enantioselective Pyridone C—H Functionalizations Enabled by a Bulky N-Heterocyclic Carbene Ligand," J. Am. Chem. Soc., vol. 14 No. (13), (Mar. 15, 2018), ISSN: 0002-7863, 4489-4493.
Kerchner, H. A. et al. "Synthesis of Secondary and Tertiary Alkylboranes via Formal Hydroboration of Terminal and 1,1-Disubstituted Alkenes," Org. Lett., vol. 18, No. (21), (Oct. 27, 2016), ISSN: 1523-7060, 5760-5763.
Albright, A. et al., "Design and Synthesis of C2-Symmetric N-Heterocyclic Carbene Precursors and Metal Carbenoids," J. Org. Chem, vol. 76, No. (18), (Aug. 6, 2011), ISSN: 0022-3263, 7341-7351.
International Search Report dated Feb. 14, 2019, International Application No. PCT/CN2018/115661.

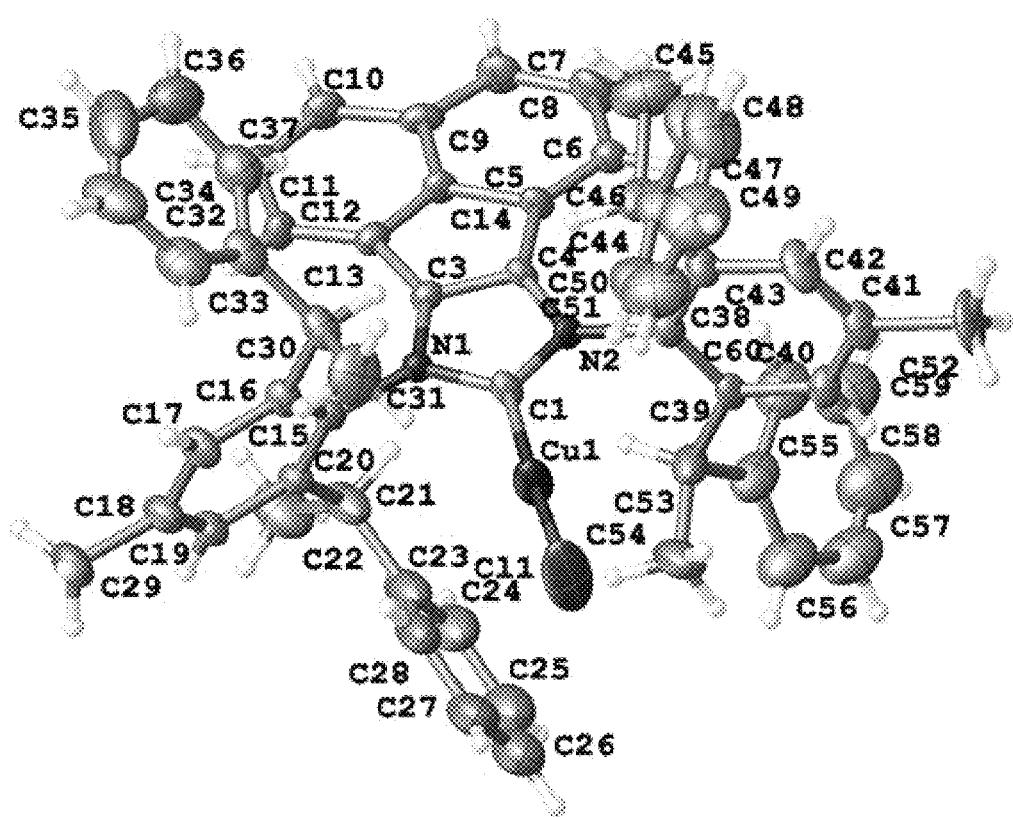

CHIRAL 1,3-DIARYLIMIDAZOLIUM SALT CARBENE PRECURSOR, SYNTHESIS METHOD THEREFOR, METAL SALT COMPOUND AND APPLICATION THEREOF

CROSS-REFERENCE TO RELATED APPLICATIONS

This application is a Section 371 of International Patent Application No. PCT/CN2018/115661, filed Nov. 15, 2018, which was published in the Chinese language on May 23, 2019, under International Publication No. WO 2019/096209 A1, which claims priority under 35 U.S.C. § 119(b) to Chinese Patent Application No. 201711132279.9, filed Nov. 15, 2017, the disclosure of all of which are incorporated herein by reference in their entireties.

FIELD OF THE INVENTION

The present invention relates chiral 1, 3-diarylimidazole salt carbene precursors, their methods of preparation, particularly transition metal complexes and their use in transition metal-catalyzed organic transformations.

BACKGROUND OF THE INVENTION

N-Heterocyclic Carbenes (NHCs) salts are very stable, easy to store, and widely used as ligands in transition metal-catalyzed organic transformations. Chiral NHCs are often used in asymmetric catalytic reactions due to their ease of synthesis, variable steric hindrance, and strong coordination ability to transition metals. See follows for the related reports: (a) Arduengo, A. J.; Harlow, R. L.; Kline, M. J. Am. Chem. Soc. 1991, 113, 361; (b) Hahn, F. E.; Jahnke, M. C. Angew. Chem. Int. Ed. 2008, 47, 3122; (c) Kuhl. O. Chem. Soc. Rev. 2007. 36. 592; (d) Guillen, F.; Winn, C. L.; Alexakis, A. Tetrahedron: Asymmetry. 2001, 12, 2083. In this publication, Alexakis reported NHC/Cu-catalyzed asymmetric Michael-Type Addition Reaction. [e] Yoshida, K.; Kamimura, T.; Kuwabara, H.; Yanagisawa, A. Chem. Commun. 2015, 51, 15442. In this publication, Yanagisawa reported NHC/Ir-catalyzed asymmetric hydrogenation to obtain chiral alcohols. [f] Kim, J. H.; Greßies, S.; Boultadakis-Arapinis, M.; Daniliuc, C.; Glorius, F. ACS Catal. 2016, 6, 7652. and [g] Hartung, J.; Donlan, P. K.; Grubbs, R. H. J. Am. Chem. Soc. 2014, 136, 13029. NHC/Metal-catalyzed asymmetric C—H activation has been reported by Glorius and Grubbs, respectively.

Organoboron are important synthetic intermediates. The hydroboration of alkenes is an important reaction to form organoboron. Hydroboration of alkenes often gives the anti-Markovnikov product, while the metal-catalyzed alkene hydroboration can produce Markovnikov products. However, asymmetric hydroboration of -olefins is a longstanding challenge. Aggarwal recently reported Rh-catalyzed asymmetric hydroboration of -olefins, but enantioselectivity (72-90% ee) leaves room for further improvement. See the following reports for details [(h) Brown, H. C.; Zweifel, G. J. Am. Chem. Soc. 1961, 83, 2544; (i) Kerchner, H. A.; Montgomery, J. Org. Lett. 2016, 18, 5760; (j) Smith, J. R.; Collins, B. S. L.; Hess; M. J.; Graham, M. A.; Myers, E. L.; Aggarwal, V. K. J. Am. Chem. Soc. 2017, 139, 9148].

Thus, the development of highly regio- and enantioselective Markovnikov hydroboration reactions of unactivated terminal olefins is highly desirable but remains challenging. The development of novel chiral NHCs for asymmetric hydroboration reactions and further application to various metal-catalyzed asymmetric reactions is currently an important research topic.

SUMMARY OF THE INVENTION

The present invention relates chiral 1, 3-diarylimidazole salt carbene precursors, their methods of preparation, particularly transition metal complexes and their use in chemical synthesis. An air and moisture stable chiral 1, 3-diarylimidazole carbene precursor Cu (I) complex has been prepared and applied to highly regio- and enantioselective Markovnikov hydroboration of unactivated terminal alkenes to form chiral boronic esters. Moreover, these new chiral NHCs can be potentially applied in various metal-catalyzed asymmetric transformations.

A chiral 1, 3-diaryl imidazole carbene precursor as shown in formula S:

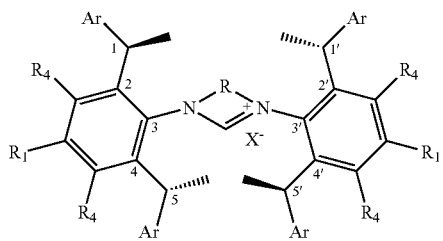

Wherein

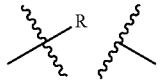

is selected from the group consisting of

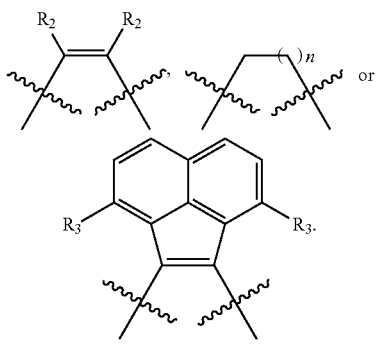

$R^1$ is independently selected from the group consisting of substituted or unsubstituted $C_{1-4}$alkyl, substituted or unsubstituted $C_{3-6}$ cycloalkyl, substituted or unsubstituted $C_{1-4}$alkoxy. In the substituted $C_{1-4}$alkyl, substituted $C_{3-6}$ cycloalkyl and substituted $C_{1-4}$alkoxy, said being optionally substituted means that one or more of the hydrogens on the group are optionally replaced with halo, cyano, nitro, carbonyl, $C_{1-4}$alkyl, halogen-substituted $C_{1-4}$alkyl, hydroxy-substituted $C_{1-4}$alkyl, $C_{1-4}$alkoxy, $C_{3-6}$ cycloalkyl, $C_{2-6}$ heterocyclic, $C_{6-14}$ aryl, $C_{2-10}$ heteroaryl, carboxyl or

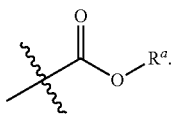

When there are multiple substituents, each substituent may be the same or different. $R^a$ represents $C_{1-4}$alkyl. The term "$C_{2-6}$ heterocyclic" as used herein means heterocyclic group containing from 2 to 6 carbon atoms, 1-4 atoms are a heteroatom selected from the group consisting of N, O and S. The term "$C_{2-10}$ heteroaryl" as used herein means heteroaryl group containing from 2 to 10 carbon atoms, 1-4 atoms are a heteroatom selected from the group consisting of N, O and S.

$R^2$ is independently selected from the group consisting of $C_{1-4}$alkyl, halo,

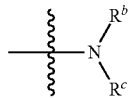

or $C_{6-14}$ aryl, when $R^b$ and $R^c$ are independently or simultaneously selected from the $C_{1-4}$alkyl.

$R^3$ and $R^4$ are independently or simultaneously selected from the group consisting of H or $C_{1-4}$alkyl.

Ar is independently selected from the group consisting of $C_{6-14}$ aryl or $C_{2-10}$ heteroaryl.

The term "$C_{2-10}$ heteroaryl" as used in Ar means heteroaryl group containing from 2 to 10 carbon atoms, 1-4 atoms are a heteroatom selected from the group consisting of N, O and S.

Wherein n is 1, 2 or 3.

X is $Cl^-$, $Br^-$, $I^-$, $OTf^-$ or $BF_4^-$.

In a preferred embodiment of the invention, one or more of the hydrogens on the Ar are further optionally replaced with halo, cyano, nitro, carbonyl, $C_{1-4}$alkyl, halogen-substituted $C_{1-4}$ alkyl, hydroxy-substituted $C_{1-4}$alkyl, $C_{1-4}$alkoxy, $C_{3-6}$ cycloalkyl, $C_{2-6}$ heterocyclic, $C_{6-14}$ aryl, $C_{2-10}$heteroaryl, carboxyl or

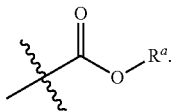

When there are multiple substituents, each substituent may be the same or different. $R^a$ represents $C_{1-4}$alkyl. The term "$C_{2-6}$ heterocyclic" as used herein means heterocyclic group containing from 2 to 6 carbon atoms, 1-4 atoms are a heteroatom selected from the group consisting of N, O and S. The term "$C_{2-10}$heteroaryl" as used herein means heteroaryl group containing from 2 to 10 carbon atoms, 1-4 atoms are a heteroatom selected from the group consisting of N, O and S.

In a preferred embodiment of the invention, one or more of the hydrogens on the Ar is further optionally replaced with $C_{1-4}$alkyl or $C_{1-4}$alkoxy.

In a preferred embodiment of the invention, each $R^1$, $R^2$, $R^3$ and Ar are the same.

In a preferred embodiment of the invention, Ar is independently selected from the $C_{6-14}$ aryl preferably, more preferably is phenyl.

In a preferred embodiment of the invention, $R^1$ is independently selected from the group consisting of $C_{1-4}$alkyl or $C_{1-4}$ alkoxy preferably, more preferably is methyl or methoxy.

In a preferred embodiment of the invention, $R^2$ and $R^3$ are independently or simultaneously selected from the group of $C_{1-4}$ alkyl preferably, more preferably is methyl.

In a preferred embodiment of the invention, $R^4$ is independently selected from the group consisting of H or methyl preferably.

In a preferred embodiment of the invention, n is for 2.

In a preferred embodiment of the invention, X is $Cl^-$, $Br^-$, $I^-$ or $BF_4^-$, wherein $Cl^-$ or $Br^-$ preferably.

In a preferred embodiment of the invention, each $R^1$ is independently selected from the group consisting of substituted $C_{1-4}$ alkyl, substituted $C_{3-6}$ cycloalkyl and substituted $C_{1-4}$ alkoxy, said latter 3 groups being optionally substituted with $C_{2-10}$heteroaryl, the term "$C_{2-10}$heteroaryl" as used herein means heteroaryl group containing from 3 to 10 carbon atoms, 1-4 atoms are a heteroatom selected from the group consisting of N, O and S.

In a preferred embodiment of the invention, each $R^1$ is independently selected from the group consisting of substituted $C_{1-4}$ alkyl, substituted $C_{2-6}$ cycloalkyl and substituted $C_{1-4}$ alkoxy, said latter 3 groups being optionally substituted with $C_{2-6}$ heterocyclic, the term "$C_{2-6}$ heterocyclic" as used herein means heterocyclic group containing from 3 to 6 carbon atoms, 1-4 atoms are a heteroatom selected from the group consisting of N, O and S.

In a preferred embodiment of the invention, the term "$C_{2-10}$ heteroaryl" as used in Ar means heteroaryl group containing from 5 to 10 carbon atoms, 1-4 atoms are a heteroatom selected from the group consisting of N, O and S.

In a preferred embodiment of the invention, one or more of the hydrogens on the Ar is further optionally replaced with $C_{1-4}$ alkyl, the term "$C_{1-4}$ alkyl" as used herein is preferably selected from the group consisting of methyl, ethyl, n-propyl, isopropyl, n-butyl, isobutyl or tert-butyl. When one or more of the hydrogens on the Ar are further optionally replaced with $C_{1-4}$alkoxy, the term "$C_{1-4}$ alkoxy" as used herein is preferably selected from the group consisting of methoxy, ethoxy, n-propoxy, isopropoxy, n-butoxy, iso-butoxy or tert-butoxy.

In a preferred embodiment of the invention, Ar is preferably selected from the group consisting of

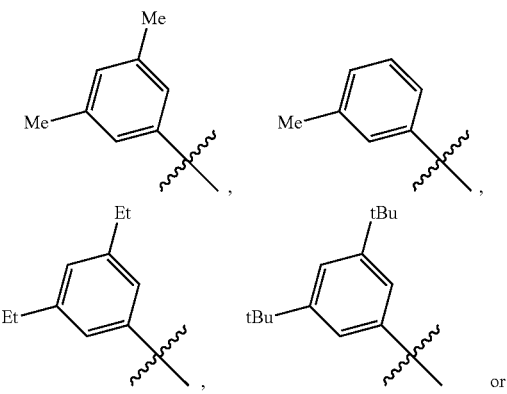

-continued

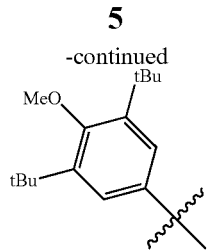

In a preferred embodiment of the invention, wherein Ar is independently selected from the $C_{6-14}$ aryl, such as phenyl preferably. $R^1$ is independently selected from the group consisting of $C_{1-4}$alkyl or $C_{1-4}$alkoxy, such as methyl or methoxy preferably. $R^2$ is independently selected from the group of $C_{1-4}$alkyl, such as methyl preferably. $R^3$ and $R^4$ are independently or simultaneously selected from the group consisting of H or $C_{1-4}$alkyl, such as H or methyl preferably. And n is for 2, X is Cl⁻ or Br⁻.

In a preferred embodiment of the invention, wherein Ar is independently selected from the $C_{6-14}$ aryl, such as phenyl preferably. $R^1$ is independently selected from the group consisting of $C_{1-4}$alkyl or $C_{1-4}$alkoxy, such as methyl or methoxy preferably. $R^2$ is independently selected from the group of $C_{1-4}$alkyl, such as methyl preferably. $R^3$ is independently selected from the group consisting of $C_{1-4}$alkyl, such as methyl preferably. $R^4$ is independently selected from the group consisting of H or $C_{1-4}$alkyl, such as H or methyl preferably. And n is 1 or 2, X is Cl⁻ or Br⁻.

In a preferred embodiment of the invention,

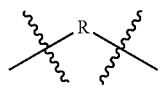

is selected from the group of

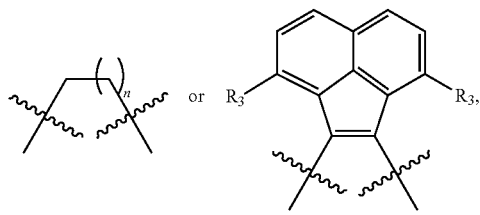

Ar is independently selected from the $C_{6-14}$ aryl, such as phenyl preferably. One or more of the hydrogens on the Ar is further optionally replaced with $C_{1-4}$alkyl or $C_{1-4}$alkoxy, $R^1$ is independently selected from the group consisting of $C_{1-4}$alkyl or $C_{1-4}$alkoxy preferably, more preferably is methyl or methoxy. $R^3$ is independently selected from the group of $C_{1-4}$ alkyl preferably, more preferably is methyl. $R^4$ is independently selected from the group consisting of H or $C_{1-4}$ alkyl preferably, more preferably is H or methyl. And n is for 2, X is Cl⁻ or Br⁻.

In a preferred embodiment of the invention,

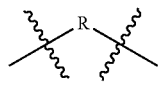

is selected from the group of

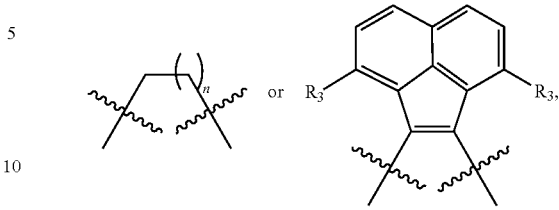

Ar is independently selected from the $C_{6-14}$ aryl preferably, more preferably is phenyl. One or more of the hydrogens on the Ar is further optionally replaced with $C_{1-4}$alkyl or $C_{1-4}$alkoxy, $R^1$ and $R^3$ are independently or simultaneously selected from the group consisting of $C_{1-4}$alkyl preferably, more preferably is methyl. $R^4$ is independently selected from the group consisting of H; n is 1, X is Cl⁻.

In a preferred embodiment of the invention,

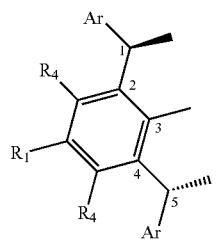

is selected from the group of

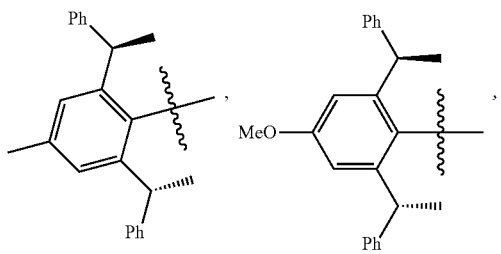

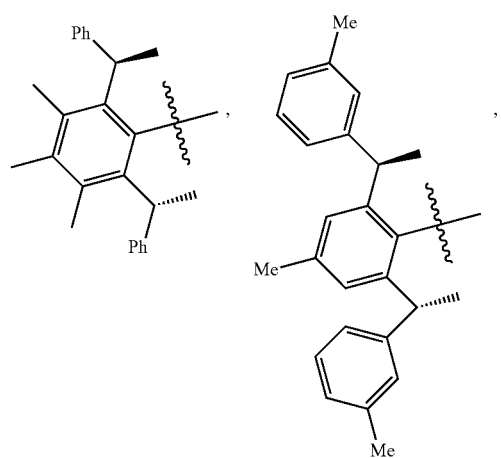

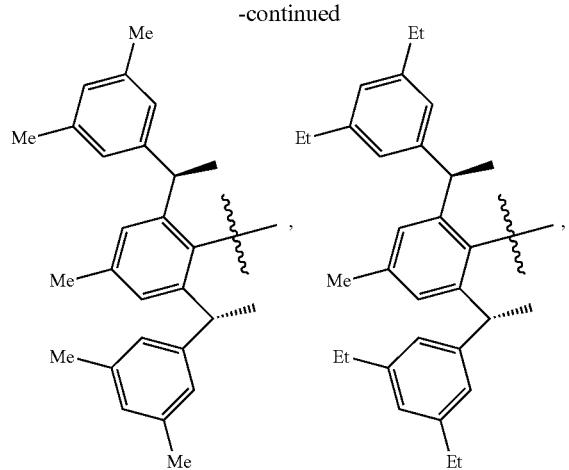
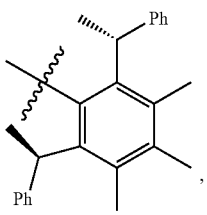
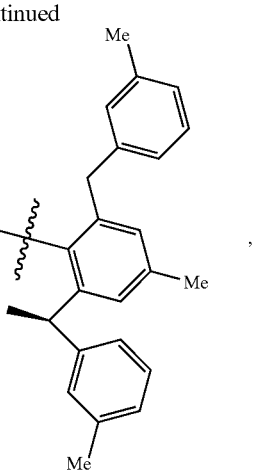
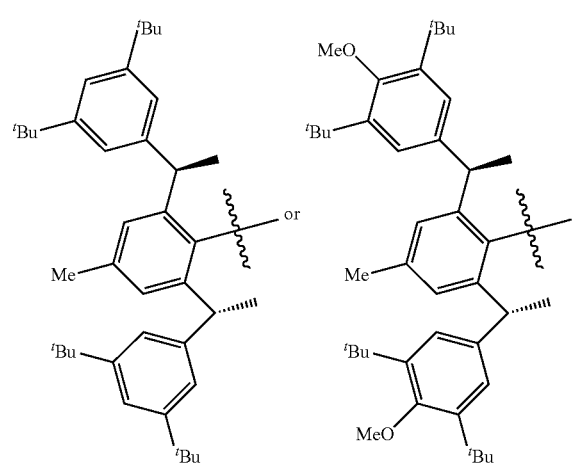
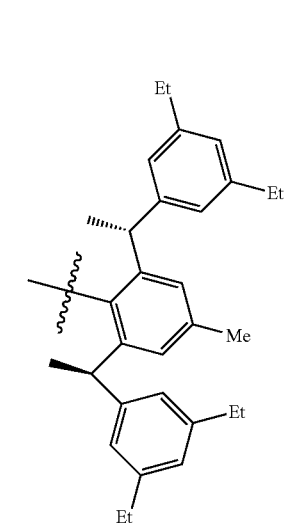
In a preferred embodiment of the invention,
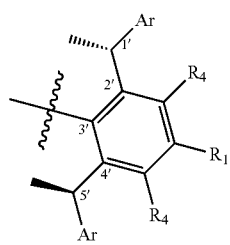
is selected from the group of
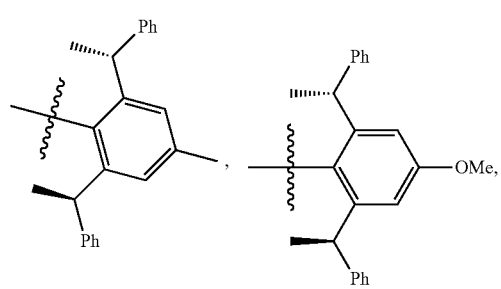
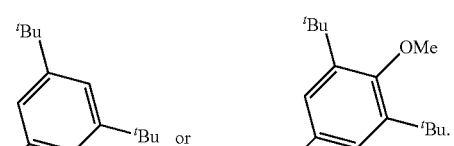
The chiral 1, 3-diaryl imidazole carbene precursor, as shown in formula S is selected from the compound consisting of A, B or C.

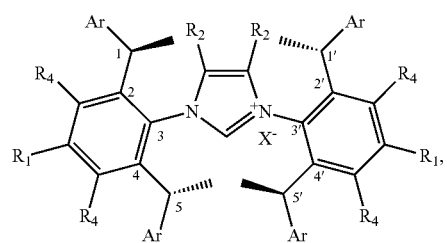
1R,5R,1'R,5'R
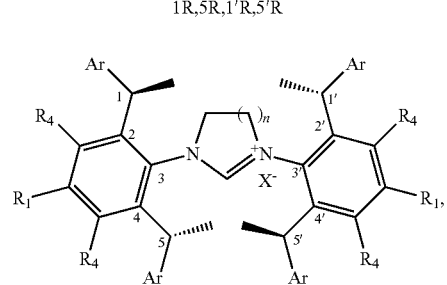
1R,5R,1'R,5'R
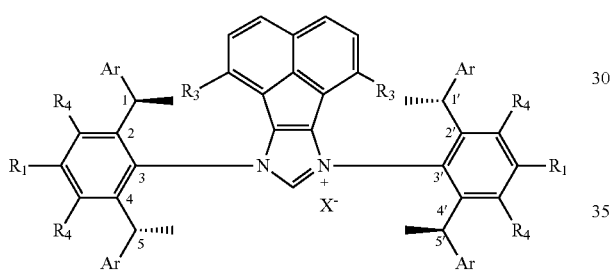
1R,5R,1'R,5'R
Wherein R¹, R², R³, R⁴, Ar, n and X⁻ are the same as before.
The chiral 1, 3-diaryl imidazole carbene precursor, as shown in formula S may be any following compounds.
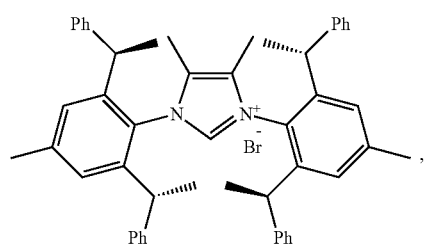
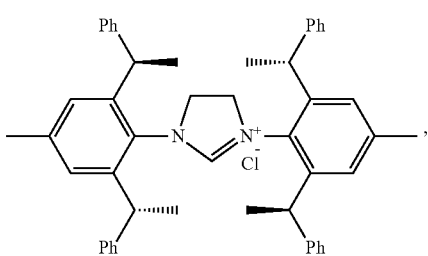
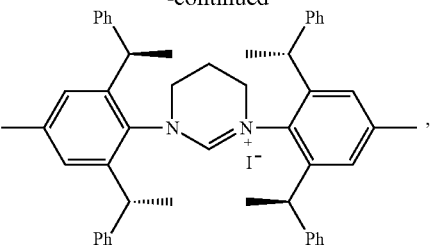
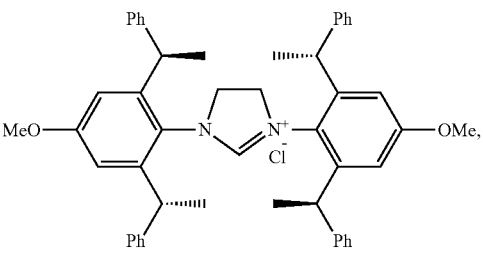
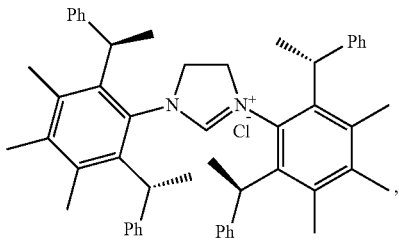
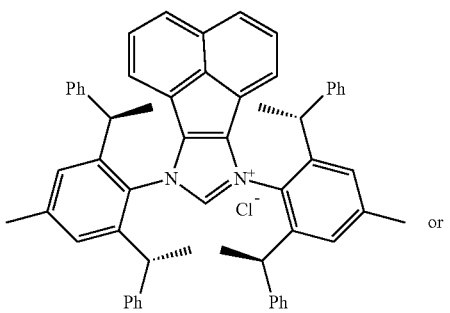
or
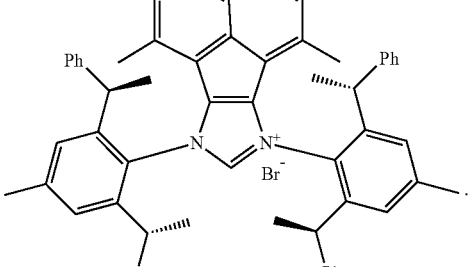
The chiral 1, 3-diaryl imidazole carbene precursor, as shown in formula S may be any following compounds preferably.

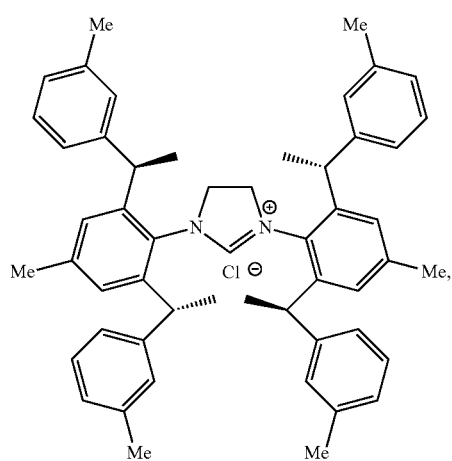
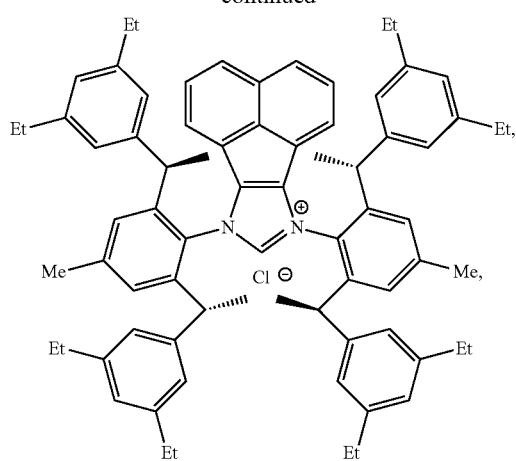
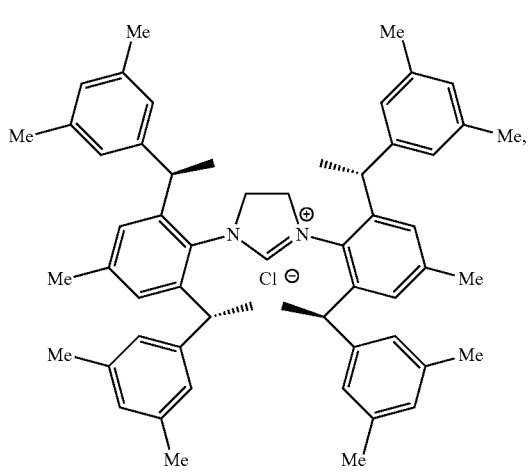
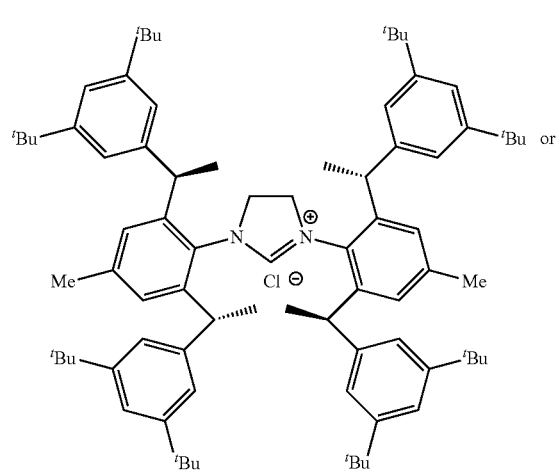
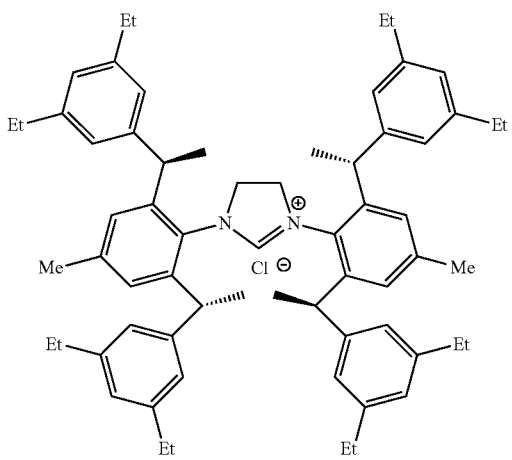
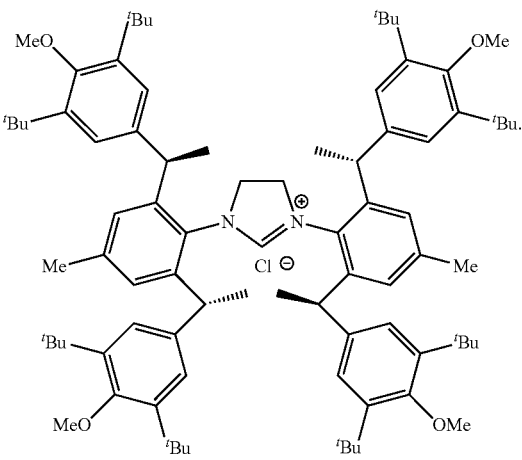

The methods of preparation of the compound as shown in formula S may be any following methods, for example:

When R is selected from the group of

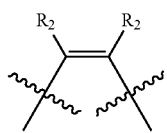 or 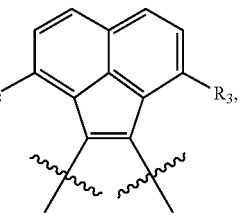

S is prepared by method a) which includes the following steps: compounds of formula S' suitably reacts with halomethyl alkyl ether as follows.

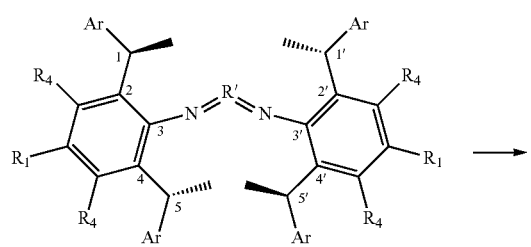

S'

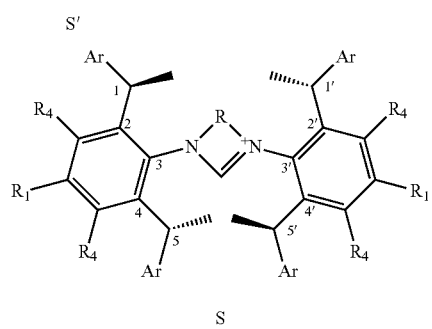

S

Wherein,

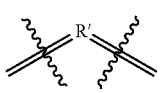

is selected from the group of

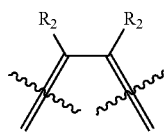 or 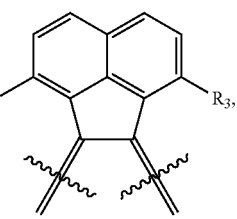

R is selected from the group of

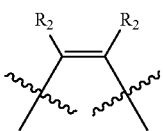 or 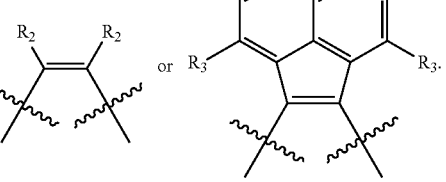

$R_1$, $R_2$, $R_3$, $R_4$, Ar, n and $X^-$ are the same as before.

Or when

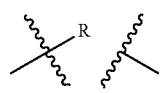

is selected from the

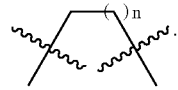

S is prepared by method b) which includes the following steps: compounds of formula M6 are suitably reacted with S2 in the presence of a base as follows.

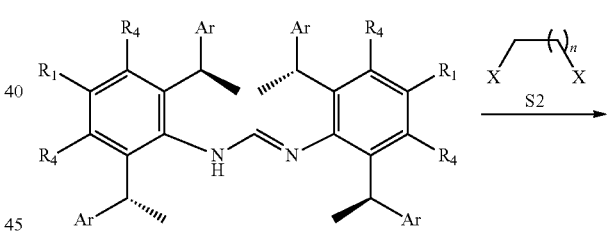

M6

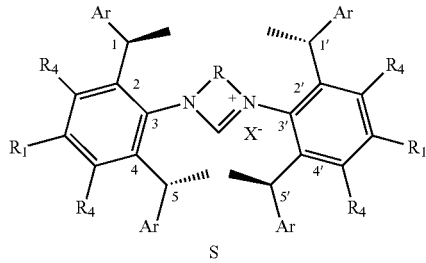

S

Wherein,

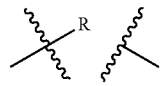

is selected from the

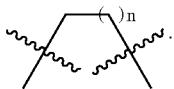

$R_1$, $R_4$, Ar, $X^-$ and n are the same as before. X means halogen consisting of Cl, Br or I.

Or when

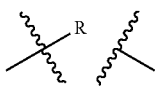

is selected from the

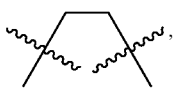 [SMILES: *CC*]

S is prepared by method c) which includes the following steps: compounds of formula M8 are suitably reacted with triethyl orthoformate in the presence of $NH_4X$ as follows.

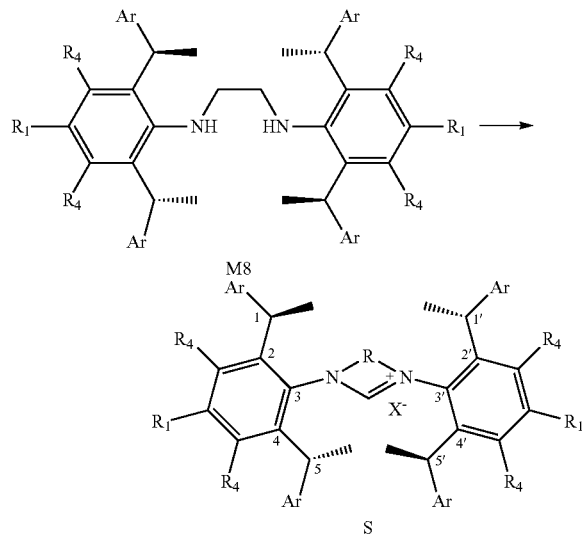

Wherein,

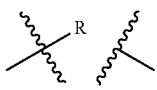

is selected from the

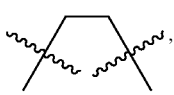 [SMILES: *CC*]

$R_1$, $R_4$, Ar and $X^-$ are the same as before.

Wherein method a), solvent-free conditions are preferably.

Wherein method a), the halomethyl alkyl ether used herein is as would be well known to those skilled in the art, such as chloromethyl ether and/or bromomethyl ether.

Wherein method a), the halomethyl alkyl ether used herein in an amount of molar ratio which is as would be well known to those skilled in the art of generally 5 to 30 equivalents preferably, base on the compound represented by the formula S', more preferably is 10 to 20 equivalents.

Wherein method a), the temperature used herein is as would be well known to those skilled in the art, which is generally 80° C. to 130° C.

Wherein method a), the process of the reaction can be monitored by the conventional monitoring method (such as $^1H$ NMR) of such reaction as would be well known to those skilled in the art. Generally, the endpoint of the reaction was determined by the compound S' was completely transformed or no longer reacts. The reaction time is preferably 10 to 30 hours, for example, 12 to 24 hours.

Wherein method a), after the reaction is completed, a workup step may be further included. The workup step is as would be well known to those skilled in the art, and the present invention preferably includes the following workup steps: adding organic solvent (e.g. diethyl ether) to the reaction solution after the reaction is completed, precipitating out the solid, suction filtration, washing (e.g. washing with ether) the solid and dry. Alternatively, the present invention preferably includes the following workup steps, solid-liquid separation (preferably suction filtration) is performed on the reaction liquid after the reaction is completed to obtain a solid.

Wherein method b), the solvent used herein is as would be well known to those skilled in the art, which is selected from one or more of following solvent consisting of nitrile, halogenated hydrocarbon, amid; and ether. The nitrile preferably is selected from acetonitrile. The halogenated hydrocarbon preferably is selected from dichloromethane and/or chloroform. The amide preferably is selected from N, N-dimethylformamide. The ether preferably is selected from 1,2-dioxane and/or tetrahydrofuran. The solvent used herein in a volume molar ratio which is as would be well known to those skilled in the art of generally 1 to 5 L/mol preferably, base on the compound M6, more preferably is 1 to 2 L/mol, for example, 1.5 L/mol.

Wherein method b), the base used herein is as would be well known to those skilled in the art, which is an organic base and/or inorganic base preferably. The preferable organic base used herein is tertiary amine consisting of DIPEA and/or trimethylamine. The preferable inorganic base used herein is alkali carbonate, which is selected from one or more of the following bases consisting of $Na_2CO_3$, $K_2CO_3$ and $Cs_2CO_3$. The base used herein in an amount of molar ratio is as would be well known to those skilled in the art of generally 0.9 to 1.5 equivalents, base on the compound represented by the formula M6, more preferably is 0.9 to 1.2 equivalents, for example, 1.1 equivalents.

Wherein method b), the compound represented by the formula S2 used herein in an amount of molar ratio is as would be well known to those skilled in the art of generally 1.2 to 5 equivalents, base on the compound represented by the formula M6, more preferably is 2 to 4 equivalents, for example, 3 equivalents.

Wherein method b), the temperature used herein is as would be well known to those skilled in the art of generally 50° C. to 100° C., for example, 80° C.

Wherein method b), the process of the reaction can be monitored by the conventional monitoring method (such as $^1$H NMR) of such reaction as would be well known to those skilled in the art. Generally, the endpoint of the reaction was determined by the compound M6 was completely transformed or no longer reacts. The reaction time is preferably 8 to 15 hours, for example, 12 hours.

Wherein method b), after the reaction is completed, a workup step may be further included. The workup step is as would be well known to those skilled in the art, and the present invention preferably includes the following workup steps: the solvent was removed (rotary evaporator), adding organic solvent (such as dichloromethane), and wash with alkaline (such as saturated potassium carbonate solution), concentrate, and wash the solid with ether solvent (such as ether).

Wherein method c), the compound represented by the formula $NH_4X$ used herein is selected from $NH_4Cl$ or $NH_4Br$. The compound represented by the formula $NH_4X$ used herein in an amount of molar ratio is as would be well known to those skilled in the art of generally 1.2 to 3 equivalents, base on the compound represented by the formula M8, more preferably is 1.2 to 2 equivalents, for example, 1.5 equivalents.

Wherein method c), the triethyl orthoformate used herein is both raw materials and solvents, and in a volume molar ratio V/M as would be well known to those skilled in the art of generally 3 to 15 L/mol, base on the compound represented by the formula M8, more preferably is 3 to 6 L/mol, for example, 4.66 L/mol or 11.36 L/mol.

Wherein method c), the temperature used herein is as would be well known to those skilled in the art of generally 90° C. to 130° C., more preferably is 90° C. to 120° C., for example, 110° C. to 115° C.

Wherein method c), the process of the reaction can be monitored by the conventional monitoring method (such as $^1$H NMR) of such reaction as would be well known to those skilled in the art. Generally, the endpoint of the reaction was determined by the compound M8 that was completely transformed or no longer reacts. The reaction time is preferably 10 to 30 hours, for example, 15 to 18 hours.

Wherein method c), after the reaction is completed, a workup step may be further included. The workup step is as would be well known to those skilled in the art, and the present invention preferably includes the following workup steps: after the reaction is completed, the filter cake is washed with organic solvent (such as ether) and dried. Or preferably, it includes the following workup steps: after silica gel column chromatography and then purified by column chromatography (wherein the conditions for purified by silica gel column chromatography and column chromatography is as would be well known to those skilled in the art).

The method of preparation of the chiral 1, 3-diarylimidazole carbene precursor as shown in formula S may be further included following steps: in the organic solvent, the compound S" reacted with the compound R" in the presence of acid can be carried out as follows to obtain the compound S'.

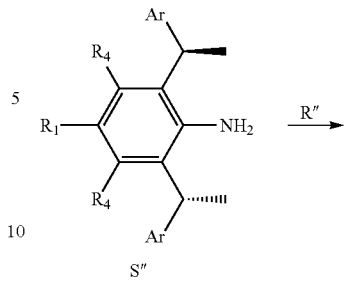

Wherein the compound R" is selected from the group of

The is selected from the group of $R_1$, $R_2$, $R_3$, $R_4$ and Ar are the same as before.

Or wherein method c) may be further included the following steps: in the organic solvent, the compound M5 reacted with a reductant to obtain the compound M6 can be carried out as follows.

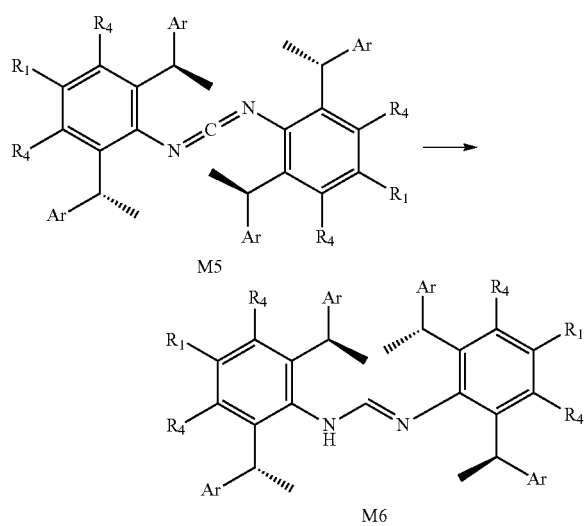

M5

M6

Wherein $R_1$, $R_4$ and Ar are the same as before.

Or wherein method c) may be further included the following steps: the compound M7 can be reduced to the compound M8 as follows.

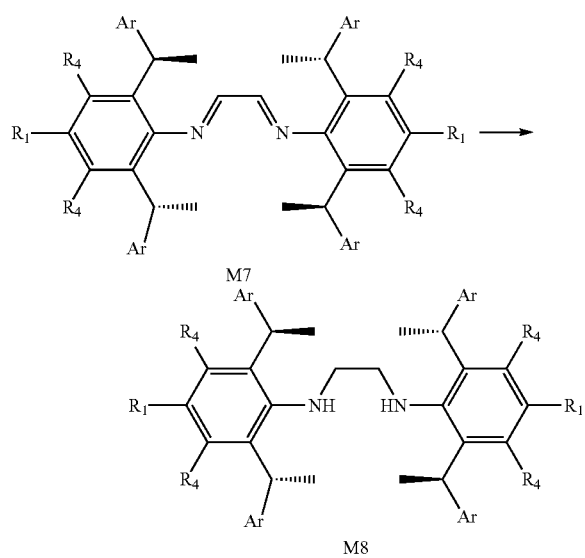

M7

M8

Wherein $R_1$, $R_4$ and Ar are the same as before.

Wherein the method of preparation of the compound S', the solvent used herein is as would be well known to those skilled in the art, which is selected from one or more of following solvent consisting of alcohol, nitrile and aromatic solvents (e.g. toluene), further preferred alcohol solvents and/or nitrile solvents, for example, ethanol and/or acetonitrile. The solvent used herein in a volume molar ratio which is as would be well known to those skilled in the art of generally 2 to 20 L/mol preferably, base on the compound S'', more preferably is 3 to 10 L/mol, for example, 5.25 L/mol.

Wherein the method of preparation of the compound S', the acid used herein is as would be well known to those skilled in the art, which is selected from organic acids or their hydrates. The organic acids used herein is selected from $C_{1-3}$ carboxylic acid and/or aryl sulfonic acid, for example, acetic acid and/orp-toluenesulfonic acid. The acid used herein in an amount of molar ratio is as would be well known to those skilled in the art of generally catalytic amount, base on the compound S'', 0.3% to 10% equivalents preferably, for example, 0.3% to 5% equivalents, more preferably is 0.3% to 1% equivalents, for example, 0.5% equivalents.

Wherein the method of preparation of the compound S', the compound R'' used herein in an amount of molar ratio is as would be well known to those skilled in the art of 2 to 3 equivalents, base on the compound S'', more preferably is 2 to 2.5 equivalents, for example, 2 equivalents.

Wherein the method of preparation of the compound S', the temperature used herein is as would be well known to those skilled in the art of generally 30° C. to 140° C., for example, 30° C. to 100° C. or 40° C. to 80° C.

Wherein the method of preparation of the compound S', the process of the reaction can be monitored by the conventional monitoring method (such as $^1$H NMR) of such reaction as would be well known to those skilled in the art. Generally, the endpoint of the reaction was determined by the compound S'' was completely transformed or no longer reacts. The reaction time is preferably 10 to 20 hours, for example, 12 to 15 hours.

Wherein the method of preparation of the compound S', after the reaction is completed, a workup step may be further included. The workup step is as would be well known to those skilled in the art, and the present invention preferably includes the following workup steps: after the reaction is completed, suction filtration, the filter cake is washed with organic solvent (such as ethanol) and dried to obtain compound S'.

Wherein the method of preparation of the compound M6, CThe alcohol solvents used herein preferred ethanol. The ether solvents used herein preferred tetrahydrofuran. The solvents used herein in a volume molar ratio, which is as would be well known to those skilled in the art of generally 10 to 30 L/mol preferably, base on the compound M5, for example, 18 to 22.5 L/mol.

Wherein the method of preparation of the compound M6, the reducing agent used herein is as would be well known to those skilled in the art, borohydrides are preferred, and sodium borohydride is more preferred. The reducing agent used herein in an amount of molar ratio is as would be well known to those skilled in the art of 2 to 6 equivalents, base on the compound M5, for example, 4 equivalents.

Wherein the method of preparation of the compound M6, the temperature used herein is as would be well known to those skilled in the art of generally room temperature, for example, 20° C. to 30° C.

Wherein the method of preparation of the compound M6, the process of the reaction can be monitored by the conventional monitoring method (such as $^1$H NMR) of such reaction as would be well known to those skilled in the art. Generally, the endpoint of the reaction was determined by the compound M5 was completely transformed or no longer reacts. The reaction time is preferably 0.5 to 2 hours, for example, 1 hour.

Wherein the method of preparation of the compound M6, after the reaction is completed, a workup step may be further included. The workup step is as would be well known to those skilled in the art, and the present invention preferably includes the following workup steps: after the reaction is completed. It was quenched by adding water, extracted with an organic solvent (such as ethyl acetate), concentrated, and purified by column chromatography to obtain compound S'.

Wherein the method of preparation of the compound M8, the reduction reaction used herein is preferably in an organic solvent. The organic solvent used herein is as would be well known to those skilled in the art as conventional solvents, ether solvents are preferred, for example, tetrahydrofuran. The solvents used herein in a volume molar ratio which is as would be well known to those skilled in the art of generally 4 to 10 L/mol preferably, base on the compound M7, more preferably is 4 to 8 L/mol, for example, 6.85 L/mol.

Wherein the method of preparation of the compound M8, the reducing agent used herein is as would be well known to those skilled in the art as a conventional reducing agent, lithium aluminum hydride is preferred. The reducing agent used herein in an amount of molar ratio is as would be well known to those skilled in the art of 2 to 7 equivalents, base on the compound M8, for example, 3 equivalents. The reducing agent is preferably added under an ice bath condition (for example, −5° C. to 5° C., preferably 0° C.).

Wherein the method of preparation of the compound M8, the temperature used herein in the reduction reaction is as would be well known to those skilled in the art, it is preferably 0° C. to 50° C., such as 10° C. to 30° C. or 30° C. to 50° C., and more preferably 30° C. to 45° C., such as 40° C.

Wherein the method of preparation of the compound M8, the process of the reduction reaction can be monitored by the conventional monitoring method (such as $^1$H NMR) of such reaction as would be well known to those skilled in the art. Generally, the endpoint of the reaction was determined by the compound M7 was completely turnover or no longer reacts. The reaction time is preferably 10 to 20 hours, for example, 12 hours.

Wherein the method of preparation of the compound M8, after the reduction reaction is completed, a workup step may be further included. The workup step is as would be well known to those skilled in the art, and the present invention preferably includes the following workup steps: quench the reaction (for example, quench with an aqueous alkaline solution), extract with organic solvents, combine the organic layers, dry, concentrate, and purify by column chromatography to obtain compound M8. The column chromatography purification can adopt the conditions of conventional column chromatography purification in the art.

The invention also provides methods of preparation of compound A, which includes the following steps:

(a) The compound N1 reacted with compound N2, as shown below, to prepare compound M1.

(b) With [Rh] catalyst and (Rc,Sp)-DuanPhos, the compound M1 was hydrogenated compound M2.

(c) The compound M2 reacted with S1 to prepare compound M3, as shown below.

(d) The compound M2 reacted with halomethyl alkyl ether to prepare compound A as shown below.

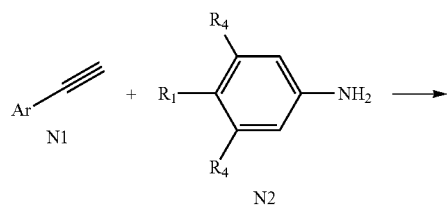

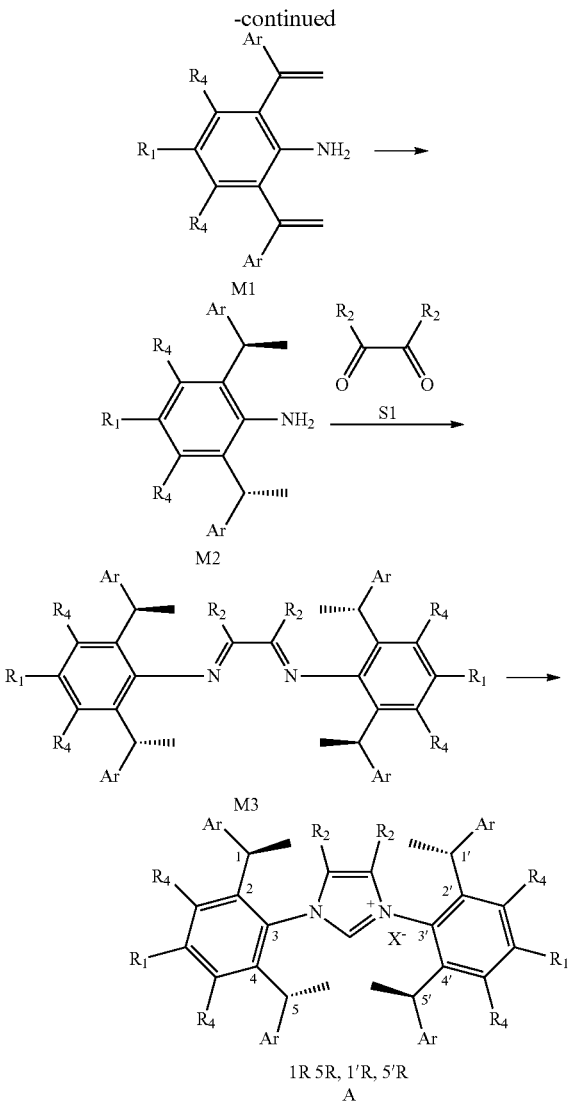

Wherein $R_1$, $R_2$, $R_3$, $R_4$, Ar, n and $X^-$ are the same as before.

Wherein the method to compound A, Step (a) is preferably performed in the presence of montmorillonite.

Wherein the method to compound A, solvent-free condition is preferably in Step (a).

Wherein the method to compound A, Step (a) preferably includes the following steps: compound N1 and N2 are mixed with montmorillonite, and then the reaction is performed at 120° C. to 160° C.

Wherein the method to compound A, in step (a), the dosage of compound N1 and N2 is not specified, as long as the progress of reaction is not affected. The compound N2 used herein in an amount of molar ratio is as would be well known to those skilled in the art of 0.1 to 1 equivalents, base on the compound N1, 0.5 equivalents. The dosage of montmorillonite is not specified, as long as the progress of reaction is not affected. The process of the reaction can be monitored by the conventional monitoring method (such as TLC, $^1$H NMR, GC, HPLC) of such reaction as would be well known to those skilled in the art. Generally, the endpoint of the reaction was determined by the compound N1 or N2 that was completely turnover or no longer reacts.

The reaction time is preferably 6 to 10 hours, for example, 8 hours. After the reduction reaction is completed, a workup step may be further included. The workup step is as would be well known to those skilled in the art, and the present invention preferably includes the following workup steps: the reaction liquid is mixed with organic solvent (preferably ester solvent, such as ethyl acetate), concentrated, and then mixed with ether solvent (such as ether), solid-liquid separation (such as suction filtration) and solid drying.

Wherein the method to compound A, in step (b), the reaction is preferably carried out in a solvent. The solvent is preferably an alcohol solvent and/or a halogenated hydrocarbon solvent, such as methanol and/or dichloromethane. The amount of the solvent may not be specifically limited, as long as the progress of reaction is not affected, it is preferred that the volume molar ratio with compound M1 is 1 to 5 L/mol, for example, 2 to 3 L/mol. The [Rh] catalyst used herein in the hydrogenation reaction is as would be well known to those skilled in the art of preferred $(NBD)_2RhBF_4$ (which is a commercial product, purchased from Energy Chemical Technology (Shanghai) Co., Ltd.). The [Rh] catalyst and (Rc, Sp)-DuanPhos herein in an amount of molar ratio is as would be well known to those skilled in the art of generally catalytic amount, base on the compound M1, 0.1% to 1% equivalents preferably, for example, 0.5% to 0.6% equivalents. The temperature used herein is room temperature. The process of the reaction can be monitored by the conventional monitoring method (such as TLC, $^1$H NMR, GC, HPLC) of such reaction as would be well known to those skilled in the art. Generally, the endpoint of the reaction was determined by the compound M1 was completely turnover or no longer reacts. The reaction time is preferably 12 to 30 hours, for example, 24 hours. After the reduction reaction is completed, a workup step may be further included. The workup step is as would be well known to those skilled in the art, and the present invention preferably includes the following workup steps: the reaction liquid is separated by solid-liquid separation (such as suction filtration) and washed by organic solvent (preferably alcohol solvent, such as methanol).

Wherein the method to compound A, in step (b), the reaction is preferably carried out includes the following steps: The compound M1 is mixed with alcohol, and then mixed with the mixed solution of a [Rh] catalyst, (Rc, Sp)-DuanPhos and a halogenated hydrocarbon solvent, and then hydrogen is passed through to perform the reaction.

Wherein the method to compound A, the conditions of step (c) are the same as that of compound S'.

Wherein the method to compound A, the conditions of step (d) are the same as the method of step (a) for the preparation of the aforementioned compound S.

The invention also provides a method for synthesis of compound B, which includes the following steps:

(a) The compound M2 reacted with triphosgene to obtain compound M4.

(b) The compound M4 reacted with alumina and phosphorus pentoxide to obtain compound M5.

(c) The compound M5 was reduced to obtain compound M6, as shown below.

(d) The compound M6 reacted with compound S2 to obtain compound B, as shown below.

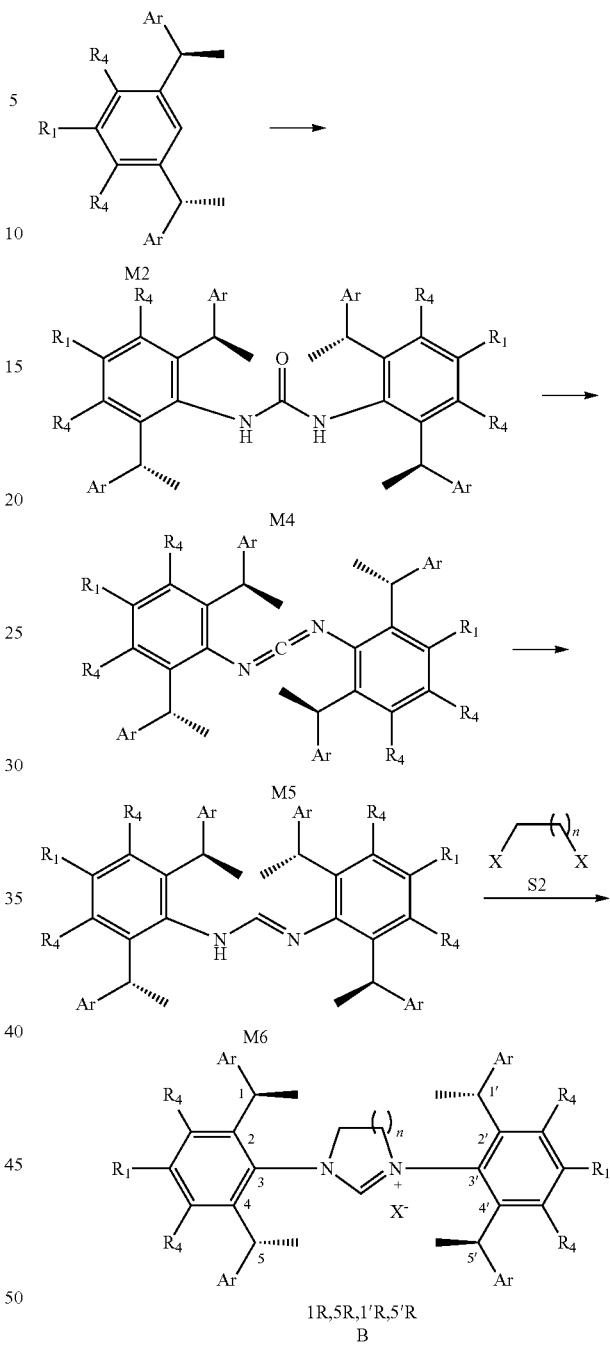

Wherein $R_1$, $R_4$, Ar, n and $X^-$ are the same as before.

Wherein the method to compound B, in step (a), the reaction is preferably performed in the presence of a solvent and a catalyst. The solvent used herein is as would be well known to those skilled in the art, which is selected from halogenated hydrocarbon solvents, for example, DCE. The amount of the solvent used herein is not specifically limited, as long as it does not affect the progress of the reaction. Preferably, its volume molar ratio to the compound M2 is 1 to 5 L/mol, such as 2 L/mol. The catalyst used herein is as would be well known to those skilled in the art, and is preferably DMAP. The amount of catalyst used is not specifically limited, as long as it does not affect the progress of the reaction, the catalyst used herein in an amount of molar ratio is as would be well known to those skilled in the art of 1 to 3 equivalents, base on the compound M2, for example, 1 to 2 equivalents. The amount of triphosgene used is not specifically limited, as long as it does not affect the progress of the reaction, the catalyst used herein in an amount of molar ratio is as would be well known to those skilled in the art of 0.1 to 3 equivalents, base on the compound M2, for example, 0.2 to 0.5 equivalents. The temperature used herein is as would be well known to those skilled in the art of normal temperature, and is preferably −78° C. to 100° C., for example, −78° C. to 80° C. The process of the reaction can be monitored by the conventional monitoring method (such as TLC, $^1$H NMR, GC, HPLC) of such reaction as would be well known to those skilled in the art. Generally, the endpoint of the reaction was determined by the compound M2 was completely turnover or no longer reacts. After the reduction reaction is completed, a workup step may be further included. The workup step is as would be well known to those skilled in the art, and the present invention preferably includes the following workup steps: the reaction liquid is separated by solid-liquid separation (such as suction filtration), washing with water, drying (such as spin drying under reduced pressure), and recrystallize (recrystallize in an alkane solvents such as naphthene).

Wherein the method to compound B, in step (b), the reaction is preferably performed in the presence of a solvent. The solvent used herein is pyridine preferably. The amount of the solvent used herein is not specifically limited, as long as it does not affect the progress of the reaction. Preferably, its volume molar ratio to the compound M4 is 5 to 20 L/mol, such as 12 to 13 L/mol. The amount of alumina and phosphorus pentoxide used herein is not specifically limited, as long as it does not affect the progress of the reaction, which is in an amount of molar ratio is as would be well known to those skilled in the art of 10 to 20 equivalents, base on the compound M4, for example, 12 to 14 equivalents. The temperature used herein is as would be well known to those skilled in the art of room temperature. The process of the reaction can be monitored by the conventional monitoring method (such as TLC, $^1$H NMR, GC, HPLC) of such reaction as would be well known to those skilled in the art. Generally, the endpoint of the reaction was determined by the compound M4 was completely turnover or no longer reacts. After the reduction reaction is completed, a workup step may be further included. The workup step is as would be well known to those skilled in the art, and the present invention preferably includes the following workup steps: the reaction liquid is separated by solid-liquid separation (such as suction filtration), washing and drying.

Wherein the method of preparation of compound B, the conditions of the method of step (c) are the same as the preparation of the aforementioned compound M6.

Wherein the method of preparation of the compound B, the conditions of the method of step (d) are the same as the method of step (b) for the preparation of the aforementioned compound S.

The invention also provides a method for the preparation of compound B2, which includes the following steps:

(a) The compound M2 reacted with glyoxal as follows to obtain compound M7.

(b) The compound M7 reacted with lithium aluminum hydride as follows to obtain compound M8.

(c) The compound M8 reacted with triethyl orthoformate as follows to obtain compound B2.

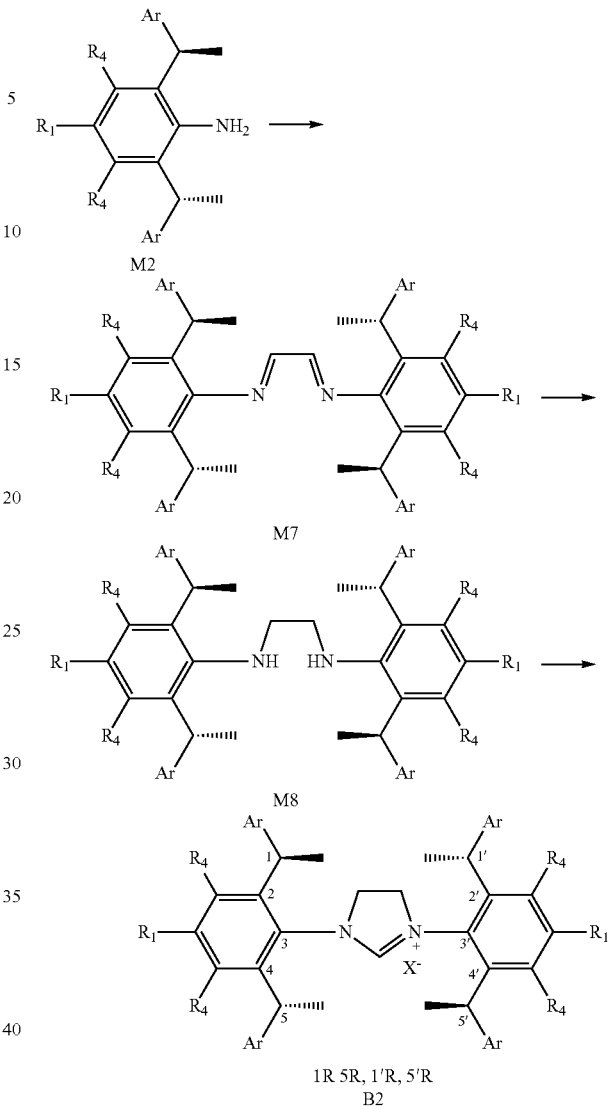

Wherein $R_1$, $R_4$, Ar and $X^-$ are the same as before.

Wherein the method of preparation of the compound B2, in step (a), the reaction is preferably performed in the presence of a solvent and an acid. The solvent used herein is as would be well known to those skilled in the art, which is selected from alcohol solvents, for example, ethanol. The amount of the solvent used herein is not specifically limited, as long as it does not affect the progress of the reaction. Preferably, its volume molar ratio to the compound M2 is 1 to 10 L/mol, such as 4 to 6 L/mol. The acid used herein is as would be well known to those skilled in the art, $C_{1-3}$ Alkyl carboxylic acid is preferred. The amount of acid used herein is not specifically limited, as long as it does not affect the progress of the reaction, which is in an amount of molar ratio is as would be well known to those skilled in the art of 1% to 10% equivalents, base on the compound M2, for example, 5% equivalents. The amount of glyoxal used herein is in an amount of molar ratio is as would be well known to those skilled in the art of 0.5 to 1 equivalents, base on the compound M2. The temperature used herein is as would be well known to those skilled in the art of normal temperature. It is preferably 10° C. to the reflux temperature of the solvent at normal pressure, more preferably 10° C. to 50° C., such as 40° C. The process of the reaction can be monitored by the conventional monitoring method (such as TLC, $^1$H NMR, GC, HPLC) of such reaction as would be well known to those skilled in the art. Generally, the endpoint of the reaction was determined by the compound M2 was completely turnover or no longer reacts. After the reduction reaction is completed, a workup step may be further included. The workup step is as would be well known to those skilled in the art, and the present invention preferably includes the following workup steps: solid-liquid separation (such as suction filtration), the solid was washed with alcohol solvent and dried Wherein the method to compound B2, Step (a) preferably includes the following steps: mixing compound M2 with a solvent, adding acid at 70° C. to 80° C., finally adding glyoxal to obtain compound M7.

Wherein the method to compound B2, in step (a), glyoxal is preferably added to the reaction system as an aqueous solution of glyoxal. The concentration of the glyoxal aqueous solution is as would be well known to those skilled in the art, preferably 40% of the glyoxal aqueous solution (the percentage refers to the percentage of the mass of glyoxal in the total mass of the glyoxal aqueous solution).

Wherein the method to compound B, the conditions of the method of step (b) are the same as the method of the preparation of the aforementioned compound M8.

Wherein the method to compound B, the conditions of the method of step (c) are the same as the method of step (c) for the preparation of the aforementioned compound S.

The invention also provides a method for synthesis of compound C, which includes the following steps:

(a) The compound M2 reacted with S3 to obtain compound M, as shown below.

(b) The compound M9 reacted with chloromethyl ether to obtain compound C, as shown below.

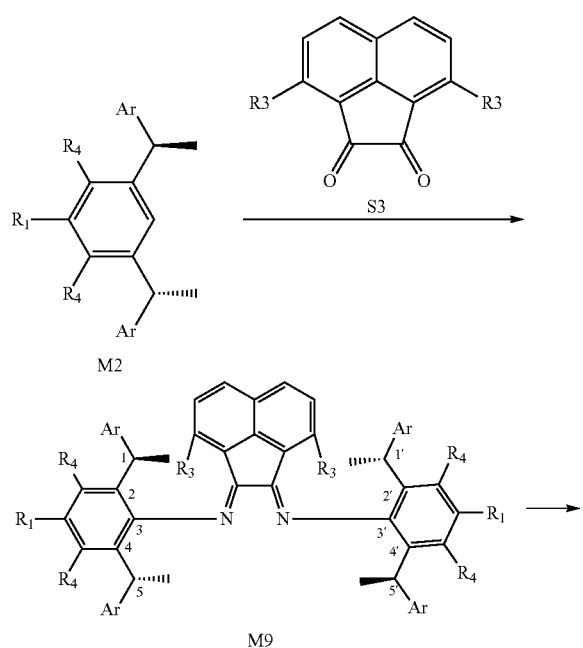

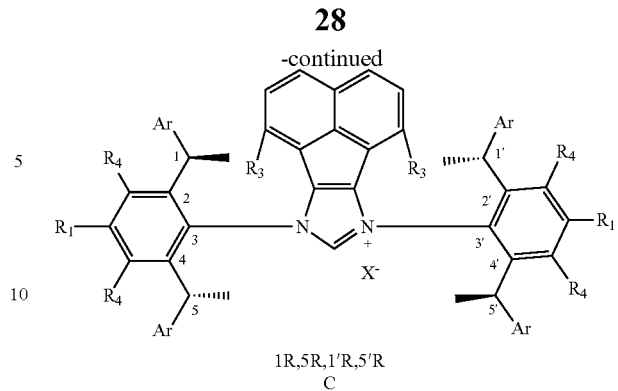

Wherein $R_1$, $R_3$, Ar and $X^-$ are the same as before.

Wherein the method of preparation of compound C, the conditions of the method of step (a) are the same as the method of the preparation of the aforementioned compound M8. S'

Wherein the method of preparation of compound C, the conditions of the method of step (b) are the same as the method (a) of the preparation of the aforementioned compound S.

This invention also provides a method to compound M6 or M8 as shown below:

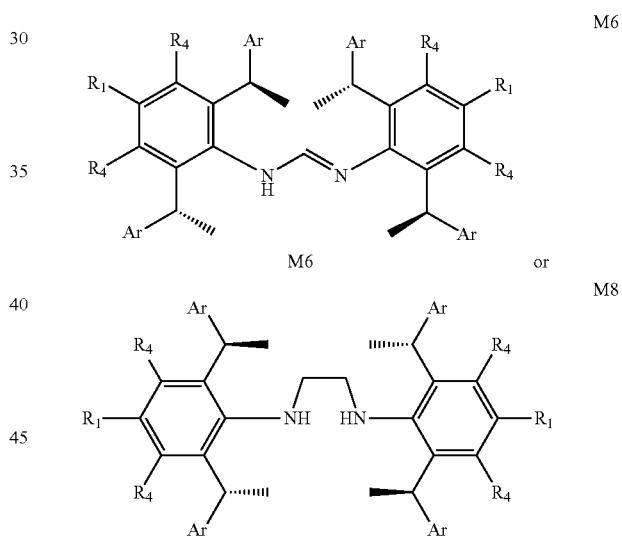

Wherein $R_1$, $R_4$ and Ar are the same as before.

This invention also provides an application of the chiral 1, 3-diarylimidazole salt carbene precursor, as shown in formula S as a catalyst in an asymmetric catalytic reaction. The application used herein preferably hydroboration of unactivated terminal alkenes.

The hydroboration of unactivated terminal alkenes includes the following steps: In the presence of a base, copper salt and the chiral 1, 3-diarylimidazole salt carbene precursor as shown in formula S form a catalyst, which catalyze the asymmetric hydroboration of unactivated terminal alkenes.

Wherein the hydroboration of unactivated terminal alkenes, the organic solvent used herein is as would be well known to those skilled in the art, which is selected from one or more of the following solvent such as alkanes, alcohol, aromatic and ether solvents. The alkanes used herein is as would be well known to those skilled in the art such as n-hexane. The alcohol is preferably methanol. The aromatic hydrocarbon solvents are preferably benzene and/or toluene. The ether solvents are preferably tetrahydrofuran. The amount of the solvent used herein is as would be well known to those skilled in the art. Preferably, its volume molar ratio to the unactivated terminal alkenes is 200 to 300 L/mol, such as 200 L/mol. The copper salt used herein is as would be well known to those skilled in the art of a conventional copper salt, preferably a monovalent copper salt, and more preferably a copper halide, for example, copper chloride. The molar ratio of monovalent copper salt used herein and the compound represented by the formula S is 0.9 to 1.2, such as 1.0. The base used herein is as would be well known to those skilled in the art of a conventional base, preferably is alkali metal tert-butoxides, for example, sodium tert-butoxide and/or potassium tert-butoxide. The molar ratio of the unactivated terminal alkenes and the base is generally 1 to 100, base on, such as 50 to 80. The organoborane used herein is as would be well known to those skilled in the art of an organoborane, which is preferably selected from the compounds consisting of

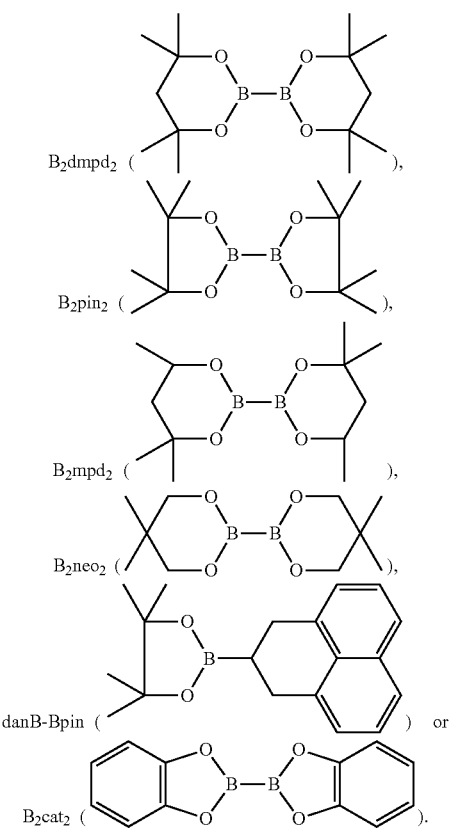

The amount of the organoborane used herein is not specifically limited, as long as it does not affect the progress of the reaction. The molar ratio of the base and organoborane used herein is generally 1 to 5, such as 1 to 2 equivalents. The temperature used herein is preferably room temperature. The completion of the reaction is when the unactivated terminal alkenes were completely transformed. The reaction time is preferably 12-30 hours, such as 24 hours. After the reaction is completed, a workup step may be further included. The workup step is as would be well known to those skilled in the art, and the present invention preferably includes the following workup steps: The reaction solution was filtered, the solvent was removed, the product was purified by column chromatography (eluent is preferably petroleum ether:ethyl acetate=40:1) to obtain the product.

Wherein the hydroboration of unactivated terminal alkenes preferably includes the following steps: the copper salt, base, and the chiral 1,3-diarylimidazole salt carbene precursor as shown in formula S are mixed with an alkane solvent, and the resulting mixture is stirred at room temperature after a diboron reagent is added, the reaction is stirred at room temperature. Finally, an alcohol and an unactivated terminal olefin as shown in Formula P are added to perform the reaction.

This present invention also provides the Cu (I)/1, 3-diarylimidazole salt carbene precursor complex:

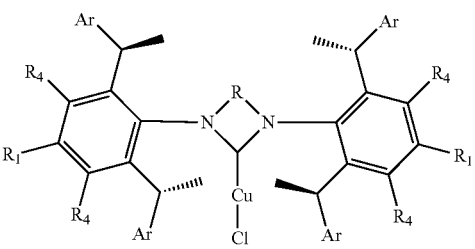

Wherein $R_1$, $R_4$, Ar and R are the same as before.

The Cu (I)/1, 3-diarylimidazole salt carbene precursor complex further preferably compound 35 as follows:

35

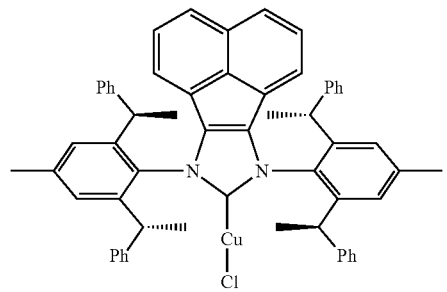

This present invention also provides the method of preparation of the complex: in the organic solvent, the chiral 1, 3-diarylimidazole carbene precursor as shown in formula S reacted with the monovalent copper salt in the presence of alkali can be carried out as follows.

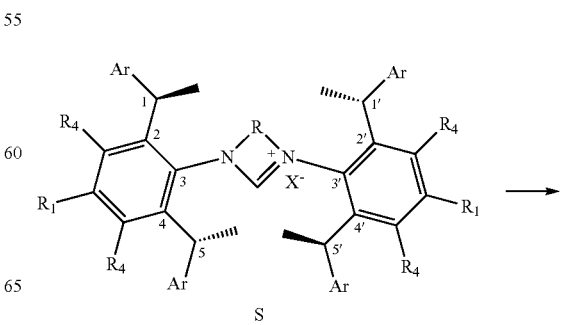

-continued

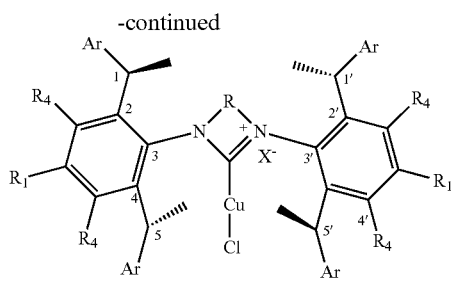

Wherein $R_1$, $R_2$, $R_3$, $R_4$, Ar, n and $X^-$ are the same one as before.

Wherein the method of preparation of the Cu (I)/1, 3-diarylimidazole salt carbene precursor complex: the organic solvent used herein is as would be well known to those skilled in the art such as low-polarity and non-proton solvent, or which selected from one or more of the following solvent consisting of alkane, arene and ether solvent. The alkane solvent used herein may be a halogenated alkane and/or an unsubstituted alkane, which is preferably selected from dichloromethane and/or hexane. The arene solvent used herein is preferably selected from benzene and/or toluene. The solvent used herein is preferably selected from tetrahydrofuran. The solvents used herein in a volume molar ratio which is as would be well known to those skilled in the art of generally 1 to 5 L/mol preferably, base on the chiral 1, 3-diarylimidazole salt carbene precursor as shown in formula S, for example, 5 L/mol.

Wherein the method of preparation of the Cu (I)/1, 3-diarylimidazole salt carbene precursor complex: The base used herein is as would be well known to those skilled in the art, preferably alkali metal salts are tert-butoxide salt such as Sodium tert-butoxide and/or Potassium t-Butoxide. The base used herein in an amount of molar ratio of generally 1.0 to 1.2, base on the compound in the formula S, for example, 1.0.

Wherein the method to the Cu (I)/1, 3-diarylimidazole salt carbene precursor complex: the monovalent copper salt used herein as would be well known to those skilled in the art, preferably copper halide such as Cu (I) chloride. The monovalent copper salt used herein in an amount of molar ratio of generally 0.9 to 1.2 equivalents, base on the compound represented by the formula S, for example, 1.0 equivalents.

Wherein the method of preparation of the Cu (I)/1, 3-diarylimidazole salt carbene precursor complex: the temperature used herein is room temperature.

Wherein the method of preparation of the Cu (I)/1, 3-diarylimidazole salt carbene precursor complex: the process of the reduction reaction can be monitored by the conventional monitoring method (such as TLC, $^1$H NMR, GC, HPLC) of such reaction as would be well known to those skilled in the art. Generally, the endpoint of the reaction was determined by the 1, 3-diarylimidazole salt carbene precursor that was completely turnover or no longer reacts. The reaction time is preferably 10 to 20 hours, for example, 12 hours.

Wherein the method of preparation of the Cu (I)/1, 3-diarylimidazole salt carbene precursor complex: after the reduction reaction is completed, a workup step may be further included. The workup step is as would be well known to those skilled in the art, and the present invention preferably includes the following workup steps: the solution is filtered with diatomite to remove the solvent (such as concentration under reduced pressure), and purified by column chromatography to obtain the product.

This present invention also provides the crystallography of compound 35: the structure of compound 35 was determined by single-crystal X-ray diffraction spectrum using copper radiation, the crystal belongs to a hexagonal system, the space group was P6$_5$ and the final unit cell parameters were: a=13.6295(3) Å, α=90°, b=13.6295(3) Å, β=90°, c=50.1903(16) Å, γ=120°. The volume of the unit cell (V) was 8074.4(4) Å3, and the number of molecules in the unit cell (Z) was 6.

The crystallography of compound 35 ((R,R,R,R)-ANIPE-CuCl) was shown in table 1.

This present invention also provides methods of the crystallography for compound 35 preferably the following steps, the solution of compound 35 mixed with an ether solvent was filtered after sonication, and then the filtrate was placed under an atmosphere of alkane solvent. The filtering is performed after ultrasound.

This present invention also provides methods of the crystallography for compound 35 preferably the following steps, the solution of compound 35 mixed with an ether solvent was filtered after sonication, then the filtrate was placed under an atmosphere of alkane solvent.

Wherein the methods of the crystallography for compound 35, more details about the filtrate was placed under an atmosphere of alkane solvent, the condition used herein preferably wide-mouth bottle with alkane.

Wherein the methods of the crystallography for compound 35, the ether solvents used herein as would be well known to those skilled in the art, which selected from one or more of the following solvent such as isopropyl ether, methyl tert-butyl ether and diethyl ether, for example, diethyl ether. The ether solvents used herein in a volume mass ratio V/M of generally 0.1-0.5 L/g, base on compound 35, for example, 0.2 L/g.

Wherein the methods of the crystallography for compound 35, the alkane used herein is as would be well known to those skilled in the art, which is selected form n-pentane and/or n-hexane, for example, n-pentane.

Wherein the methods of the crystallography for compound 35, the filtration may be a conventional filtration for performing such operations is as would be well known to those skilled in the art.

Wherein the methods of the crystallography for compound 35, the preparation of the crystallography can further include the following operations: selecting a square crystal under a microscope.

The crystallography parameters:

TABLE 1

The crystallography parameters of compound 35 (R,R,R,R)-ANIPE-CuCl

| Formula | $C_{61}H_{57}ClCuN_2O_{0.50}$ |
|---|---|
| Molecular Weight | 925.07 |
| Temperature | 302.13K |
| Wavelength | 0.71073 Å |
| Crystal System | Hexagon |
| Space Group | P6$_5$ |
| Cell Parameters | a = 13.6295(3), α = 90° |
| | b = 13.6295(3) Å, β = 90° |
| | c = 50.1903(16) Å, γ =120° |
| Unit Cell | 8074.4(4) Å$^3$ |
| Z | 6 |
| Density (Calculated) | 1.141 Mg/m$^3$ |
| Absorption cCoefficient | 0.494 mm$^{-1}$ |
| F(000) | 2922 |
| Size | 0.15 * 0.05 * 0.03 mm$^3$ |
| θ Range | 2.029 to 24.996° |
| Index Range | −15 <= h <= 16, −16 <= k <= 15, −59<= l <= 59 |

TABLE 1-continued

The crystallography parameters of compound 35 (R,R,R,R)-ANIPE-CuCl

| | |
|---|---|
| Diffraction Point Collection | 71066 |
| Independent Diffraction Point | 9450 [R(int) = 0.0614] |
| θ = 24.996° Integrity | 99.7% |
| Maximum and Minimum Transfer | 0.7461 and 0.6745 |
| Refinement Method | Full-matrix least-squares on $F^2$ |
| Goodness of Fit/$F^2$ | 1.042 |
| Final R Index [I > 2sigma(I)] | R1 = 0.0711, wR2 = 0.1880 |
| R Index (All Data) | R1 = 0.0791, wR2 = 0.1982 |
| Independent Structural Parameters | 0.024(5) |
| Extinction Index | n/a |

This present invention also provides the use in the asymmetric catalytic reaction of the copper (I)/NHC, and is preferably the (R,R,R,R)-ANIPE-CuCl (compound 35). The asymmetric catalytic reaction is preferably the hydroboration of unactivated terminal alkenes.

Wherein the hydroboration of unactivated alkenes including the following steps, in the organic solvent, Cu (I)/NHC-catalyzed the hydroboration of unactivated alkenes using diboron reagent in the presence of a base. It is further preferred to include the following steps, a) in the organic solvent, a mixture was formed by Cu (I)/NHC complex with diboron reagent in the presence of a base. b) The mixture formed in step a) reacted with unactivated alkenes in the presence of a proton source.

Wherein the hydroboration of unactivated terminal alkenes, in step a), the organic solvent used herein is as would be well known to those skilled in the art such as low-polarity and non-proton solvent, or which selected from one or more of the following solvent consisting of alkane, arene and ether solvent. The alkane used herein is preferably selected from haloalkane solvent and/or alkane, such as dichloromethane and/or hexane. The arene solvent used herein is preferably selected from benzene and/or toluene. The ether solvent used herein is preferably selected from tetrahydrofuran. The solvents used herein in a volume molar ratio which is as would be well known to those skilled in the art of generally 1 to 5 L/mol preferably, base on the unactivated terminal alkenes, for example, 2 L/mol.

Wherein the hydroboration of unactivated terminal alkenes, in step a), The base used herein is as would be well known to those skilled in the art, preferably alkali metal salts are tert-butoxide salt such as sodium tert-butoxide and/or potassium t-butoxide. The molar ratio of the base and the unactivated terminal alkenes is generally 1.0 to 1.2, for example, 1.5 equivalents.

Wherein the hydroboration of alkenes, in step a), the molar ratio of Cu (I)/NHC and the unactivated alkenes is generally 0.01 to 0.05, for example, 0.02 equivalents.

Wherein the hydroboration of alkenes, in step a), the diboron used herein is as would be well known to those skilled in the art of a diboron, for example,

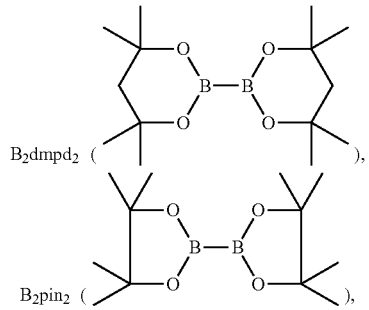

B₂dmpd₂ ( ),

B₂pin₂ ( ),

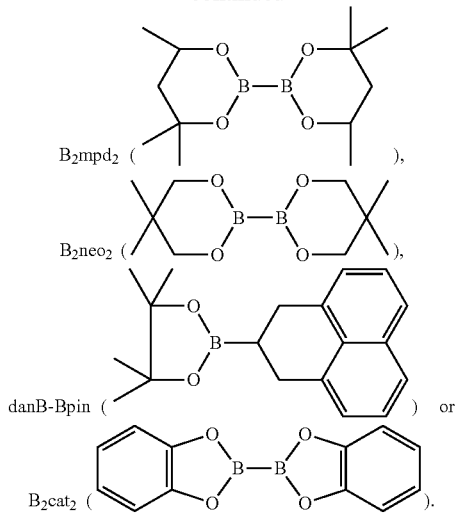

B₂mpd₂ ( ),

B₂neo₂ ( ), danB-Bpin ( ) or

B₂cat₂ ( ).

The molar ratio of diboron and the alkenes is generally 1.5 to 3, for example, 2.0.

Wherein the hydroboration of alkenes, in step a), the temperature used herein is room temperature.

Wherein the hydroboration of alkenes, in step a), after the reaction is completed, a workup step may include the following workup steps: the solution is filtered with diatomite to remove the solvent, and purified by column chromatography to obtain the product.

Wherein the hydroboration of alkenes, in step b), the proton source used herein is as would be well known to those skilled in the art of a conventional proton source, preferably is alcohol which selected from one or more of the following compounds consisting of methanol, ethanol and isopropanol. The molar ratio of proton source and the alkenes is generally 1.5 to 3 equivalents, for example, 2.0 equivalents.

Wherein the hydroboration of unactivated terminal alkenes, in step b), the temperature used herein is room temperature. The room temperature means 0° C. to 35° C., preferably is 20° C. to 30° C.

Wherein this present invention, the alkenes used herein is selected from the following structure:

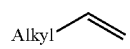

Alkyl

Wherein Alkyl represents substituted or unsubstituted $C_{1-10}$alkyl, the term "$C_{1-10}$alkyl" as used herein is selected from one or more of the following group consisting of halogen, $C_{6-14}$ aryl, substituted $C_{6-14}$ aryl, $C_{1-10}$ alkoxy, substituted $C_{1-10}$alkoxy, —$OR^{p1}$, —$Si(R^{p5})_3$, —$NHC(R^{p6})_3$, $C_{2-12}$heteroaryl, substituted $C_{2-12}$heteroaryl, $C_{3-6}$ cycloalkyl or substituted $C_{3-6}$ cycloalkyl. Wherein $R^{p1}$ is selected from the group consisting of $C_{6-14}$ aryl, substituted $C_{6-14}$ aryl, $C_{2-12}$heteroaryl, substituted $C_{2-12}$heteroaryl or —$SiR^{p4}$. Wherein $R^{p4}$ is selected from the group consisting of $C_{6-14}$ aryl or substituted $C_{6-14}$ aryl. Wherein $R^{p5}$ and $R^{p6}$ are independently or simultaneously selected from the group of $C_{1-4}$alkyl or $C_{6-14}$ aryl.

The term "substituted $C_{6-14}$ aryl", "substituted $C_{1-10}$alkoxy", "substituted $C_{2-12}$ heteroaryl" and "substituted $C_{3-6}$ cycloalkyl" are independently selected from one or more of the following group consisting of halo, cyano, nitro, —COOR$^{p2}$, —C(O)—, C$_{3-6}$ cycloalkyl, substituted C$_{3-6}$ cycloalkyl, C$_{6-14}$ aryl, substituted C$_{6-14}$ aryl or C$_{2-12}$heteroaryl. R$^{p2}$ is selected from H or C$_{1-4}$alkyl. The substituent used herein in the term "substituted C$_{6-14}$ aryl" is selected from one or more of the following group consisting of halo, —SR$^{p3}$, C$_{1-4}$alkyl, halogen-substituted C$_{1-4}$alkyl, C$_{1-4}$alkoxy and halogen-substituted C$_{1-4}$alkoxy. R$^{p3}$ is selected from H or C$_{1-4}$alkyl. Two adjacent substitutions in the substituted C$_{6-14}$ aryl together form a C$_{2-6}$ heterocyclyl based on the carbons to which they are attached. The term "C$_{2-6}$ heterocyclyl" as used herein means 1-4 atoms are a heteroatom selected from the group consisting of N, O and S. The substituent used herein in the term "substituted C$_{3-6}$ cycloalkyl" is selected from one or more of the following group consisting of C$_{6-14}$ aryl or C$_{1-4}$alkyl-substituted C$_{2-12}$heteroaryl.

The term "C$_{2-12}$heteroaryl" as used herein means heteroaryl group containing from 2 to 12 carbon atoms, 1-4 atoms are a heteroatom selected from the group consisting of N, O and S.

In a preferred embodiment of this invention: wherein the Alkyl group, the term "substituted C$_{1-10}$alkyl" as used herein is selected from one or more of the following group consisting of C$_{6-14}$ aryl, substituted C$_{1-10}$ alkoxy, —OR$^{p1}$, —Si(R$^{p5}$)$_3$, —NHC(R$^{p6}$)$_3$, C$_{2-12}$heteroaryl, substituted C$_{2-12}$heteroaryl and substituted C$_{3-6}$cycloalkyl.

In a preferred embodiment of this invention: wherein the substituted group, the term "substituted C$_{1-10}$ alkoxy" as used herein is selected from one or more of the following groups consisting of C$_{6-14}$ aryl, substituted C$_{6-14}$ aryl and C$_{2-12}$heteroaryl. The substituted group in the term "C$_{6-14}$ aryl" as used herein is selected from one or more of the following groups consisting of —SR$^{p3}$, halo-substituted C$_{1-4}$alkyl and halo-substituted C$_{1-4}$alkoxy. Or two adjacent substituents in the substituted C$_{6-14}$ aryl group form a C$_{2-6}$ heterocyclic group based on the connected carbon.

In a preferred embodiment of this invention: wherein the substituted group, the term "substituted C$_{2-12}$heteroaryl" is selected from one or more of the following group consisting of cyano, —COOR$^{p2}$ and —C(O)—.

In a preferred embodiment of this invention: wherein the substituted group, the term "C$_{3-6}$ cycloalkyl" as used herein is selected from one or more of the following groups consisting of C$_{1-4}$alkyl and C$_{6-14}$ aryl.

In a preferred embodiment of this invention: R$^{p1}$ is selected from the following group consisting of C$_{6-14}$aryl, halo-substituted C$_{6-14}$aryl, C$_{2-12}$heteroaryl or —SiR$^{p4}$. R$^{p4}$ means C$_{1-4}$alkyl-substituted C$_{6-14}$aryl.

In a preferred embodiment of this invention: R$^{p3}$ means C$_{1-4}$alkyl.

In a preferred embodiment of this invention: each R$^{p5}$ means C$_{1-4}$alkyl or C$_{6-14}$ aryl.

In a preferred embodiment of this invention: each R$^{p6}$ independently means C$_{6-14}$ aryl.

In a preferred embodiment of this invention: wherein the substituted group, the term "substituted C1-10alkyl" as used herein is selected from one or more of the following group consisting of chlorine, phenyl,

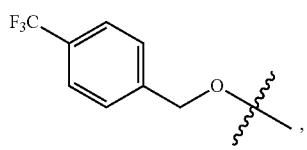

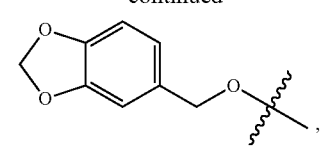

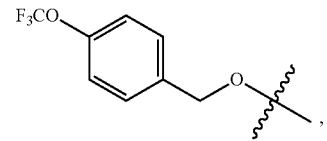

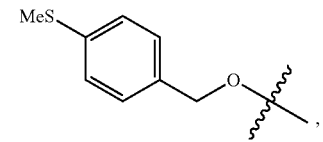

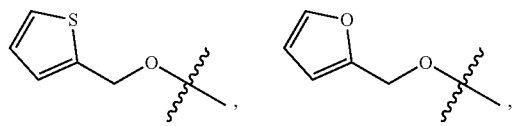

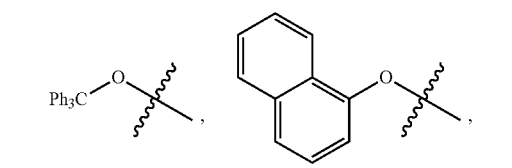

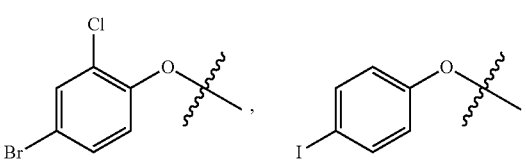

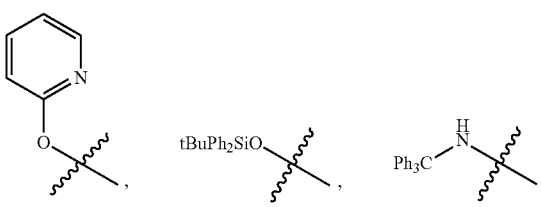

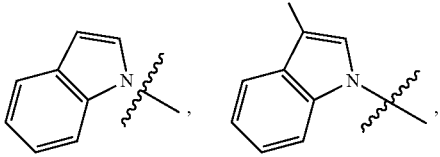

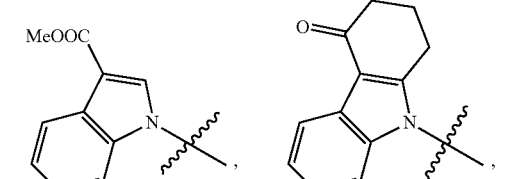

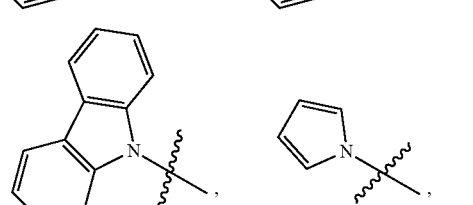

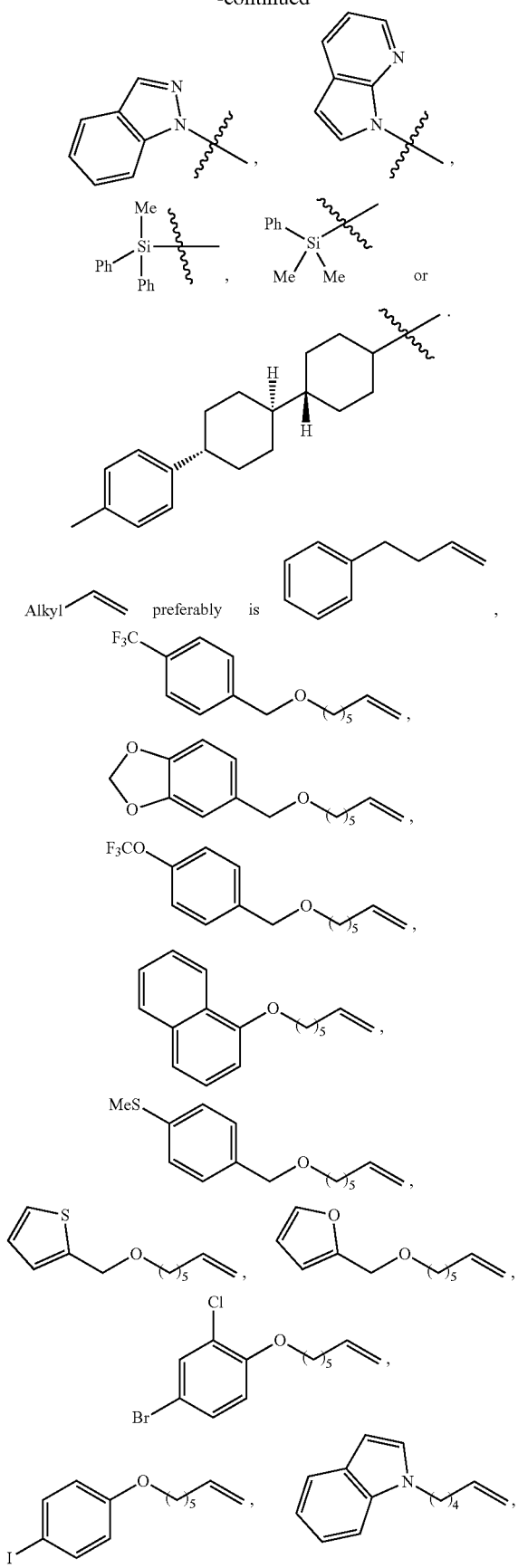
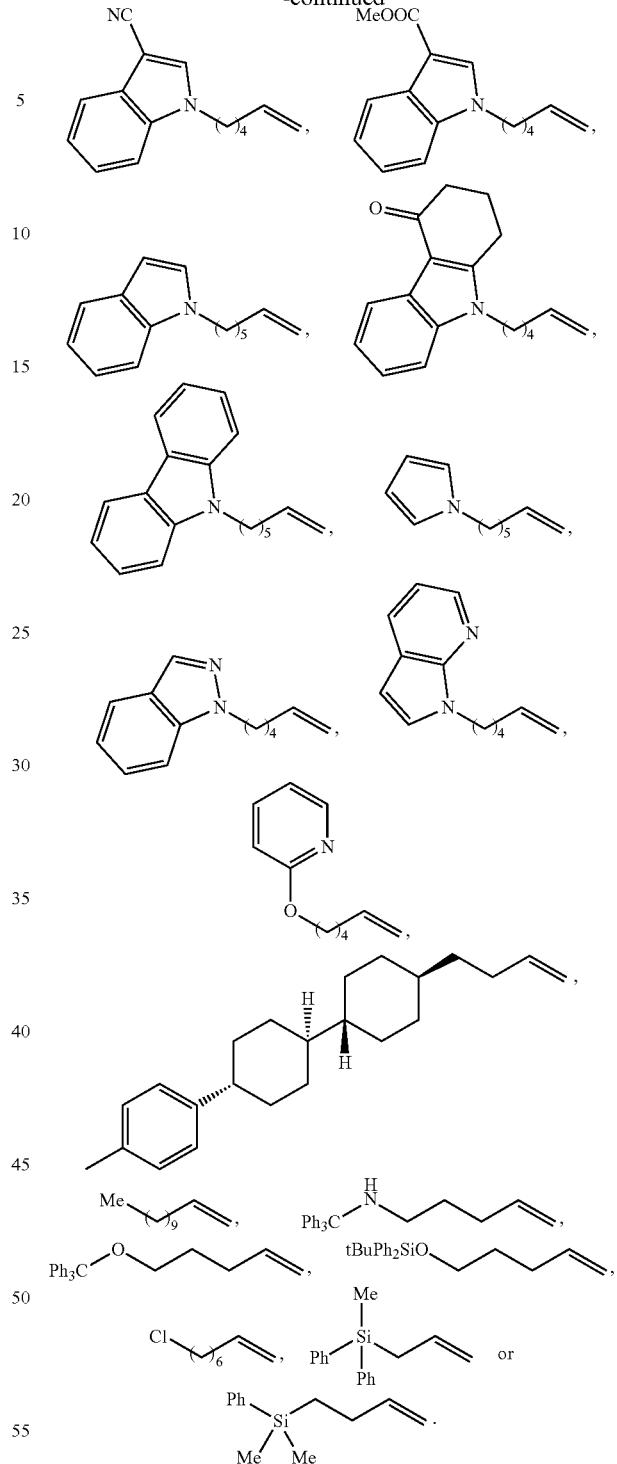

As long as not violating common knowledge in the art, the above-mentioned preferred conditions can be a random combination to obtain preferred embodiments of the present invention.

The reagents and raw materials of the invention are commercially available.

Wherein this invention, the DIPEA used herein means N,N-Diisopropyl-ethylamin. The NBD used herein the (NBD)$_2$RhBF$_4$ means 2,5-norbornadiene. The (Rc, Sp)-Duanphos used herein means (1R,1'R,2S,2'S)-2,2'-Bis(1,1-dimethylethyl)-2,2',3,3'-tetrahydro-1,1'-bi-1H-isophosphindole. The Bdmpd used herein means (2, 4-dimethylpentane-2, 4-glycolato) diboron. The B₂dmpd₂ used herein means bis (2, 4-dimethylpentane-2, 4-glycolato) diboron.

The montmorillonite used herein is a kind of earth like mineral which is composed of a nano thickness of negatively charged silicate flakes on the surface and is accumulated together by the electrostatic action between the layers. The crystal cell in the crystal structure is composed of two layers of silicon-oxygen tetrahedron sandwiched with a layer of aluminum oxygen octahedron, which has a unique one-dimensional layered nanostructure and cation exchange characteristics.

Wherein this invention, the term "halogen" used herein means fluorine, chlorine, bromine, or iodine Wherein this invention, the term "carbonyl" used herein means

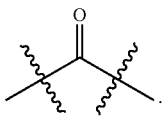 [SMILES: *C(*)=O]

Wherein this invention, the term "alkyl" used herein means saturated aliphatic hydrocarbon with a specified number of carbon atoms in branched or straight chains. For example, the term "$C_{1-4}$ alkyl" as used herein is selected from one or more of the following group consisting of methyl, ethyl, n-propyl, isopropyl, n-butyl, t-butyl or isobutyl. The term "$C_{3-6}$ cycloalkyl" as used herein is selected from one or more of the following groups consisting of cyclopropyl, cyclobutyl, cyclopentyl or cyclohexyl.

Wherein this invention, the term "$C_{1-4}$ alkyl" as used herein means one or more of the hydrogens on the $C_{1-4}$ alkyl was substituted with halogen. When the halogen is multiple, the halogen can be the same or different. The halogen-substituted $C_{1-4}$ alkyl also means —$CF_3$.

Wherein this invention, the term "hydroxyl-substitution $C_{1-4}$ alkyl" as used herein means one or more of the hydrogens on the $C_{1-4}$ alkyl was substituted with hydroxyl.

Wherein this invention, the term "alkoxy" as used herein means The formation group of alkyl group connected with oxygen atom, means

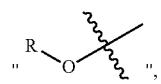

R means alkyl. The term "$C_{1-4}$ alkoxy" as used herein is selected from one or more of the following group consisting of methoxy, ethoxy, propyloxy, isopropoxy, butyloxy, isobutyloxy or tert-butyloxy.

Wherein this invention, the term "heterocyclic" used herein means non-aromatic ring which 1-4 atoms are a heteroatom selected from the group consisting of N, O and S. In this present invention, examples of heterocyclics were shown as following but are not limited to those examples: tetrahydropyranyl, azetidinyl, 1,4-dioxanyl, piperazinyl, piperidinyl, pyrrolidinyl, morpholinyl, thiomorpholinyl, dihydrofuryl, di hydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydro pyridyl, dihydropyrimidyl, dihydropyrrolyl, dihydroquinolinyl, dihydrotetrazolyl, dihydrothiadiazyl, dihydrothiazolyl, dihydrothienyl, dihydrotriazolyl, dihydro azetidine, methylenedioxybenzoyl, tetrahydrofuranyl, tetrahydrothienyl and their N-oxides Wherein this invention, the term "heteroaryl" as used herein means each ring may include up to 15 atoms of stable monocyclic or bicyclic rings, at least one of which is an aromatic ring and contains 1-4 heteroatoms selected from O, N and S. Heteroaryl groups within this definition include but are not limited to following examples: acridinyl, carbazolyl, fluorinyl, quinoxalinyl, pyrazolyl, indolyl, benzotriazolyl, benzopyrazolyl, furyl, thienyl, benzothienyl, benzo Furyl, quinolinyl, isoquinolinyl, oxazolyl, isoxazolyl, pyrrolopyridylpyrazinyl, pyridazinyl, pyridyl, pyrimidinyl, pyrrolyl, tetrahydroquinoline or

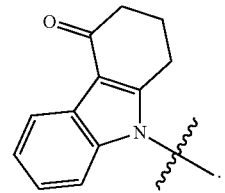 [SMILES: *n1c2c(c3ccccc31)C(=O)CCC2]

Wherein this invention, one or more of the hydrogens on the term "aryl" or "heteroaryl" are further optionally replaced with halo, cyano, nitro, carbonyl, $C_{1-4}$ alkyl, halogen-substituted $C_{1-4}$ alkyl, hydroxy-substituted $C_{1-4}$ alkyl, $C_{1-4}$ alkoxy, $C_{3-6}$ cycloalkyl, $C_{2-6}$ heterocyclic, $C_{6-14}$ aryl, $C_{2-10}$ heteroaryl, carboxyl or

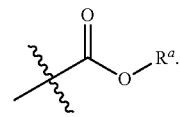

When there are multiple substituents, each substituent may be the same or different. $R^a$ represents $C_{1-4}$ alkyl. The term "$C_{2-6}$ heterocyclic" as used herein means heterocyclic group containing from 2 to 6 carbon atoms, 1-4 atoms are a heteroatom selected from the group consisting of N, O and S. The term "$C_{2-10}$ heteroaryl" as used herein means heteroaryl group containing from 2 to 10 carbon atoms, 1-4 atoms are a heteroatom selected from the group consisting of N, O and S.

The important progress of the invention is as follows: Cu(I)/NHC-catalyzed highly regio- and enantioselective hydroboration of the unactivated terminal alkenes using diboron to give opticaly active alkylboronic esters.

BRIEF DESCRIPTION OF THE DRAWINGS

FIG. 1 is the Single-Crystal Diffraction Patterns of (R,R,R,R)-ANIPE-CuCl (compound 35).

DETAILED DESCRIPTION

Example 1

Synthesis of the 4,5-dimethyl-1,3-bis (4-methyl-2,6-bis ((R)-1-phenylethyl)phenyl)-1H-imidazol-3-ium bromide (7)

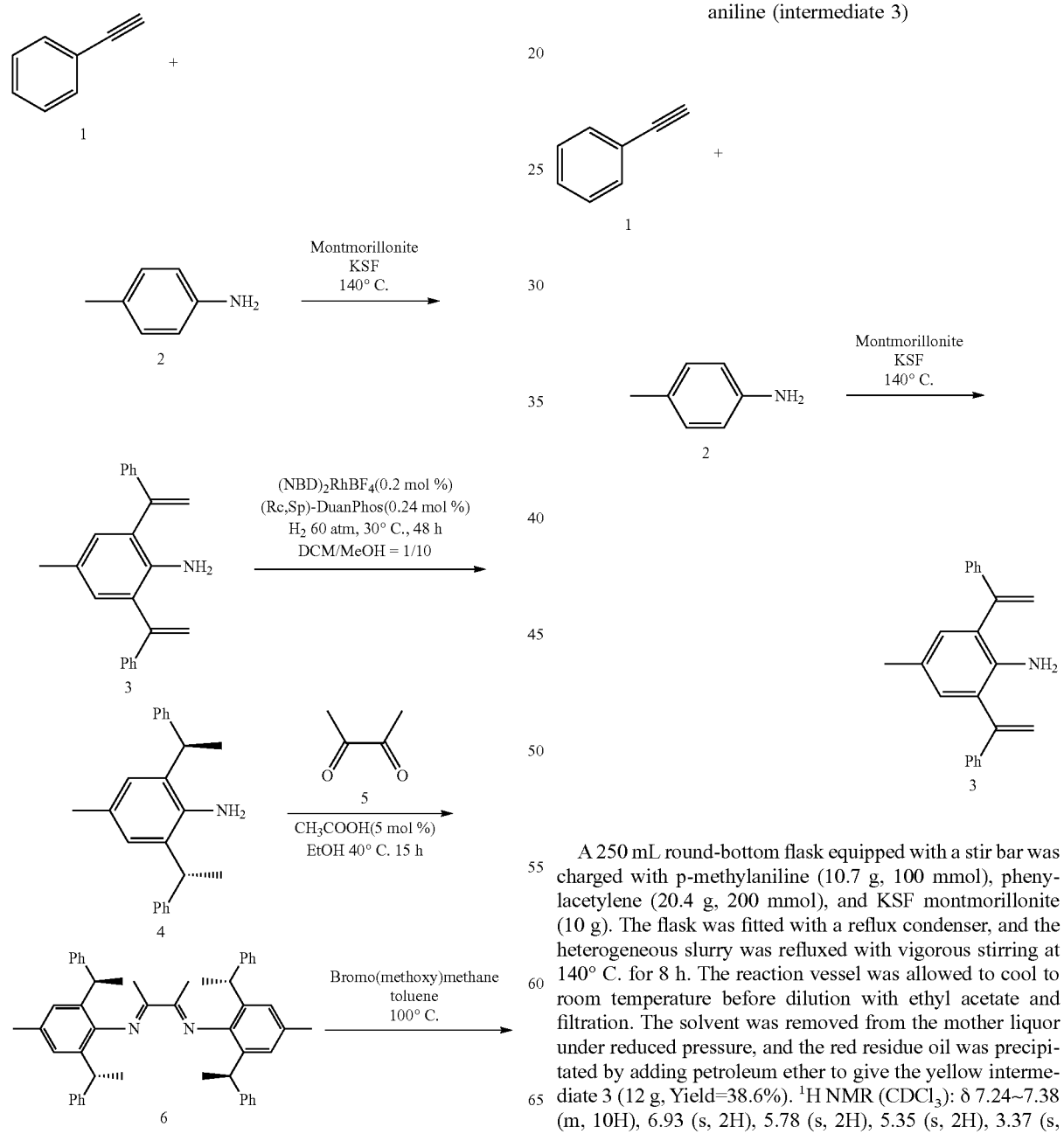

Synthesis of the 4-methyl-2, 6-bis (1-phenylvinyl) aniline (intermediate 3)

A 250 mL round-bottom flask equipped with a stir bar was charged with p-methylaniline (10.7 g, 100 mmol), phenylacetylene (20.4 g, 200 mmol), and KSF montmorillonite (10 g). The flask was fitted with a reflux condenser, and the heterogeneous slurry was refluxed with vigorous stirring at 140° C. for 8 h. The reaction vessel was allowed to cool to room temperature before dilution with ethyl acetate and filtration. The solvent was removed from the mother liquor under reduced pressure, and the red residue oil was precipitated by adding petroleum ether to give the yellow intermediate 3 (12 g, Yield=38.6%). $^1$H NMR (CDCl$_3$): δ 7.24~7.38 (m, 10H), 6.93 (s, 2H), 5.78 (s, 2H), 5.35 (s, 2H), 3.37 (s, 2H), 2.26 (s, 3H).

Synthesis of the 4-methyl-2, 6-bis ((R)-1-phenyl-ethyl) aniline (intermediate 4)

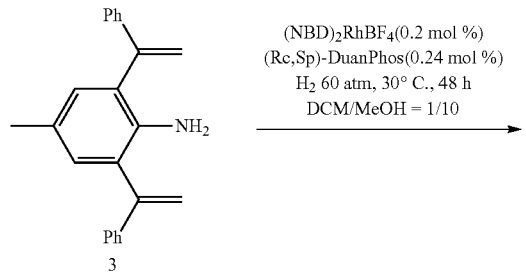

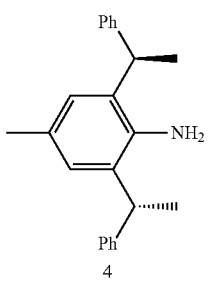

In a 1 L microwave tube, (NBD)$_2$RhBF$_4$ (0.2 mol %) and (Rc, Sp)-DuanPhos (0.24 mol %) were dissolved in 40 mL DCM under a nitrogen atmosphere and stirred for 15 min. A solution of intermediate 3 (1.0 equiv) in a minimal amount of DCM was added. Subsequently 400 mL MeOH was added. The microwave tube was transferred into the autoclave and the reactor was purged three times with H$_2$. The reactor was pressurized to 60 bar H$_2$ and the mixture was stirred at ambient temperature for 48 h. The reaction mixture was suction filtered, washed with methanol, and the solid was recrystallized from methanol to afford the desired chiral white intermediate 4 (45 g, Yield=89%). $^1$H NMR (CDCl$_3$): δ 7.13~7.27 (m, 10H), 6.06 (s, 2H), 3.98 (q, J=8.0 Hz, 2H), 3.22 (s, 2H), 2.37 (s, 3H), 1.59 (d, J=8.0 Hz, 6H).

Synthesis of the (2E, 3E)-N$^2$, N$^3$-bis (4-methyl-2, 6-bis ((R)-1-phenylethyl)phenyl) butane-2, 3-diimine (intermediate 6)

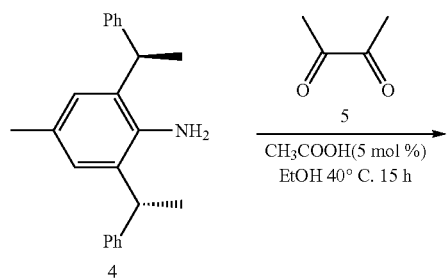

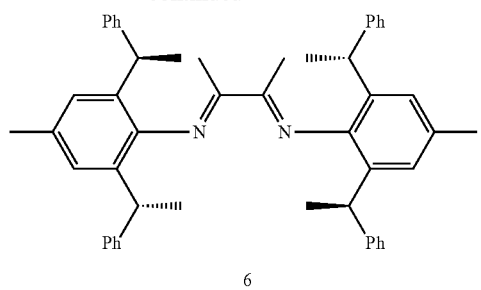

A 100 mL round-bottom flask equipped with a stir bar was charged with 4-methyl-2, 6-bis ((R)-1-phenylethyl) aniline intermediate 4 (3 g, 9.52 mmol), 50 mL ethanol and 2, 3-butanedione 5 (432 mg, 4.76 mmol), CH$_3$COOH (5 mol %), and the mixture was heated with vigorous stirring at 40° C. for 15 h. The reaction mixture was suction filtered, washed with ethanol, and dry to afford intermediate 6 (2.79 g, Yield=87%).

Synthesis of the 4, 5-dimethyl-1, 3-bis (4-methyl-2, 6-bis ((R)-1-phenylethyl)phenyl)-1H-imidazol-3-ium bromide (7)

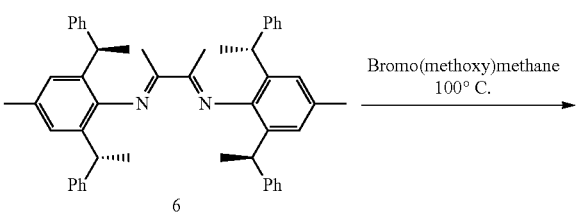

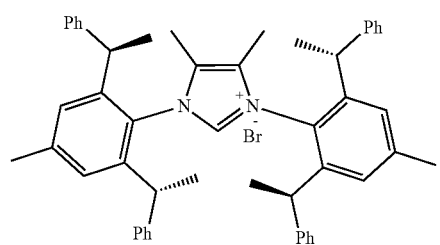

A 100 mL round-bottom flask equipped with a stir bar was charged with intermediate 6 (1.366 g, 2 mmol), bromomethyl ether (5 g, 40 mmol), and the mixture was heated with vigorous stirring at 100° C. for 12 h. The reaction mixture was adding ether to precipitate a white solid, suction filtered, washed with ether, and dry to afford compound 7. $^1$H NMR (400 MHz, CDCl$_3$) δ: 10.31 (s, 1H), 7.53 (s, 2H), 7.37 (s, 2H), 7.28-7.15 (m, 10H), 7.09 (s, 6H), 6.89 (s, 2H), 6.69 (d, J=6.6 Hz, 2H), 3.45 (d, J=7.5 Hz, 2H), 3.32 (d, J=6.6 Hz, 2H), 2.58 (s, 6H), 2.30 (s, 6H), 1.56 (d, J=6.4 Hz, 12H).

Example 2

Synthesis of the 1,3-bis(4-methyl-2,6-bis((R)-1-phenylethyl)phenyl)-3,4,5,6-tetrahydropyrimidin-1-ium iodide (compound 11)

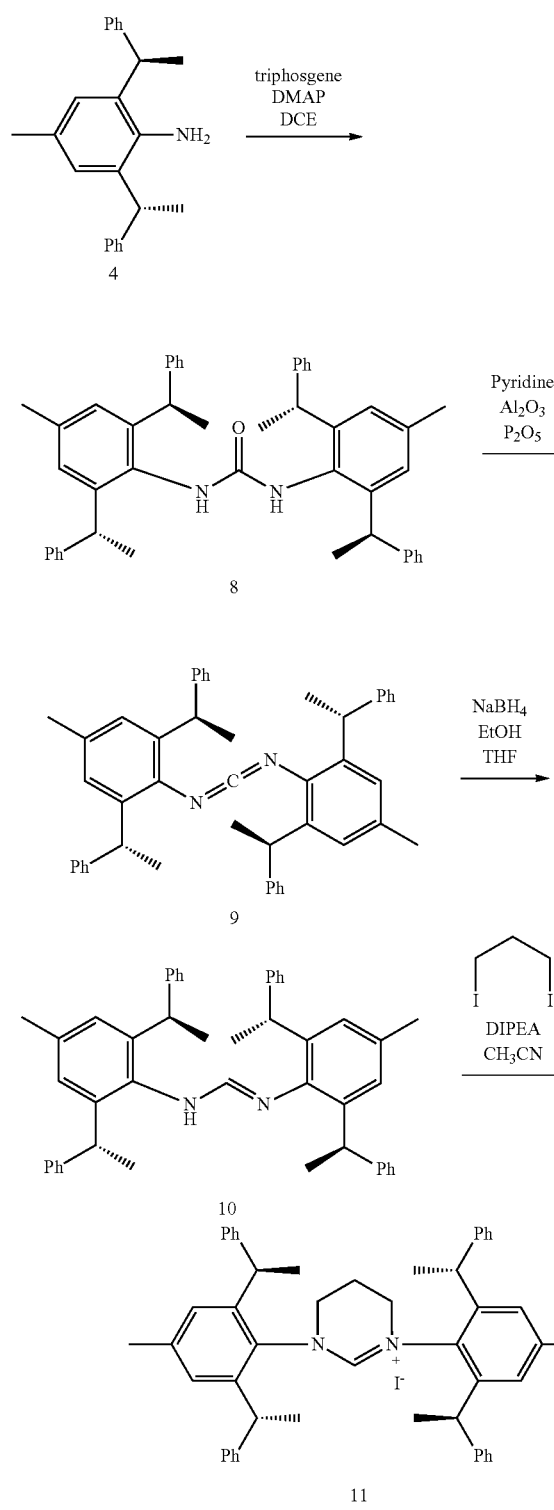

Synthesis of the 1, 3-bis (4-methyl-2, 6-bis ((R)-1-phenylethyl)phenyl) urea (intermediate 8)

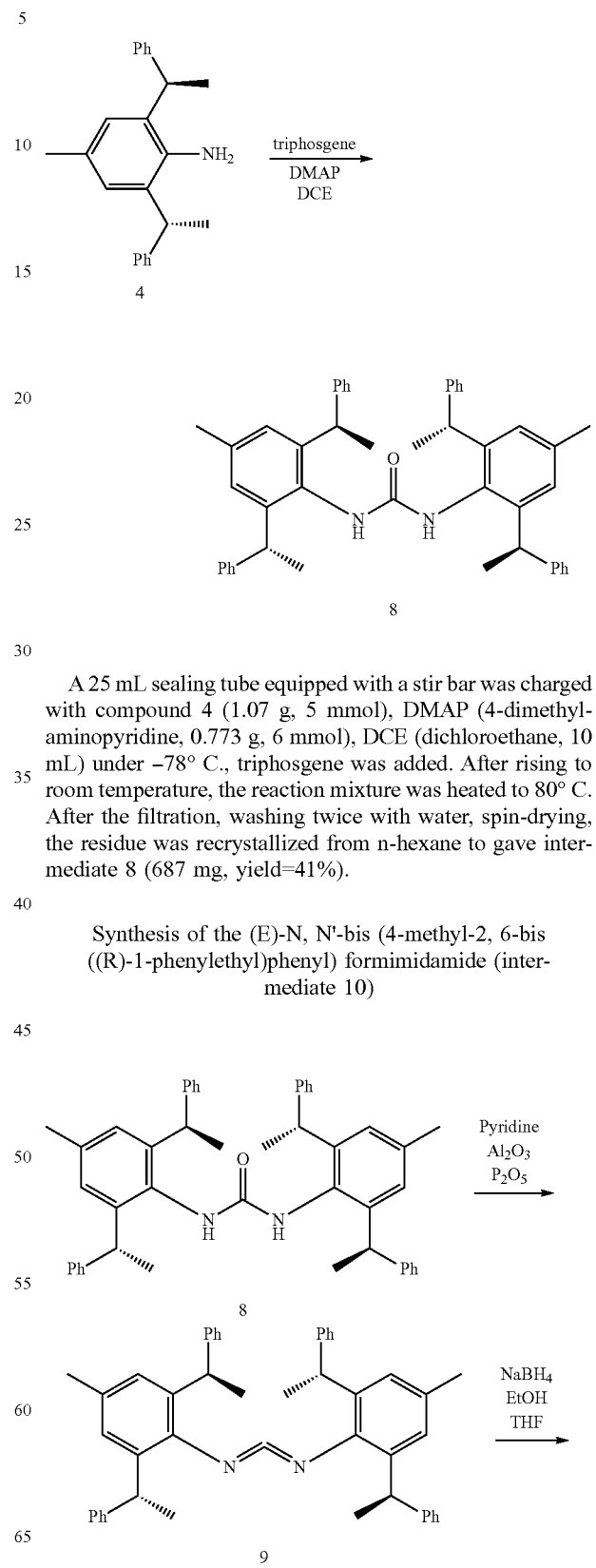

A 25 mL sealing tube equipped with a stir bar was charged with compound 4 (1.07 g, 5 mmol), DMAP (4-dimethylaminopyridine, 0.773 g, 6 mmol), DCE (dichloroethane, 10 mL) under −78° C., triphosgene was added. After rising to room temperature, the reaction mixture was heated to 80° C. After the filtration, washing twice with water, spin-drying, the residue was recrystallized from n-hexane to gave intermediate 8 (687 mg, yield=41%).

Synthesis of the (E)-N, N'-bis (4-methyl-2, 6-bis ((R)-1-phenylethyl)phenyl) formimidamide (intermediate 10)

-continued

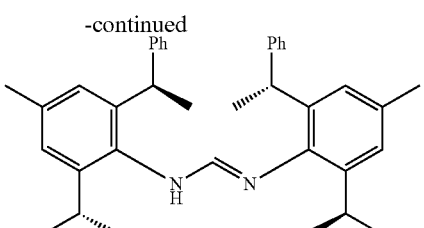

10

A 25 mL sealing tube equipped with a stir bar was charged with compound 8 (678 mg, 1 mmol), pyridine (13 mL), aluminum oxide (1.2 g, 12 mmol), phosphorus pentoxide (2 g, 14 mmol), and the mixture was vigorous stirring at room temperature. Mixture caking, filtration and washing, spin-drying to give compound 9 as a solid which direct use for the next step.

To compound 9 was added ethanol (12 mL), tetrahydrofuran (6 mL), and sodium borohydride (32 mg, 0.8 mmol). The mixture was vigorous stirring at room temperature for 1 h. After adding an appropriate amount of water, extraction with ethyl acetate, combining with the organic phase, spin-dry, the residue was purified by column chromatography to give the white solid compound 10 (348 mg, Yield=50%).

Synthesis of the 1,3-bis(4-methyl-2,6-bis((R)-1-phenylethyl)phenyl)-3,4,5,6-tetrahydropyrimidin-1-ium iodide (compound 11)

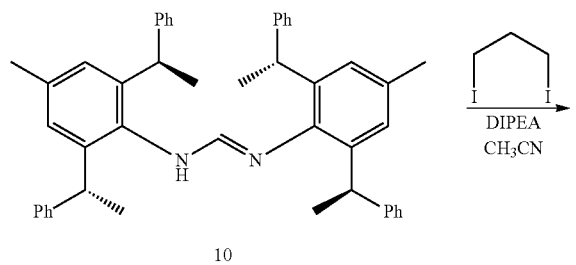

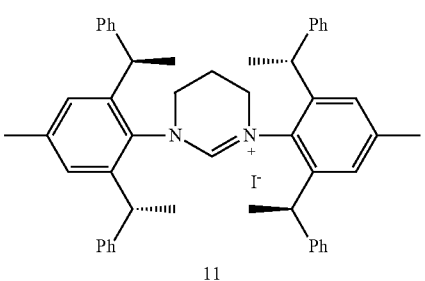

The compound 10 (65 mg, 0.1 mmol), 1, 3-diiodopropane (88.8 mg, 0.3 mmol), DIPEA (N, N-Diisopropylethylamine, 20 uL), acetonitrile (150 uL) were charged to an 8 ml vial equipped with a magnetic stirrer bar. The reaction mixture was allowed to stir at 80° C. for 12 h, dried in vacuo before the DCM was added, washing with saturated potassium carbonate, spin-dry to a solid, and the resultant solid was washed by adding ether to gave the white compound 11 (40 mg, Yield=38%). $^1$H NMR (400 MHz, CDCl$_3$) δ 8.46 (s, 1H), 7.31 (d, J=6.8 Hz, 9H), 7.26-7.18 (m, 7H), 7.15 (s, 5H), 6.96 (s, 2H), 6.76 (d, J=7.4 Hz, 4H), 4.29 (d, J=6.5 Hz, 2H), 3.75 (d, J=6.4 Hz, 2H), 3.55-3.43 (m, 2H), 2.82 (d, J=7.5 Hz, 2H), 2.35 (s, 7H), 1.78 (d, J=6.9 Hz, 9H), 1.14 (d, J=6.7 Hz, 6H).

Example 3

1, 3-Bis (4-methyl-2, 6-bis(-1-phenylethyl)phenyl)-4, 5-dihydro-1H-3-imidazolium chloride (compound 16)

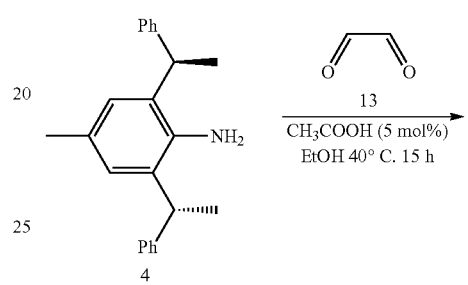

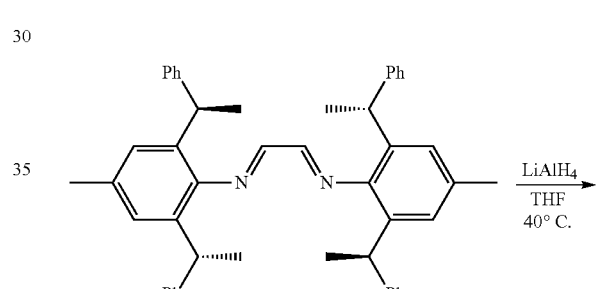

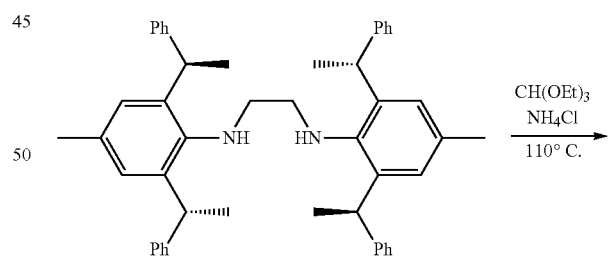

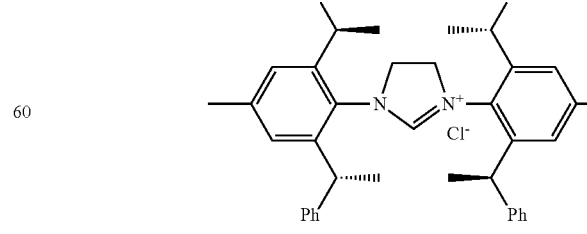

Synthesis of the (1E, 2E)-N$^1$, N$^2$-bis (4-methyl-2, 6-bis ((R)-1-phenylethyl)phenyl) ethane-1, 2-diimine (intermediate 14)

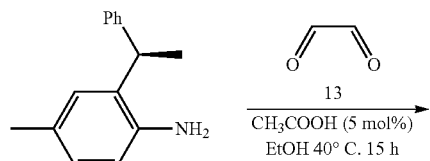

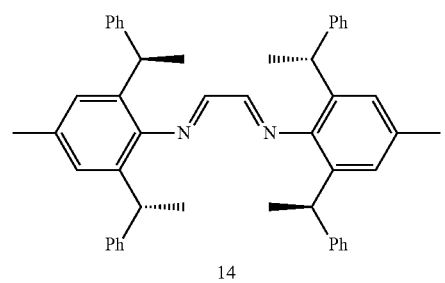

A 100 mL round-bottom flask equipped with a stir bar was charged with intermediate 4 (3 g, 9.52 mmol) was suspended in 50 mL EtOH and heated under reflux for 1 h. Drops of acetic acid (5 mol %) was then added and reflux was continued. A 40% solution of glyoxal (691 mg, 4.76 mmol) in water was added with the aid of a dropping funnel over a period of 30 min, and the resulting mixture was heated at 40° C. for further 15 h and then cooled to room temperature. The crude product was filtered, washed with EtOH and dried in vacuo to afford the intermediate 14 as a yellow solid (2.86 g, Yield=92.1%). $^1$HNMR (CDCl$_3$): δ7.65 (s, 2H), 7.11-7.22 (m, 20H), 6.92 (s, 4H), 4.02 (q, 0.1=8.0 Hz, 4H), 3.28 (s, 6H), 1.52 (d, 0.1=4.0 Hz, 12H).

Synthesis of the N, N'-Bis (4-methyl-2, 6-bis ((R)-1-phenylethyl)phenyl) ethane-1, 2-diamine (intermediate 15)

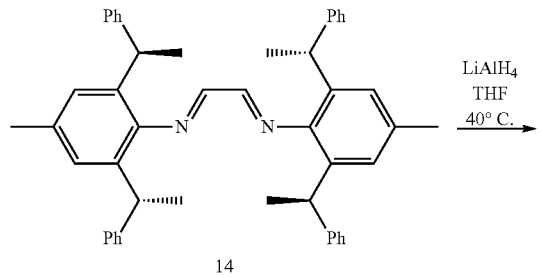

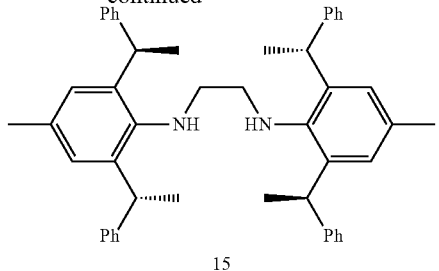

A 100 mL round-bottom flask equipped with a stir bar was charged with compound 14 (2.86 g, 4.38 mmol), LiAlH$_4$ (499 mg, 13.14 mmol) was suspended in 30 mL THF under a nitrogen atmosphere. The mixture was stirred at 40° C. for 12 h. Saturated KOH solution was added, and the mixture was extracted with EA for three times, combined organic layer and dried over Na$_2$SO$_4$. The crude product obtained after filtration and concentration in vacuo was purified by column chromatography to afford the title product compound 15 (2.82 g, Yield=98%). $^1$H NMR (CDCl$_3$): δ 7.09~7.15 (m, 20H), 6.90 (s, 4H), 4.37 (q, 0.1=8.0 Hz, 4H), 2.87 (s, 2H), 2.72 (d, J=8.0 Hz, 2H), 2.49 (d, J=8.0 Hz, 2H), 2.26 (s, 6H), 1.53 (s, 12H).

Synthesis of the 1, 3-Bis (4-methyl-2, 6-bis ((R)-1-phenylethyl)phenyl)-4, 5-dihydro-1H-3-imidazolium chloride (compound 16)

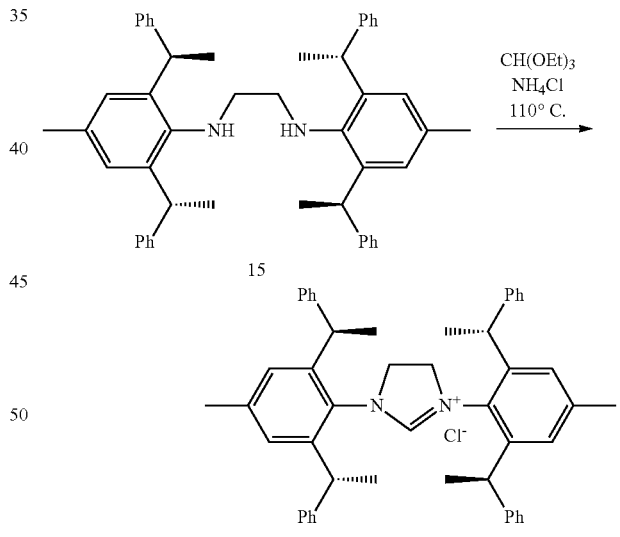

A 100 mL round-bottom flask equipped with a stir bar was charged with compound 15 (2.82 g, 4.29 mmol) and NH$_4$Cl (344 mg, 6.4 mmol) were dissolved in 20 mL HC (OEt) 3 under a nitrogen atmosphere. The mixture was stirred at 110° C. for 18 h and then cooled to room temperature. The crude product was filtered, washed with Et$_2$O and dried in vacuo to afford the saturated imidazolium salt as a white solid compound 16 (1.81 g, Yield=60%). $^1$H NMR (400 MHz, CDCl$_3$) δ 10.32 (s, 1H), 7.38 (d, J=6.5 Hz, 3H), 7.23-7.13 (m, 4H), 6.97-6.88 (m, 3H), 4.42-4.31 (m, 1H), 4.26 (dd, J=12.9, 6.4 Hz, 1H), 3.68 (t, J=11.5 Hz, 1H), 3.03 (t, J=13.0 Hz, 1H), 2.34 (s, 3H), 1.73 (d, J=7.3 Hz, 3H), 1.44 (d, J=7.1 Hz, 3H).

Example 4

Synthesis of the 1, 3-Bis (4-methoxy-2, 6-bis ((R)-1-phenylethyl) phenyl)-4, 5-dihydro-1H-3-imidazolium chloride (compound 22)

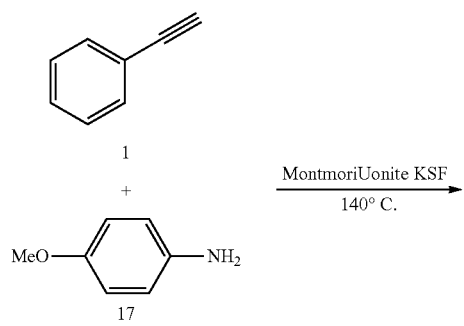

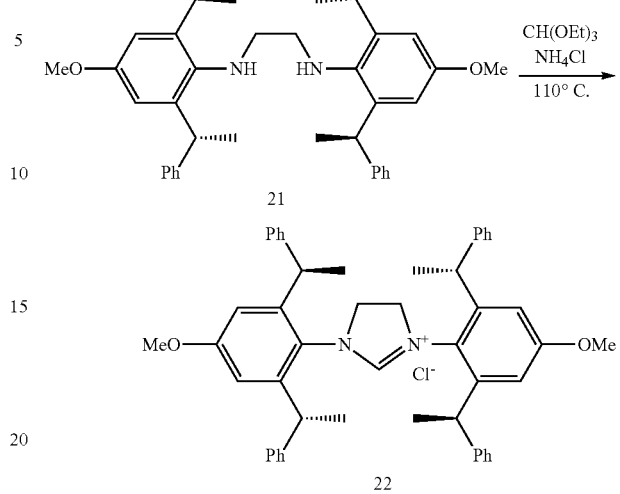

Synthesis of the 4-Methoxy-2, 6-bis (1-phenylvinyl) aniline (intermediate 18)

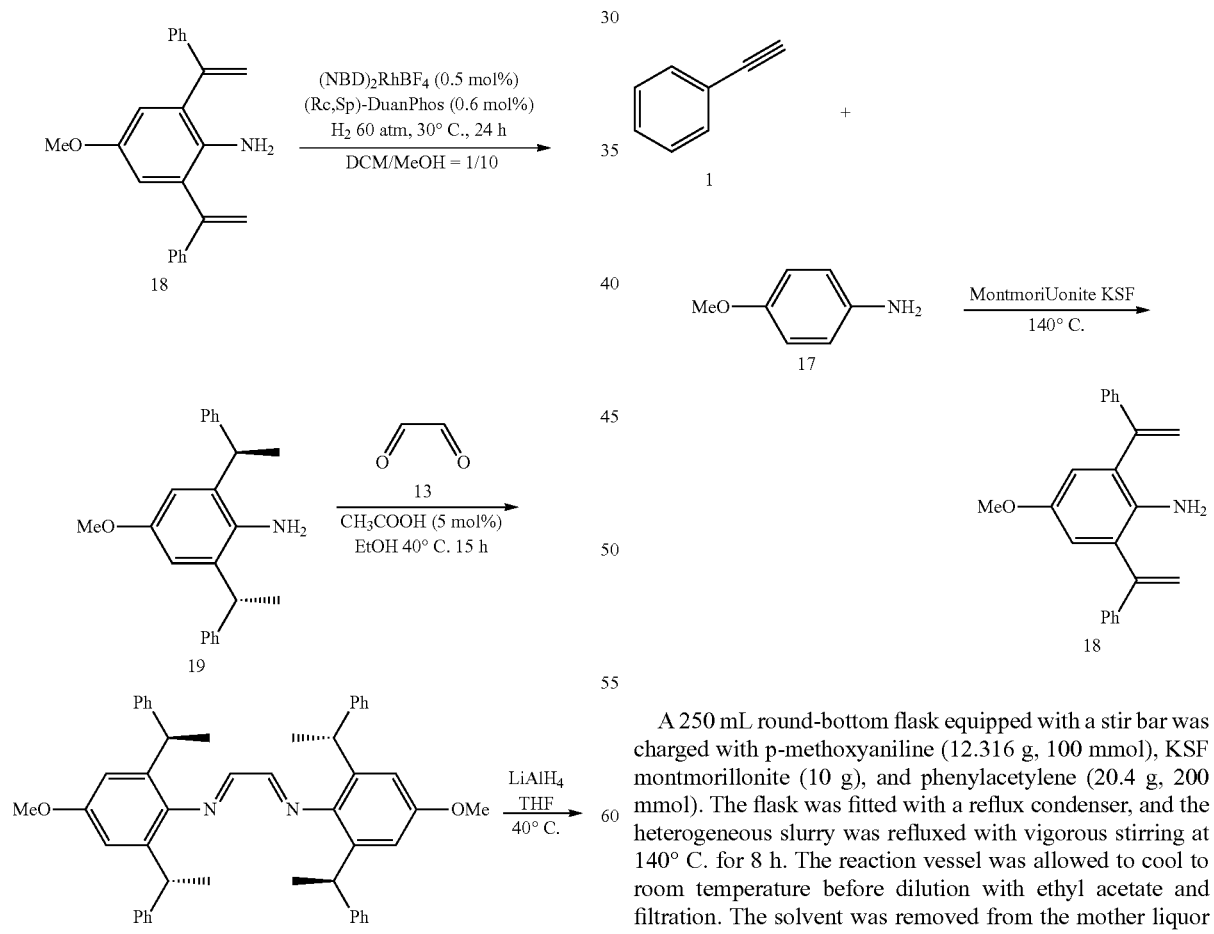

A 250 mL round-bottom flask equipped with a stir bar was charged with p-methoxyaniline (12.316 g, 100 mmol), KSF montmorillonite (10 g), and phenylacetylene (20.4 g, 200 mmol). The flask was fitted with a reflux condenser, and the heterogeneous slurry was refluxed with vigorous stirring at 140° C. for 8 h. The reaction vessel was allowed to cool to room temperature before dilution with ethyl acetate and filtration. The solvent was removed from the mother liquor under reduced pressure, and the residue was purified by adding petroleum ether to give intermediate 18 (10.7 g, Yield=32.7%).

Synthesis of the 4-Methoxy-2, 6-bis ((R)-1-phenyl-ethyl) aniline (intermediate 19)

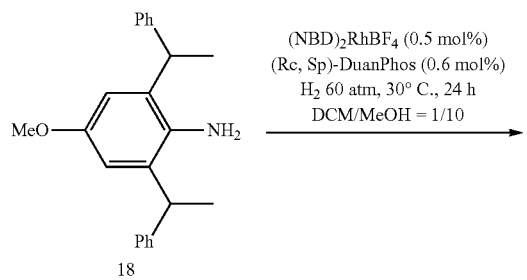

In a 100 mL microwave tube, (NBD)$_2$RhBF$_4$ (0.5 mol %) and (Rc,Sp)-DuanPhos (0.6 mol %) were dissolved in 10 mL DCM under a nitrogen atmosphere and stirred for 15 min. A solution of intermediate 18 (7.36 g, 22.51 mmol) in a minimal amount of 60 mL MeOH was added. The microwave tube was transferred into the autoclave and the reactor was purged three times with H$_2$. The reactor was pressurized to 60 bar H$_2$ and the mixture was stirred at ambient temperature for 24 h. The reaction mixture was suction filtered, washed with methanol, and the solid was recrystallized from methanol to afford the desired chiral white intermediate 19 (4.62 g, Yield=62%).

Synthesis of the (1E, 2E)-N$^1$, N$^2$-Bis (4-methoxy-2, 6-bis ((R) 1-phenylethyl) phenyl) ethane-1, 2-di-amine (intermediate 20)

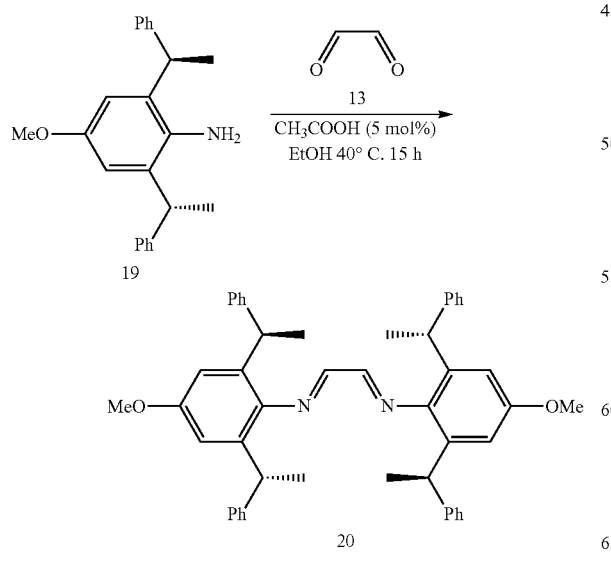

A 100 mL round-bottom flask equipped with a stir bar was charged with intermediate 19 (3.15 g, 9.52 mmol) was suspended in 50 mL EtOH and heated under reflux for 1 h. Drops of acetic acid (5 mol %) was then added and reflux was continued. A 40% solution of glyoxal (691 mg, 4.76 mmol) in water was added with the aid of a dropping funnel over a period of 30 min, and the resulting mixture was heated at 40° C. for further 15 h and then cooled to room temperature. The crude product was filtered, washed with EtOH and dried in vacuo to afford the intermediate 20 as a yellow solid (2.87 g, Yield=88.1%).

Synthesis of the N$^1$, N$^2$-bis (4-methoxy-2, 6-bis ((R)-1-phenylethyl) phenyl) ethane-1, 2-diamine (intermediate 21)

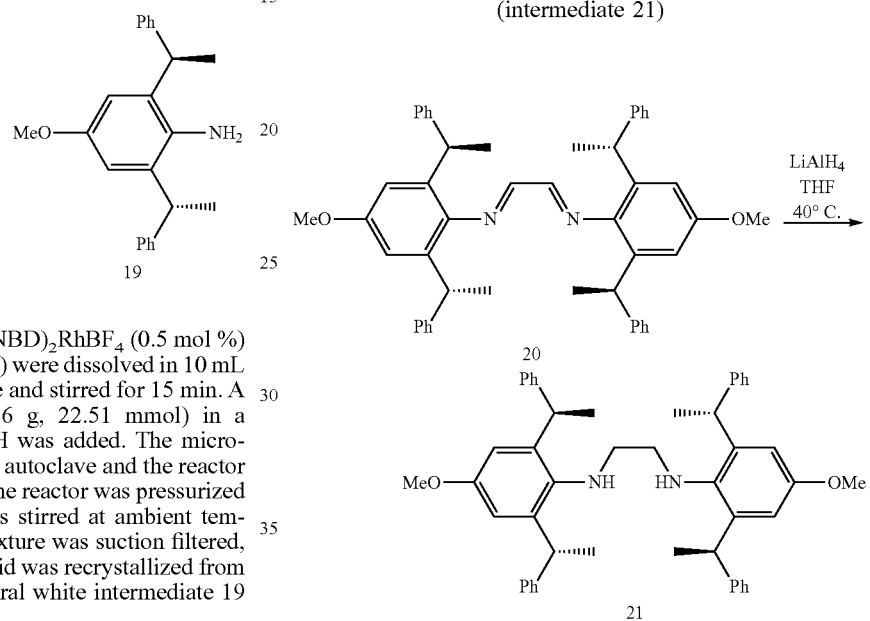

A 100 mL flask equipped with a stir bar was charged with compound 20 (3 g, 4.38 mmol), LiAlH$_4$ (499 mg, 13.14 mmol), and 30 mL THF under a nitrogen atmosphere. The mixture was stirred at 40° C. for 12 h. Saturated KOH solution was carefully added, and the mixture was extracted with EA, combined organic layer and dried over Na$_2$SO$_4$. The crude product obtained after filtration and concentration in vacuo was purified by column chromatography to afford intermediate 21 (2.65 g, Yield=88%).

Synthesis of the 1,3-Bis (4-methoxy-2,6-bis ((R)-1-phenylethyl)phenyl)-4,5-dihydro-1H-3-imidazolium chloride (compound 22)

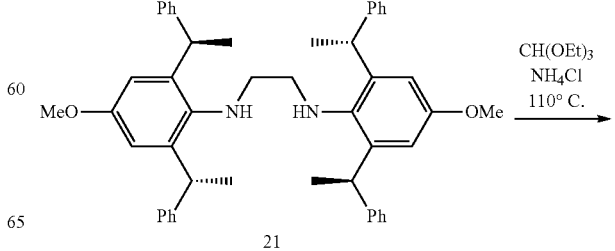

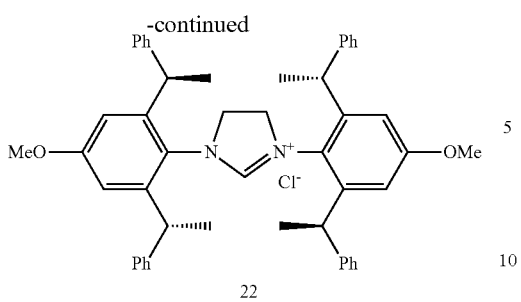

22

To a 100 mL flask equipped with a stir bar was added intermediate 21 (2.95 g, 4.29 mmol), NE$_4$Cl (344 mg, 6.4 mmol), and 20 mL HC(OEt)$_3$ under a nitrogen atmosphere. The mixture was stirred at 110° C. for 18 h and then cooled to room temperature. The crude product was filtered, washed with Et$_2$O and dried in vacuo to afford compound 22 as a white solid (2.015 g, Yield=64%). $^1$H NMR (400 MHz, CDCl$_3$) δ 9.96 (s, 1H), 7.40-7.32 (m, 8H), 7.20 (t, J=7.3 Hz, 6H), 7.14 (t, J=7.2 Hz, 2H), 6.94 (s, 3H), 6.89 (d, J=2.8 Hz, 2H), 6.63 (d, J=2.8 Hz, 2H), 4.37 (q, J=7.1 Hz, 2H), 4.22 (q, J=6.8 Hz, 2H), 3.77 (s, 6H), 3.74-3.54 (m, 2H), 3.19-2.82 (m, 2H), 1.74 (t, J=10.3 Hz, 9H), 1.44 (d, J=7.0 Hz, 6H).

Example 5

Synthesis of the 7,9-bis(4-methyl-2,6-bis((R)-1-phenylethyl)phenyl)-7H-acenaphtho[1,2-d]imidazol-9-ium chloride (compound 25)

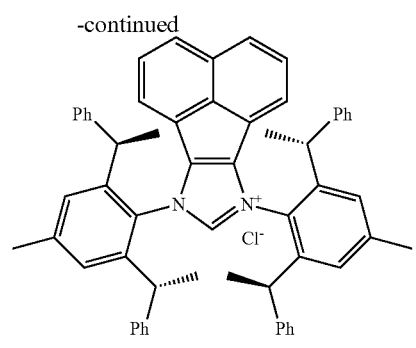

25

Synthesis of the (1E, 2E)-N$^1$, N$^2$-bis (4-methyl-2, 6-bis ((R)-1-phenylethyl)phenyl) acenaphthylene-1, 2-diimine (intermediate 24)

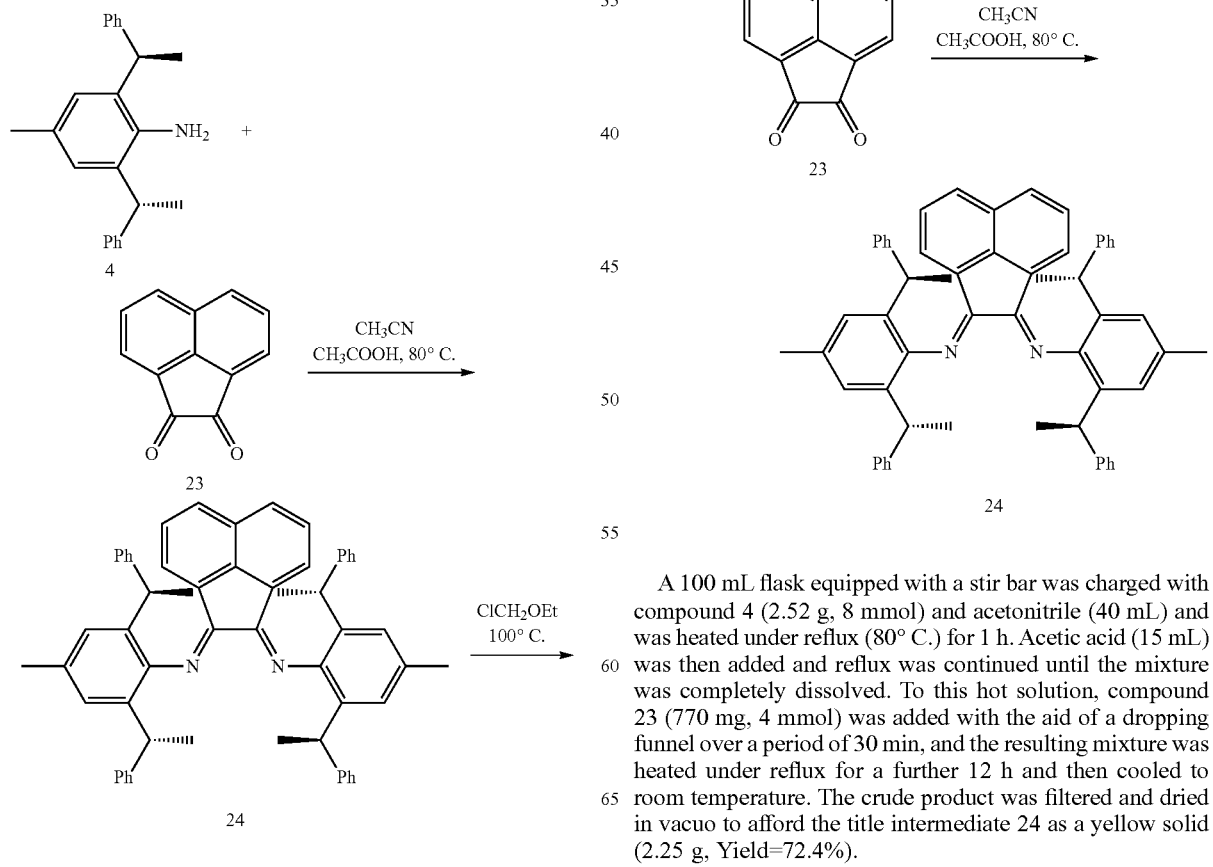

A 100 mL flask equipped with a stir bar was charged with compound 4 (2.52 g, 8 mmol) and acetonitrile (40 mL) and was heated under reflux (80° C.) for 1 h. Acetic acid (15 mL) was then added and reflux was continued until the mixture was completely dissolved. To this hot solution, compound 23 (770 mg, 4 mmol) was added with the aid of a dropping funnel over a period of 30 min, and the resulting mixture was heated under reflux for a further 12 h and then cooled to room temperature. The crude product was filtered and dried in vacuo to afford the title intermediate 24 as a yellow solid (2.25 g, Yield=72.4%).

Synthesis of the 7,9-bis(4-methyl-2,6-bis((R)-1-phenylethyl)phenyl)-7H-acenaphtho[1,2-d]imidazol-9-ium chloride (compound 25)

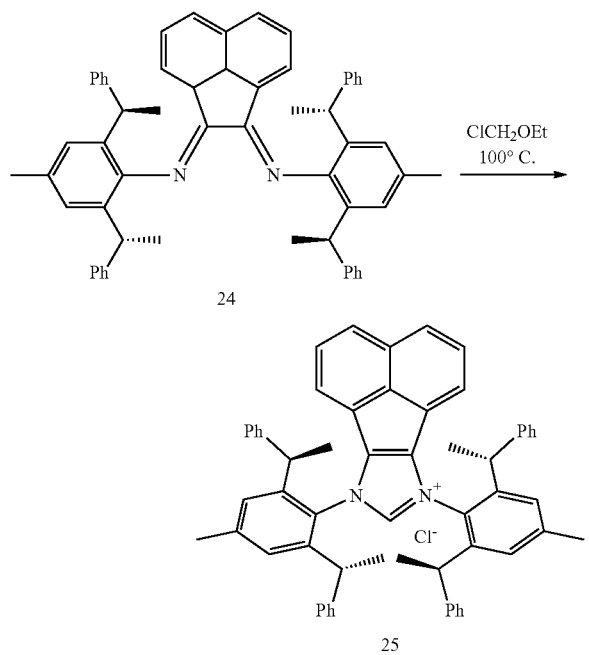

Compound 24 (1.5 g, 1.93 mmol) and chloromethyl ethyl ether (3.65 g, 38.61 mmol) were added to a nitrogen-flushed thick-walled reaction vessel. The vessel was sealed and the reaction mixture was stirred at 80° C. for 24 h. The reaction mixture was cooled to ambient temperature and the resulting solid was filtered to afford the title compound 25 as a pale yellow solid (1.2 g, Yield=75.5%), $^1$H NMR (400 MHz, CDCl$_3$) δ 10.87 (s, 1H), 7.78 (d, J=8.2 Hz, 2H), 7.42-7.22 (m, 12H), 7.17 (s, 2H), 7.06 (s, 2H), 6.71 (d, J=7.0 Hz, 2H), 6.63-6.41 (m, 10H), 4.03 (dd, 0.1=13.5, 6.6 Hz, 2H), 3.70 (d, 0.1=6.2 Hz, 3H), 2.44 (s, 6H), 1.51 (d, 0.1=7.0 Hz, 6H), 1.37 (d, J=6.4 Hz, 6H).

Example 6

Synthesis of the 1,6-dimethyl-7,9-bis(4-methyl-2,6-bis((R)-1-phenylethyl)phenyl)-7H-acenaphtho[1,2-d]imidazol-9-ium bromide (compound 28)

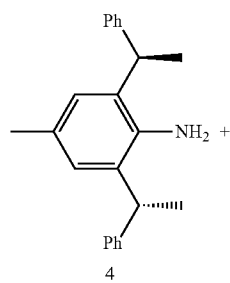

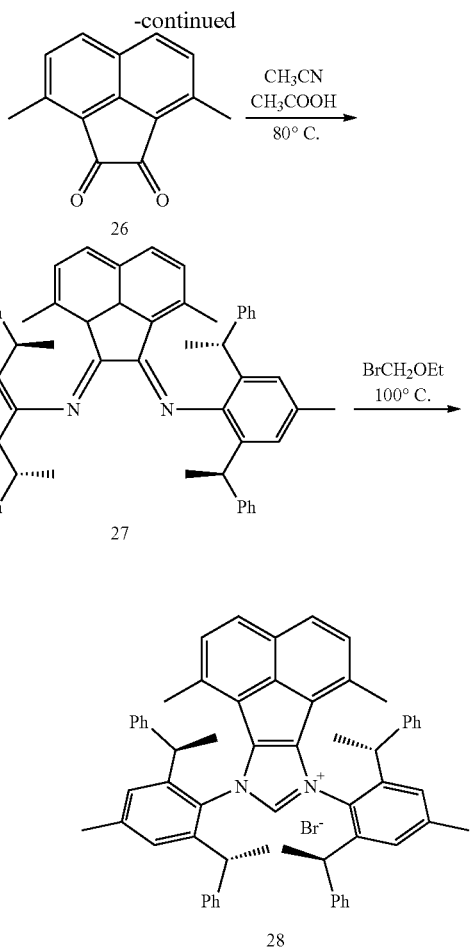

Synthesis of the (1E,2E)-3,8-dimethyl-N$_1$,N$_2$-bis(4-methyl-2,6-bis((R)-1-phenylethyl)phenyl)acenaphth-ylene-1,2-diimine (intermediate 27)

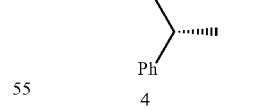

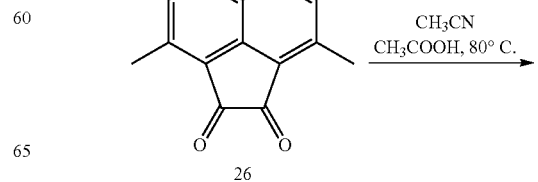

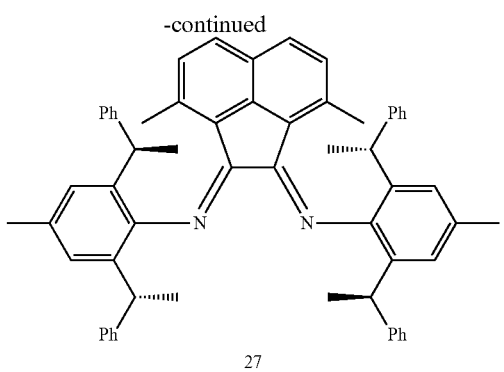

27

A 100 mL flask equipped with a stir bar was charged with intermediate 4 (661 mg, 2.1 mmol) and acetonitrile (20 mL) and was heated under reflux (80° C.) for 1 h. Acetic acid (7 mL) was then added and reflux was continued until the mixture was completely dissolved. To this hot solution, compound 26 (200 mg, 0.95 mmol) was added, and the resulting mixture was heated under reflux for a further 36 h and then cooled to room temperature. The crude product was filtered and dried in vacuo to afford compound 27 as a purple solid (515 mg, Yield=67.4%).

Synthesis of the 1,6-dimethyl-7,9-bis(4-methyl-2,6-bis((R)-1-phenylethyl)phenyl)-7H-acenaphtho[1,2-d]imidazol-9-ium bromide (compound 28)

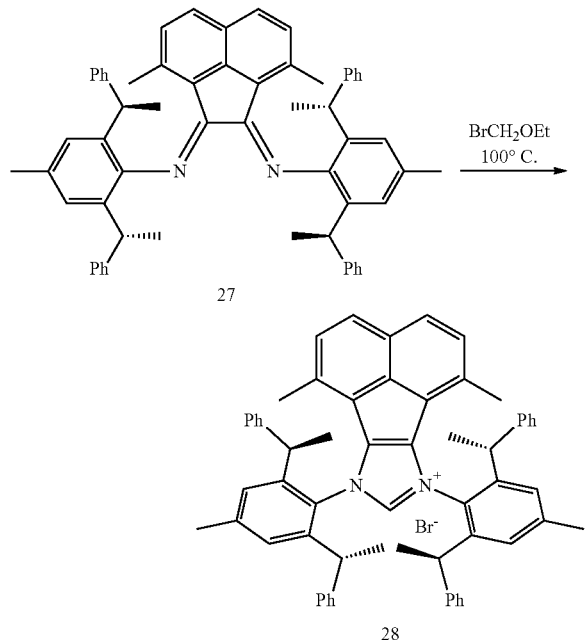

Compound 27 (64.4 mg, 0.08 mmol) and bromomethyl ether (151 mg, 1.6 mmol) were added to a nitrogen-flushed thick-walled reaction vessel. The vessel was sealed and the reaction mixture was stirred at 100° C. for 24 h. The reaction mixture was cooled to ambient temperature and the resulting solid was filtered off to afford the title compound 28 as a solid (42 mg, Yield=65%). $^1$H NMR (400 MHz, dmso) δ 10.09 (s, 1H), 7.94 (d, J=7.7 Hz, 1H), 7.87 (t, J=7.3 Hz, 1H), 7.55 (t, J=8.2 Hz, 2H), 7.43-7.35 (m, 3H), 7.33-7.25 (m, 1H), 7.17 (d, 0.1=7.5 Hz, 2H), 6.17 (d, 0.1=16.0 Hz, 1H), 5.87 (d, 0.1=16.6 Hz, 1H), 4.82 (d, 0.1=7.0 Hz, 1H), 4.01 (d, J=6.9 Hz, 1H), 2.29 (s, 3H), 1.77 (d, J=7.0 Hz, 3H), 1.69 (d, J=7.1 Hz, 3H), 1.21 (s, 4H).

Example 7

Synthesis of the 1,3-bis(3,4,5-trimethyl-2,6-bis((R)-1-phenylethyl)phenyl)-4,5-dihydro-1H-imidazol-3-ium chloride (compound 34)

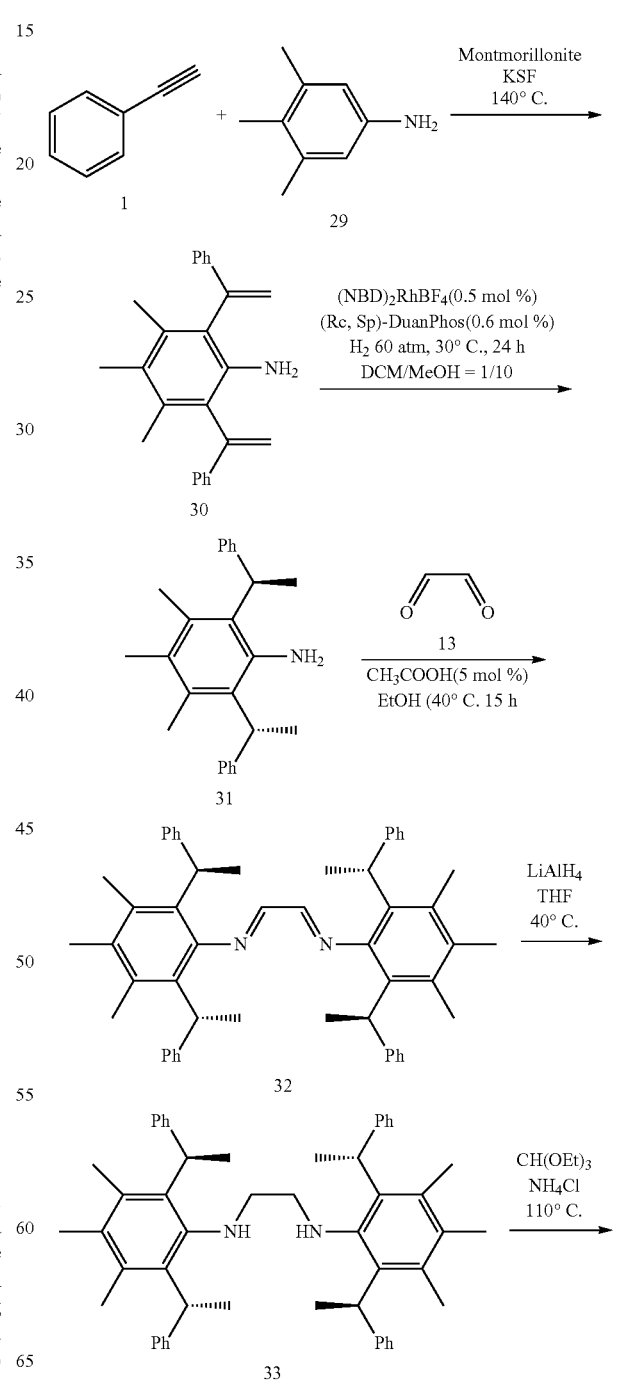

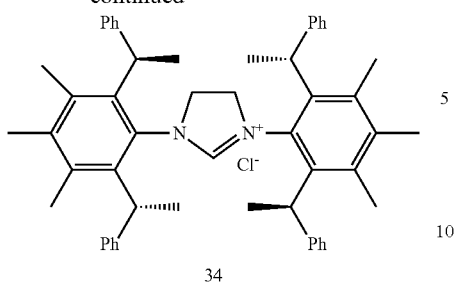

34

Synthesis of the 3, 4, 5-trimethyl-2, 6-bis(1-phenylvinyl) aniline (intermediate 30)

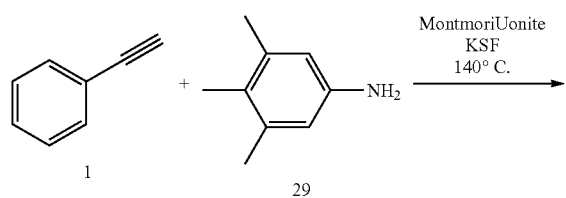

A 250 mL flask equipped with a stir bar was charged with 3, 4, 5-trimethylaniline (10.715 g, 100 mmol), KSF montmorillonite (10 g), and phenylacetylene (20.4 g, 200 mmol). The heterogeneous slurry was refluxed with vigorous stirring at 140° C. for 8 h. The reaction vessel was allowed to cool to room temperature before dilution with ethyl acetate and filtration. The solvent was removed under reduced pressure, and the residue was purified by adding petroleum ether to give intermediate 30 (10 g, Yield=30.6%).

Synthesis of the 3, 4, 5-trimethyl-2, 6-bis ((R)-1-phenylethyl) aniline (intermediate 31)

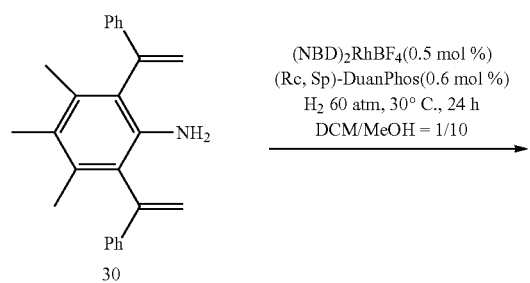

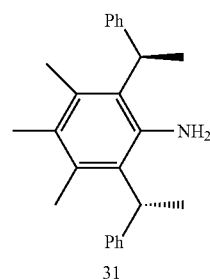

31

In a 100 mL microwave tube, (NBD)$_2$RhBF$_4$ (0.5 mol %) and (Rc,Sp)-DuanPhos (0.6 mol %) were dissolved in 10 mL DCM under a nitrogen atmosphere and stirred for 15 min. A solution of intermediate 30 (7 g, 22.51 mmol) in a minimal amount of MeOH was added. The microwave tube was transferred into the autoclave and the reactor was purged three times with H$_2$. The reactor was pressurized to 60 bar H$_2$ and the mixture was stirred at ambient temperature for 24 h. The reaction mixture was suction filtered, washed with methanol, and the solid was recrystallized from methanol to afford the desired chiral white intermediate 31 (4.7 g, Yield=68%).

Synthesis of the (1E,2E)-N$^1$,N$^2$-bis(3,4,5-trimethyl-2,6-bis((R)-1-phenylethyl)phenyl)ethane-1,2-diimine (intermediate 32)

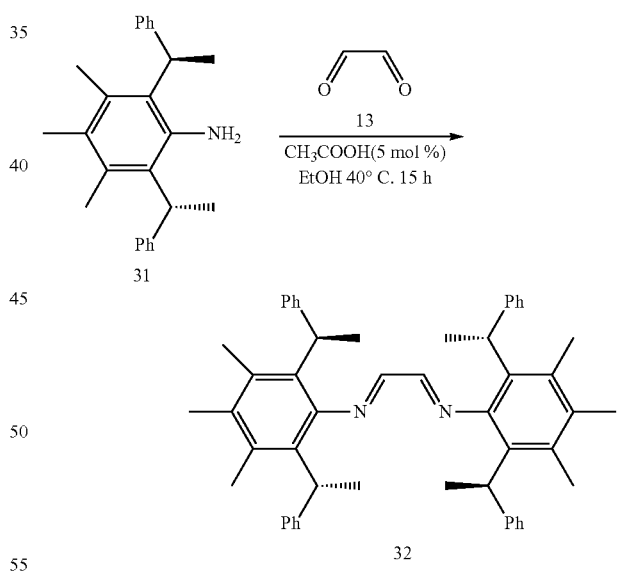

A 100 mL flask equipped with a stir bar was charged with intermediate 31 (3.15 g, 9.52 mmol) and 50 mL EtOH and was heated under reflux for 1 h. Drops of acetic acid (5 mol %) was then added and reflux was continued. A 40% solution of glyoxal (691 mg, 4.76 mmol) in water was added with the aid of a dropping funnel over a period of 30 min, and the resulting mixture was heated at 40° C. for further 15 h and then cooled to room temperature. The crude product was filtered, washed with EtOH and dried in vacuo to afford the intermediate 32 as a yellow solid (2.1 g, Yield=81%).

Synthesis of the N¹, N²-bis (3, 4, 5-trimethyl-2, 6-bis ((R)-1-phenylethyl) phenyl) ethane-1, 2-diamine (intermediate 33)

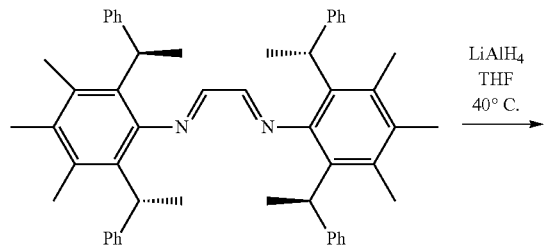

A 100 mL flask equipped with a stir bar was charged with intermediate 32 (3.4 g, 4.38 mmol), LiAlH₄ (499 mg, 13.14 mmol), and 30 mL THF under a nitrogen atmosphere. The mixture was stirred at 40° C. for 12 h. Saturated KOH solution was added, and the mixture was extracted with ethyl acetate three times, combined organic layer and dried over Na₂SO₄. The crude product obtained after filtration and concentration in vacuo was purified by column chromatography to afford t intermediate 33 (2.1 g, Yield=81%).

Synthesis of the 1,3-bis(3,4,5-trimethyl-2,6-bis((R)-1-phenylethyl)phenyl)-4,5-dihydro-1H-imidazol-3-ium chloride (compound 34)

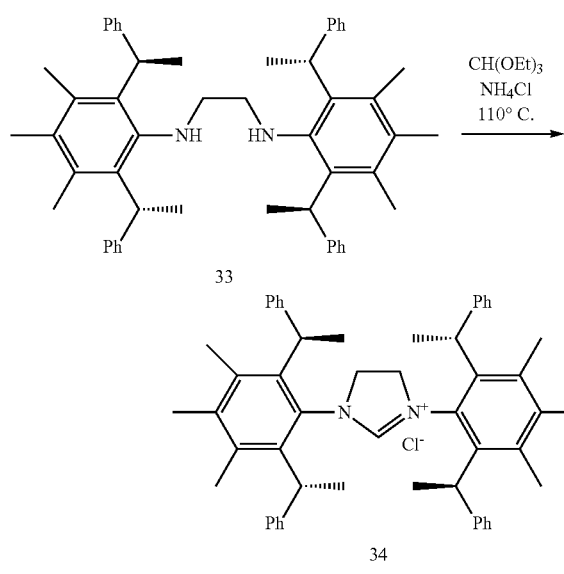

A 100 mL round-bottom flask equipped with a stir bar was charged with compound 33 (2.82 g, 4.29 mmol), NH₄Cl (344 mg, 6.4 mmol), and 20 mL HC (OEt)₃ under a nitrogen atmosphere. The mixture was stirred at 110° C. for 18 h and then cooled to room temperature. The crude product was filtered, washed with Et₂O and dried in vacuo to afford the saturated imidazolium salt as a white solid compound 34 (1.1 g, Yield=55%). ¹H NMR (400 MHz, CDCl₃) δ 10.32 (s, 1H), 7.38 (d, J=6.5 Hz, 3H), 7.23-7.13 (m, 4H), 6.97-6.88 (m, 3H), 4.42-4.31 (m, 1H), 4.26 (dd, J=12.9, 6.4 Hz, 1H), 3.68 (t, J=11.5 Hz, 1H), 3.03 (t, J=13.0 Hz, 1H), 2.34 (s, 3H), 2.21 (s, 3H), 2.14 (s, 3H), 1.73 (d, J=7.3 Hz, 3H), 1.44 (d, J=7.1 Hz, 3H).

Example 8

Synthesis of the 1,3-bis (4-methyl-2,6-bis ((R)-1-(m-tolyl) ethyl) phenyl)-4,5-dihydro-1H-imidazol-3-ium chloride

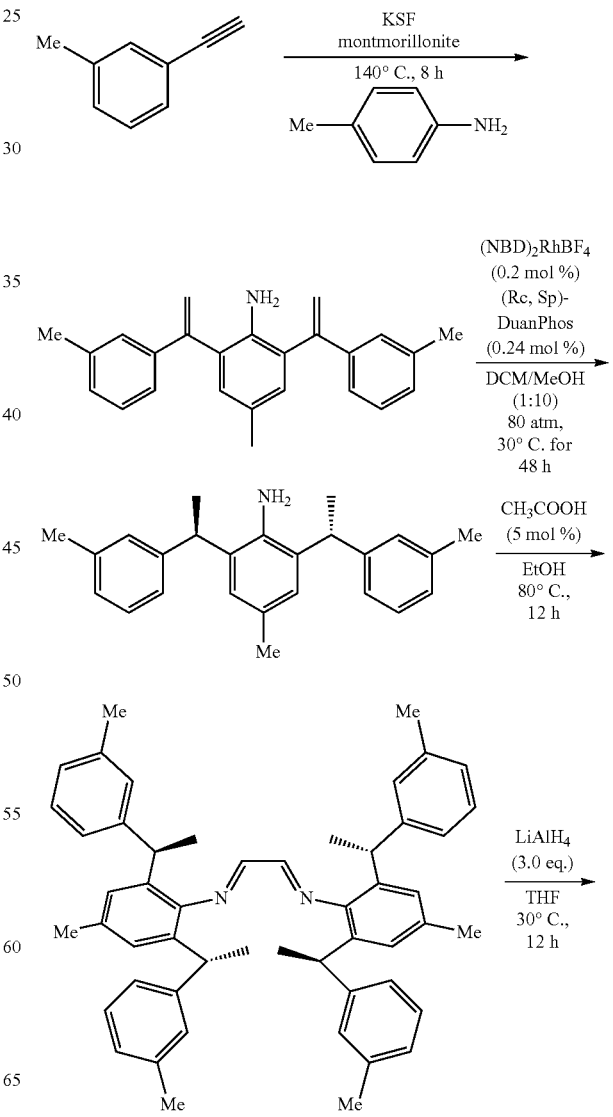

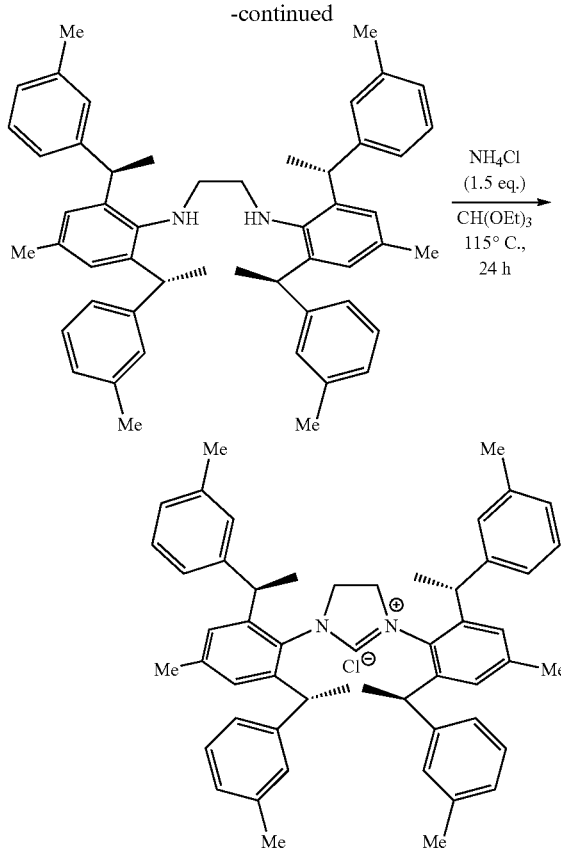

Synthesis of the 2, 6-bis (1-(3-methylphenyl) vinyl)-4-methylaniline

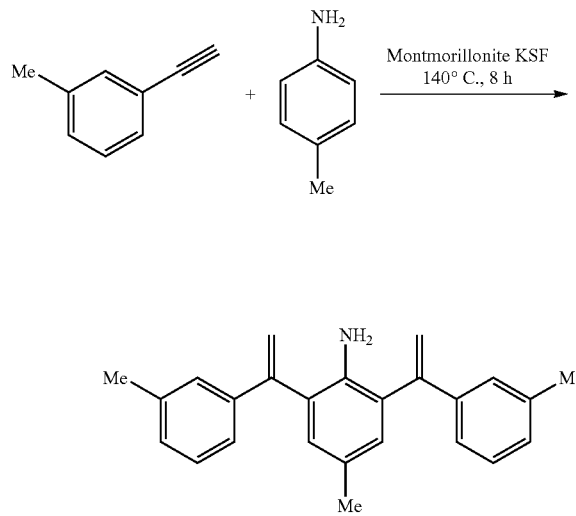

A 100 mL flask equipped with a stir bar was charged with p-methylaniline (4.3 g, 40 mmol, 1 eq.), KSF montmorillonite (4 g), and 3-methylphenylacetylene (11.4 mL, 88 mmol, 2.2 eq.). The heterogeneous slurry was refluxed with vigorous stirring at 140° C. for 8 h. The reaction vessel was allowed to cool to room temperature before dilution with ethyl acetate and filtration. The solvent was removed from the mother liquor under reduced pressure, and the residue was purified by column chromatography (0-2% EtOAc in hexanes) to provide the title compound as a pale yellow liquid (4.7 g, Yield=35%). $^1$H NMR (400 MHz, CDCl$_3$) δ: 7.24-7.16 (m, 6H), 7.16-7.05 (m, 2H), 6.99 (s, 2H), 5.79 (d, J=1.6 Hz, 2H), 5.38 (d, J=1.6 Hz, 2H), 3.39 (s, 2H), 2.37 (s, 6H), 2.35 (s, 3H).

Synthesis of the 2, 6-bis ((R)-1-(3-methylphenyl) ethyl)-4-methylaniline

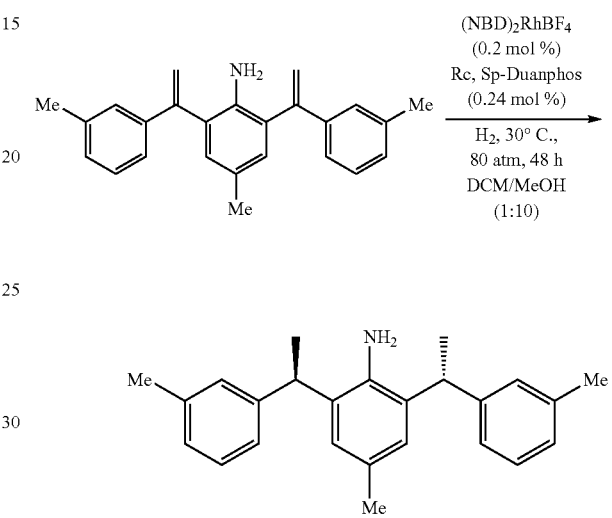

In a 100 mL microwave tube, (NBD)$_2$RhBF$_4$ (0.2 mol %) and (Rc,Sp)-DuanPhos (0.24 mol %) were dissolved in 3 mL DCM under a nitrogen atmosphere and stirred for 15 min. A solution of 2, 6-bis (1-(3-methylphenyl) vinyl)-4-methylaniline (1.6 g, 4.7 mmol, 1.0 equiv) in a minimal amount of 30 mL MeOH was added. The microwave tube was transferred into the autoclave and the reactor was purged three times with H$_2$. The reactor was pressurized to 60 bar H$_2$ and the mixture was stirred at ambient temperature for 48 h. The reaction mixture was suction filtered, washed with methanol, and the solid was purified by column chromatography (0-2% EtOAc in hexanes) to provide the title compound as a white solid (1.5 g, Yield=93%). $^1$H NMR (400 MHz, CDCl$_3$) δ: 7.19-7.13 (m, 2H), 7.10 (s, 2H), 7.03-6.95 (m, 6H), 3.98 (q, J=7.1 Hz, 2H), 3.28 (s, 2H), 2.42 (s, 3H), 2.31 (s, 6H), 1.61 (d, J=7.2 Hz, 6H).

Synthesis of the (1E, 2E)-N$^1$, N$^2$-bis (4-methyl-2, 6-bis ((R)-1-(m-tolyl) ethyl) phenyl) ethane-1, 2-diimine

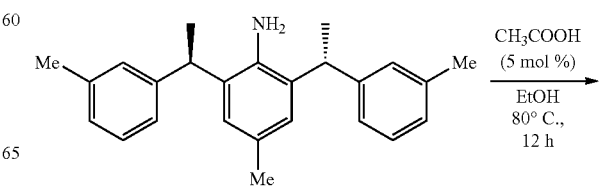

-continued

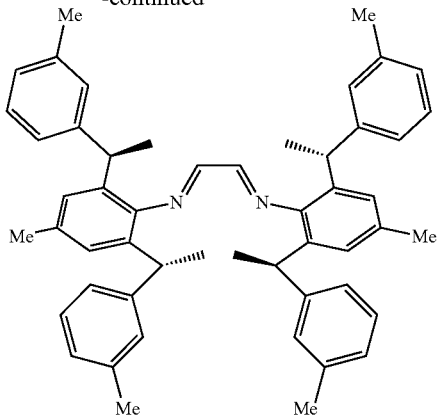

A 50 mL flask equipped with a stir bar was charged with 2, 6-bis ((R)-1-(3-methylphenyl) ethyl)-4-methylaniline (687 mg, 2 mmol, 1 eq.) and 10 mL EtOH and was heated under reflux for 1 h. Drops of acetic acid (5 mol %) was then added and reflux was continued. A 40% solution of glyoxal (691 mg, 4.76 mmol) in water was added with the aid of a dropping funnel over a period of 30 min, and the resulting mixture was heated under reflux for further 12 h and then cooled to room temperature. The concentrated crude product was used for the next step without further purification.

Synthesis of the $N^1$, $N^2$-bis (4-methyl-2, 6-bis ((R)-1-(m-tolyl) ethyl) phenyl) ethane-1, 2-diamine

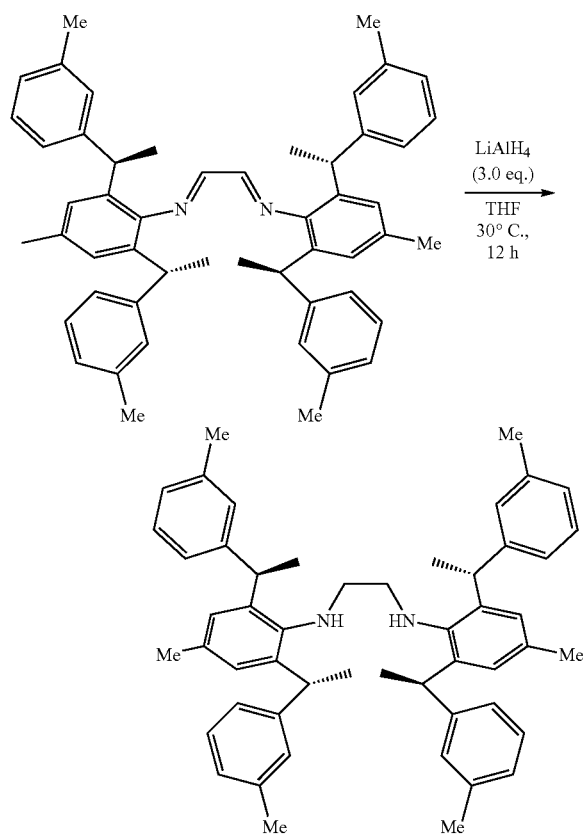

A 100 mL flask equipped with a stir bar was charged with (1E, 2E)-$N^1$, $N^2$-bis (4-methyl-2, 6-bis ((R)-1-(m-tolyl) ethyl)phenyl) ethane-1, 2-diimine and 20 mL THF. The mixture was cooled to 0° C. before LiAlH$_4$ (3.0 eq) was added under a nitrogen atmosphere. The mixture was stirred at 40° C. for 12 h. Saturated KOH solution was added, and the mixture was extracted with ethyl acetate, combined organic layer and dried over Na$_2$SO$_4$. The crude product obtained after filtration and concentration in vacuo was purified by column chromatography to afford the title compound (570 mg, two-step total Yield=80%). $^1$H NMR (400 MHz, CDCl$_3$) δ: 7.05 (t, J=7.5 Hz, 4H), 6.96 (d, J=1.9 Hz, 4H), 6.93 (d, J=6.2 Hz, 12H), 4.37 (q, J=7.1 Hz, 4H), 2.87-2.73 (m, 2H), 2.61-2.49 (m, 2H), 2.28 (s, 6H), 2.23 (s, 12H), 1.54 (d, J=7.2 Hz, 12H).

Synthesis of the 1, 3-bis (4-methyl-2, 6-bis ((R)-1-(m-tolyl) ethyl) phenyl)-4, 5-dihydro-1H-imidazol-3-ium chloride

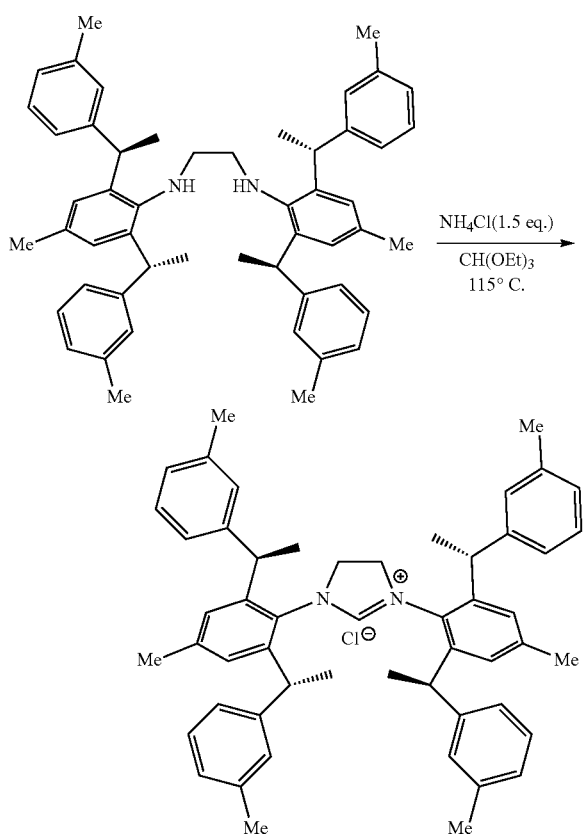

A 50 mL flask equipped with a stir bar was charged with $N^1$, $N^2$-bis (4-methyl-2, 6-bis ((R)-1-(m-tolyl) ethyl) phenyl) ethane-1, 2-diamine (630 mg, 0.88 mmol), NH$_4$C$_1$ (70.9 mg, 1.33 mmol, 1.5 eq.) and 10 mL HC (OEt)$_3$ under a nitrogen atmosphere. The mixture was stirred at 115° C. for 15 h and then cooled to room temperature. The crude product was was purified by column chromatography to afford the title saturated imidazolium salt as a white solid (415 mg, Yield=62%). $^1$H NMR (400 MHz, CDCl$_3$) δ: 10.40 (s, 1H), 7.25 (d, J=7.5 Hz, 2H), 7.18 (d, J=14.9 Hz, 6H), 7.08 (t, J=7.5 Hz, 2H), 7.02 (d, J=7.3 Hz, 2H), 6.95 (d, J=5.9 Hz, 4H), 6.74-6.62 (m, 4H), 4.29 (q, J=6.7 Hz, 2H), 4.13 (q, J=6.5 Hz, 2H), 3.78-3.62 (m, 2H), 3.19-3.01 (m, 2H), 2.35 (s, 12H), 2.23 (s, 6H), 1.73 (d, J=7.1 Hz, 6H), 1.42 (d, J=7.0 Hz, 6H). $R_1$, $R_4$, Ar and $X^-$ are the same as before.

Example 9
Synthesis of the 1,3-bis(2,6-bis((R)-1-(3,5-dimethylpheny)ethyl)-4-methylphenyl)-4,5-dihydro-1H-imidazol-3-ium chloride
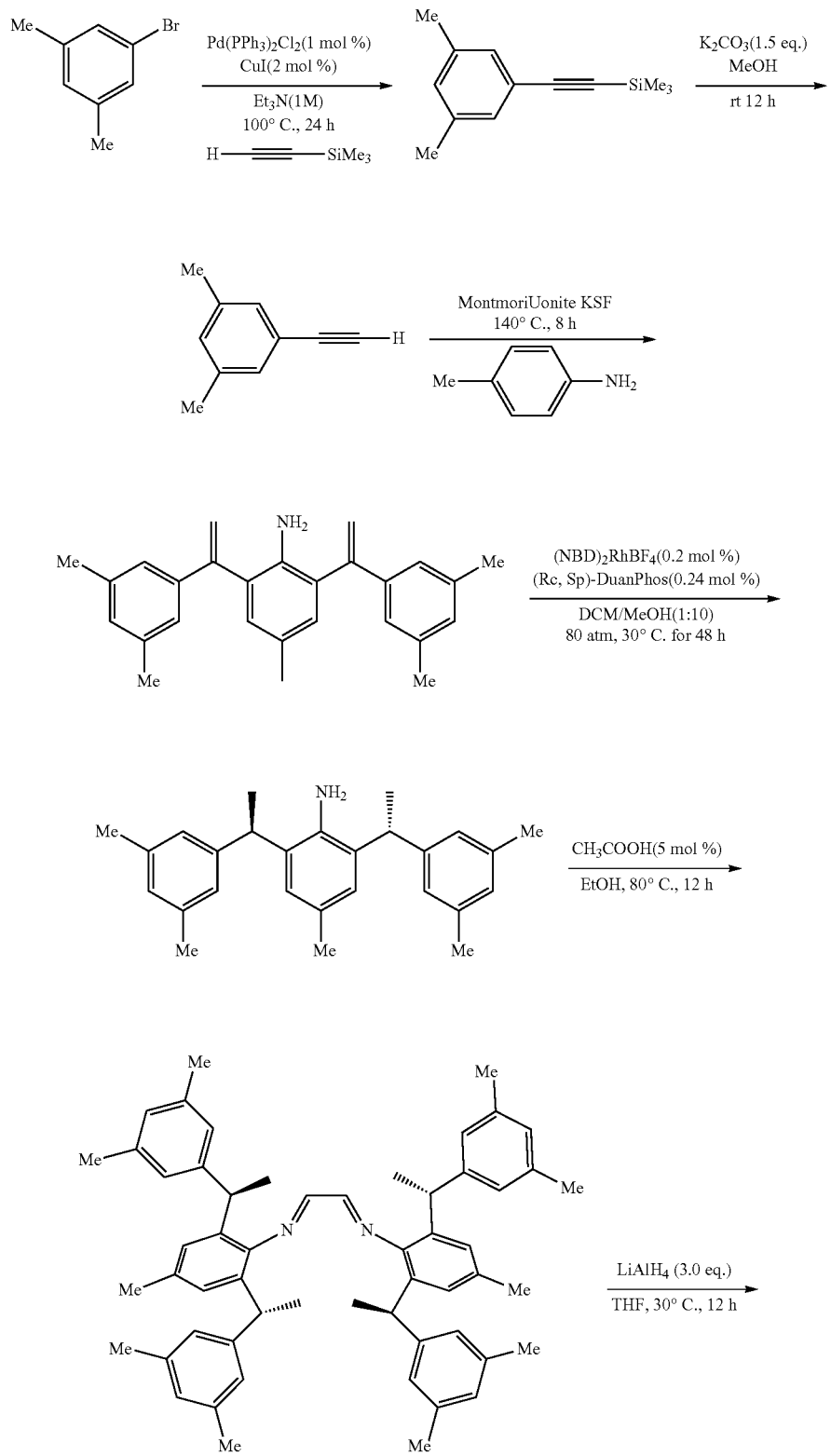

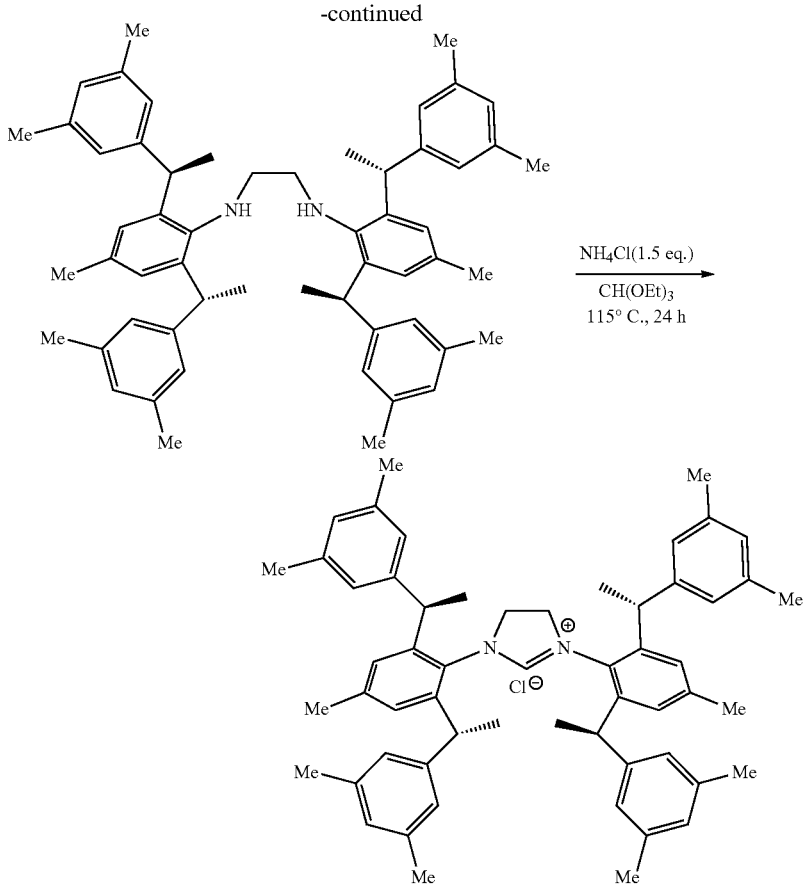

Synthesis of the ((3, 5-dimethylphenyl) ethynyl) trimethylsilane

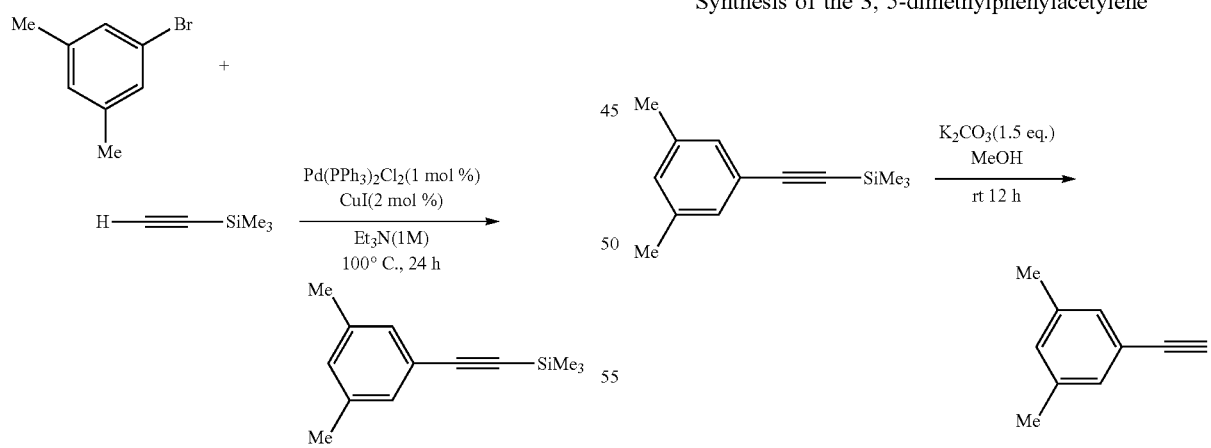

A 300 mL flask equipped with a stir bar was charged with 3, 5-dimethylbromobenzene (11.5 g, 1200 mmol), trimethylethynyl silicon (11.5 mL, 120 mmol), cuprous iodide (762 mg, 4 mmol %), bis (triphenylphosphine) palladium (II) chloride (2.344 g, 2 mmol %), and 150 mL Et$_3$N. The mixture was stirred at 100° C. for 24 h and then cooled to room temperature. The crude product was purified by column chromatography (0-2% EtOAc in hexanes) to provide the title compound as a pale yellow liquid (19.9 g, Yield=98.5%). $^1$H NMR (400 MHz, CDCl$_3$) δ: 7.11 (s, 2H), 6.95 (s, 1H), 2.28 (s, 6H), 0.25 (s, 9H).

Synthesis of the 3, 5-dimethylphenylacetylene

A 1 L flask equipped with a stir bar was charged with ((3, 5-dimethylphenyl) ethynyl) trimethylsilane (19 g, 82.6 mmol, 1.0 equiv), 250 mL MeOH, K$_2$CO$_3$ (17.1 g, 300 mmol). The mixture was stirred at room temperature for 12 h. The MeOH solution was removed by concentrated, diluted with ether and the mixture was washed with saturated NaCl solution, combined organic layer and dried over Na$_2$SO$_4$. The crude product was purified by column chromatography (0-2% EtOAc in hexanes) to provide the title compound as a slightly yellow liquid (12.7 g, Yield=96.9%). $^1$H NMR (400 MHz, CDCl$_3$) δ: 7.14 (s, 2H), 6.99 (s, 1H), 3.02 (s, 1H), 2.30 (s, 6H). $^{13}$C NMR (101 MHz, CDCl$_3$) δ: 138.0, 130.8, 129.9, 121.8, 84.1, 76.5, 21.2.

Synthesis of the 2, 6-bis (1-(3, 5-dimethylphenyl)vinyl)-4-methylaniline

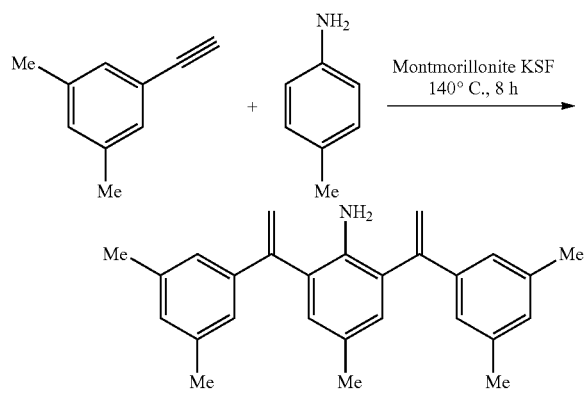

A 100 mL flask equipped with a stir bar was charged with p-methylaniline (10.7 g, 100 mmol, 1 eq.), KSF montmorillonite (10 g), and 3, 5-dimethylphenylacetylene (28.6 g, 220 mmol, 2.2 eq.). The heterogeneous slurry was refluxed with vigorous stirring at 140° C. for 8 h. The reaction vessel was allowed to cool to room temperature before dilution with ethyl acetate and filtration. The solvent was removed from the mother liquor under reduced pressure, and the resultant was purified by column chromatography (0-2% EtOAc in hexanes) to provide the title compound as a white solid (12.51 g, Yield=34%). $^1$H NMR (400 MHz, CDCl$_3$) δ: 6.98 (s, 4H), 6.95 (s, 2H), 6.91 (s, 2H), 5.72 (d, J=1.6 Hz, 2H), 5.31 (d, J=1.6 Hz, 2H), 2.30 (s, 3H), 2.27 (s, 12H).

Synthesis of the 2, 6-bis ((R)-1-(3, 5-dimethylphenyl) ethyl)-4-methylaniline

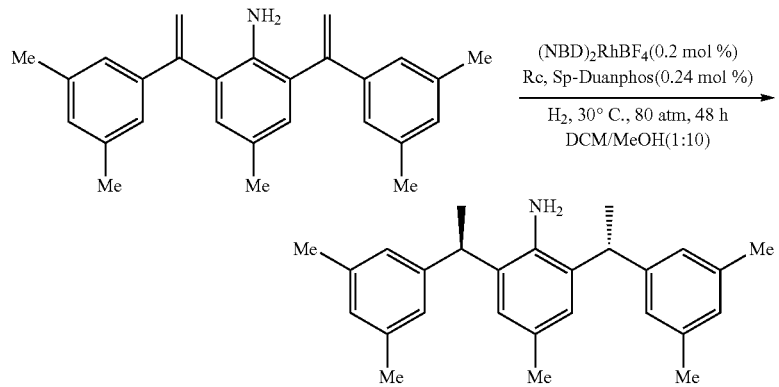

In a 100 mL microwave tube, (NBD)$_2$RhBF$_4$ (0.2 mol %) and (Rc,Sp)-DuanPhos (0.24 mol %) were dissolved in 6 mL DCM under a nitrogen atmosphere and stirred for 15 min. A solution of 2, 6-bis (1-(3, 5-dimethylphenyl) vinyl)-4-methylaniline (7.43 g, 20 mmol, 1.0 equiv) in a minimal amount of MeOH was added. The microwave tube was transferred into the autoclave and the reactor was purged three times with H$_2$. The reactor was pressurized to 80 bar H$_2$ and the mixture was stirred at ambient temperature for 48 h. The reaction mixture was suction filtered, washed with methanol, and the solid was purified by column chromatography (0-2% EtOAc in hexanes) to provide the title compound as a white solid (7.31 g, Yield=98.3%). $^1$H NMR (600 MHz, CDCl$_3$) δ: 7.06 (s, 2H), 6.80 (s, 2H), 6.76 (s, 4H), 3.95 (q, J=7.1 Hz, 2H), 2.39 (s, 3H), 2.23 (s, 12H), 1.57 (d, J=7.1 Hz, 6H). $^{13}$C NMR (151 MHz, CDCl$_3$) δ: 145.3, 138.3, 128.4, 126.7, 125.4, 40.4, 22.5, 21.5, 21.4.

Synthesis of the (1E,2E)-N$^1$,N$^2$-bis(2,6-bis((R)-1-(3, 5-dimethylphenyl)ethyl)-4-methylphenyl)ethane-1,2-diimine

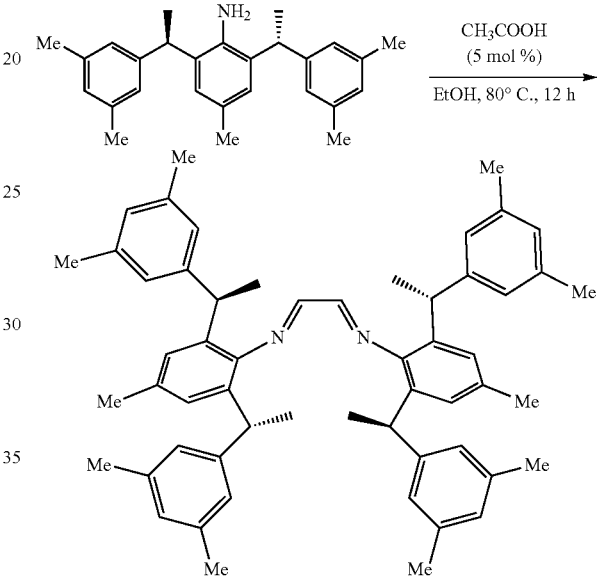

A 50 mL flask equipped with a stir bar was charged with 2, 6-bis ((R)-1-(3, 5-dimethylphenyl) ethyl)-4-methylaniline (7.0 g, 18.84 mmol) and 40 mL EtOH and heated under reflux for 1 h. Drops of acetic acid (5 mol %) was then added and reflux was continued. A 40% solution of glyoxal (0.5 eq) in water was added with the aid of a dropping funnel over a period of 30 min, and the resulting mixture was heated at 80° C. for further 12 h and then cooled to room temperature.

The mixture was purified by column chromatography to provide the title compound as a yellow solid (6.2 g, Yield=86%). $^1$H NMR (400 MHz, CDCl$_3$) δ: 7.81 (s, 2H), 6.96 (s, 4H), 6.82 (d, J=7.4 Hz, 12H), 4.03 (q, J=7.1 Hz, 4H), 2.32 (s, 6H), 2.26 (s, 24H), 1.51 (d, J=7.2 Hz, 12H). $^{13}$C NMR (101 MHz, CDCl$_3$) δ: 164.1, 146.3, 137.8, 134.4, 129.1, 121.8, 39.0, 22.0.

Synthesis of the N$^1$,N$^2$-bis(2,6-bis((R)-1-(3,5-dimethylphenyl)ethyl)-4-methylphenyl)ethane-1,2-diamine

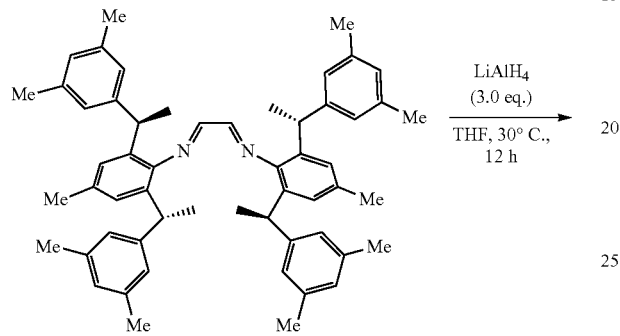

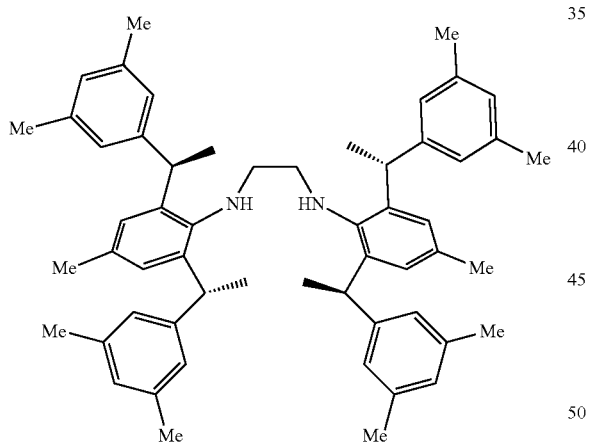

A 100 mL flask equipped with a stir bar was charged with (1E,2E)-N$^1$,N$^2$-bis(2,6-bis((R)$_1$-(3,5-dimethylphenyl) ethyl)-4-methylphenyl)ethane-1,2-diimine (6.0 g, 7.83 mmol), 40 mL THF, and LiAlH$_4$ (3.0 eq) under a nitrogen atmosphere. The mixture was stirred at room temperature for 12 h. Saturated KOH solution was added, and the mixture was extracted with EtOAc, combined organic layer and dried over Na$_2$SO$_4$. The crude product obtained after filtration and concentration in vacuo was purified by column chromatography to afford the title compound (5.88 g, Yield=97.5%). $^1$H NMR (400 MHz, CDCl$_3$) δ: 7.01 (s, 4H), 6.81 (s, 12H), 4.35 (q, J=7.2 Hz, 4H), 2.95-2.74 (m, 2H), 2.58-2.48 (m, 2H), 2.34 (s, 6H), 2.25 (s, 24H), 1.54 (d, J=7.1 Hz, 12H).

Synthesis of the 1,3-bis(2,6-bis((R)-1-(3,5-dimethylphenyl)ethyl)-4-methylphenyl)-4,5-dihydro-1H-imidazol-3-ium chloride

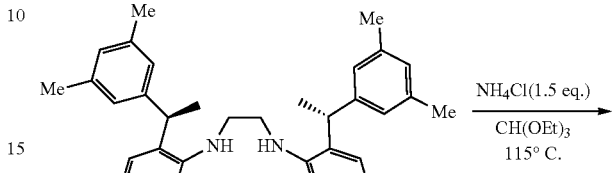

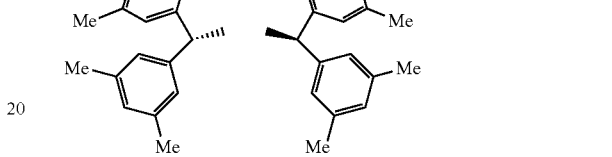

A 50 mL flask equipped with a stir bar was charged with N$^1$,N$^2$-bis(2,6-bis((R)-1-(3,5-dimethylphenyl)ethyl)-4-methylphenyl)ethane-1,2-diamine (1.0 g, 770 mmol), NH$_4$Cl (104 mg, 1.95 mmol, 1.5 eq.), and 10 mL HC(OEt)$_3$ under a nitrogen atmosphere. The mixture was stirred at 115° C. for 15 h and then cooled to room temperature. The crude product was was purified by column chromatography to afford the title saturated imidazolium salt as a white solid (693 mg, Yield=65.3%). $^1$H NMR (400 MHz, CDCl$_3$) δ: 10.81 (s, 1H), 7.26 (s, 2H), 7.14 (s, 4H), 7.01 (s, 2H), 6.93 (s, 2H), 6.86 (s, 2H), 6.77 (s, 4H), 6.47 (s, 2H), 4.26 (q, J=7.1 Hz, 2H), 4.06 (q, J=6.9 Hz, 2H), 3.75-3.63 (m, 2H), 3.31-3.12 (m, 6H), 2.33 (d, J=9.7 Hz, 12H), 2.18 (s, 12H), 1.72 (d, J=7.1 Hz, 6H), 1.40 (d, J=6.9 Hz, 6H). $^{13}$C NMR (101 MHz, CDCl$_3$) δ: 161.6, 146.0, 144.2, 143.4, 142.1, 141.2, 138.6, 138.4, 128.8, 128.6, 128.5, 128.4, 127.9, 125.2, 124.8, 52.8, 40.2, 38.2, 23.2, 22.1, 21.8, 21.5, 21.4.

Example 10
Synthesis of the 1,3-bis(2,6-bis((R)-1-(3,5-di-tert-butylphenyl)ethyl)-4-methylphenyl)-4,5-dihydro-1H-imidazol-3-ium chloride
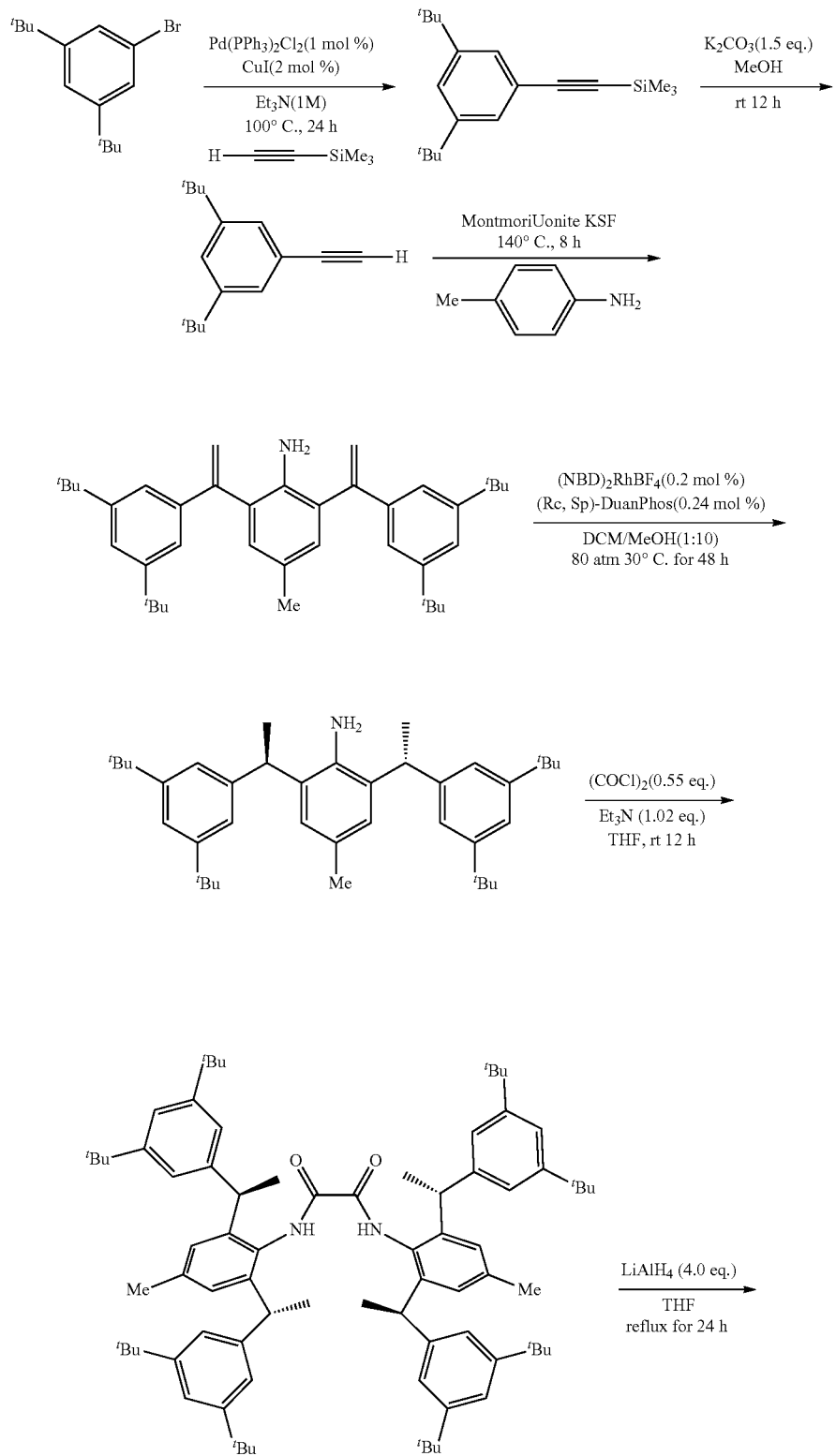

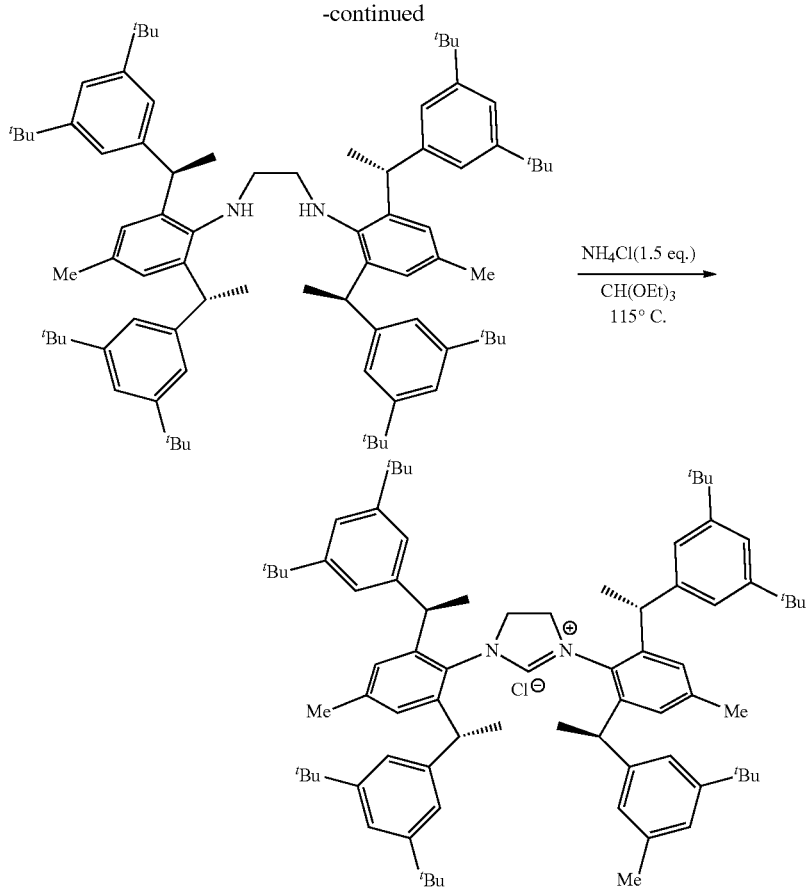

Synthesis of the ((3, 5-di-tert-butylphenyl) ethynyl) trimethylsilane

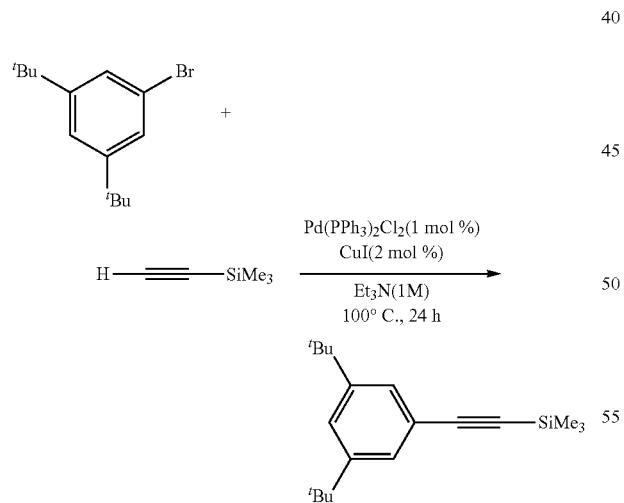

A 300 mL flask equipped with a stir bar was charged with 3, 5-di-tert-butyl bromobenzene (53.8 g, 200 mmol), trimethylethynyl silicon (34 mL, 240 mmol), cuprous iodide (762 mg, 4 mmol %), bis (triphenylphosphine) palladium (II) chloride (1.4 g, 2 mmol) and 150 mL Et$_3$N. The mixture was stirred at 100° C. for 24 h. The crude product was filtration, concentrated and used directly in the next step.

Synthesis of the 1, 3-di-tert-butyl-5-ethynylbenzene

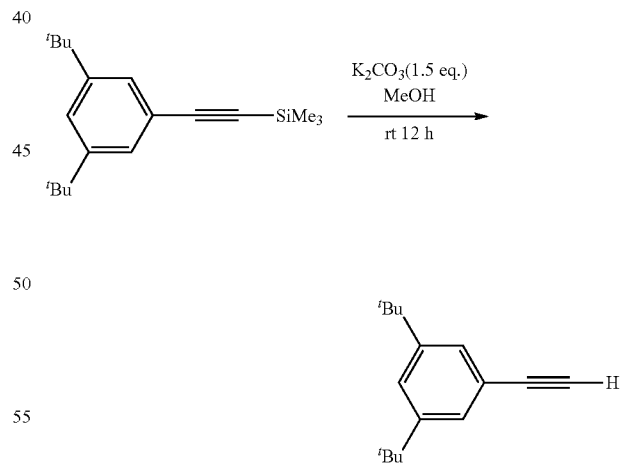

A 1 L flask equipped with a stir bar was charged with ((3, 5-di-tert-butylphenyl) ethynyl) trimethylsilane, 350 mL MeOH, K$_2$CO$_3$ (41.5 g, 300 mmol). The mixture was stirred at room temperature for 12 h. The MeOH solution was removed by concentrated, diluted with ether and washed with saturated NaCl solution, combined organic layer, and dried over Na$_2$SO$_4$. The crude product was purified by column chromatography to provide the title compound as a pale yellow liquid (38.6 g, Yield=90%).

Synthesis of the 2, 6-bis (1-(3, 5-di-tert-butylphenyl) vinyl)-4-methylaniline

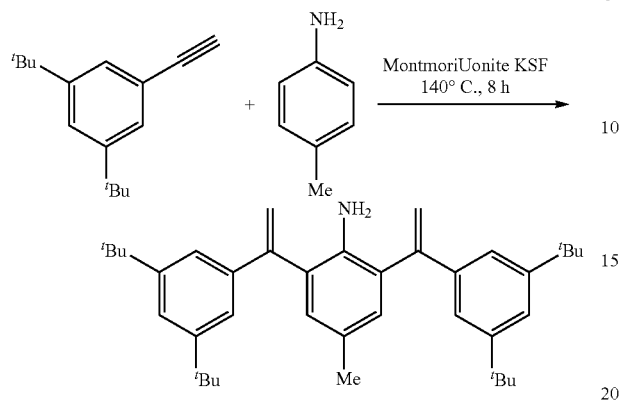

A 100 mL flask equipped with a stir bar was charged with p-methylaniline (10.7 g, 100 mmol, 1 eq.), KSF montmorillonite (10 g), and 1, 3-di-tert-butyl-5-ethynylbenzene (47.08 g, 220 mmol, 2.2 eq.). The heterogeneous slurry was refluxed with vigorous stirring at 140° C. for 8 h. The reaction vessel was allowed to cool to room temperature before dilution with ethyl acetate and filtration. The solvent was removed from the mother liquor under reduced pressure, and the residue was purified by column chromatography (0-2% EtOAc in hexanes) to provide the title compound as a yellow solid (19.9 g, Yield=37.2%).

Synthesis of the 2, 6-bis ((R)-1-(3, 5-di-tert-butylphenyl) ethyl)-4-methylaniline

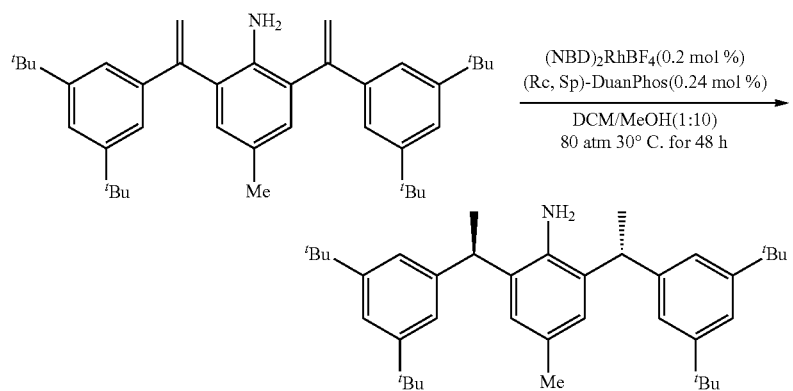

In a 100 mL microwave tube, $(NBD)_2RhBF_4$ (0.3 mol %) and (Rc,Sp)-DuanPhos (0.36 mol %) were dissolved in 12 mL DCM under a nitrogen atmosphere and stirred for 15 min. A solution of 2, 6-bis (1-(3, 5-di-tert-butylphenyl) vinyl)-4-methylaniline (18.5 g, 34.5 mmol) in 120 mL MeOH was added. The microwave tube was transferred into the autoclave and the reactor was purged three times with $H_2$. The reactor was pressurized to 80 bar $H_2$ and the mixture was stirred at ambient temperature for 48 h. The solvent was removed under reduced pressure, and the residue was purified by column chromatography to provide the title compound as a liquid (13.0 g, Yield=70%). $^1$H NMR (400 MHz, $CDCl_3$) δ: 7.22 (t, J=1.8 Hz, 2H), 7.02 (d, J=1.9 Hz, 4H), 6.97 (s, 2H), 4.02 (q, J=7.1 Hz, 2H), 3.29 (s, 2H), 2.33 (s, 3H), 1.59 (d, J=7.2 Hz, 6H), 1.25 (s, 36H).

Synthesis of the $N^1$, $N^2$-bis (2, 6-bis ((R)-1-(3, 5-di-tert-butylphenyl) ethyl)-4-methylphenyl) oxamide

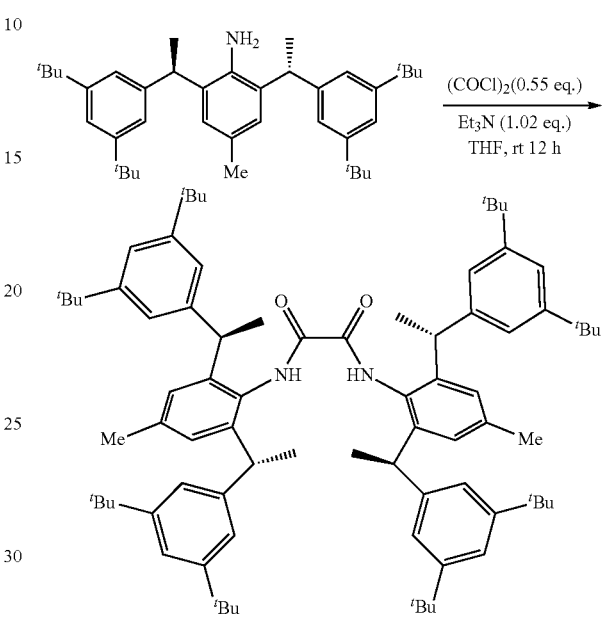

A 50 mL flask equipped with a stir bar was charged with 2, 6-bis ((R)-1-(3, 5-di-tert-butylphenyl) ethyl)-4-methylaniline (1.89 g, 3.5 mol), $Et_3N$ (535 μL, 3.9 mol), 15 mL THF and cooled to 0° C. Drops of oxalyl chloride (163 μL, 1.9 mol) was added. The reaction mixture was stirred overnight. Saturated $NaHCO_3$ solution was added, and the mixture was extracted with DCM, combined organic layer and dried over $Na_2SO_4$. The crude product obtained after filtration and concentration in vacuo was purified by column chromatography to afford the title product (1.68 g, Yield=85%). $^1$H NMR (400 MHz, $CDCl_3$) δ: 8.58 (s, 2H), 7.25-7.20 (m, 4H), 7.08 (d, J=1.8 Hz, 8H), 6.93 (s, 4H), 4.23 (q, J=7.0 Hz, 4H), 2.27 (s, 6H), 1.54 (d, J=7.1 Hz, 6H), 1.26 (s, 72H), 0.93 (d, J=6.6 Hz, 6H).

Synthesis of the N¹, N²-bis (2,6-bis ((R)-1-(3,5-di-tert-butylphenyl) ethyl)-4-methylphenyl) ethane-1,2-diamine

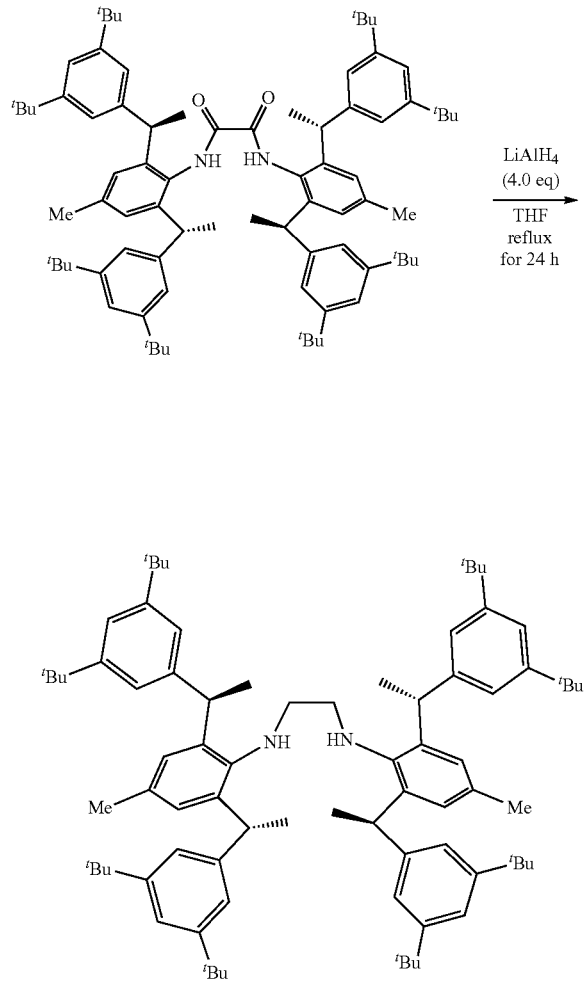

A 100 mL flask equipped with a stir bar was charged with N¹, N²-bis (2, 6-bis ((R)-1-(3, 5-di-tert-butylphenyl) ethyl)-4-methylphenyl) ethane-1, 2-diamine (3.0 g, 2.65 mmol), 30 mL THF, and LiAlH₄ (3.0 eq) under a nitrogen atmosphere. The mixture was stirred for 24 h. Saturated KOH solution was added, and the mixture was extracted with EtOAc, combined organic layer and dried over Na₂SO₄. The crude product obtained after filtration and concentration in vacuo was purified by column chromatography to afford the title compound (1.8 g, Yield=62%). ¹H NMR (400 MHz, CDCl₃) δ: 7.22 (t, J=1.8 Hz, 4H), 7.12 (d, J=1.9 Hz, 8H), 7.01 (s, 4H), 4.62 (q, J=7.1 Hz, 4H), 3.12 (d, 0.1=7.2 Hz, 2H), 2.60 (d, 0.1=7.5 Hz, 2H), 2.35 (s, 6H), 1.65 (d, J=7.1 Hz, 12H), 1.25 (s, 72H).

Synthesis of the 1,3-bis(2,6-bis((R)-1-(3,5-di-tert-butylphenyl)ethyl)-4-methylphenyl)-4,5-dihydro-1H-imidazol-3-ium chloride

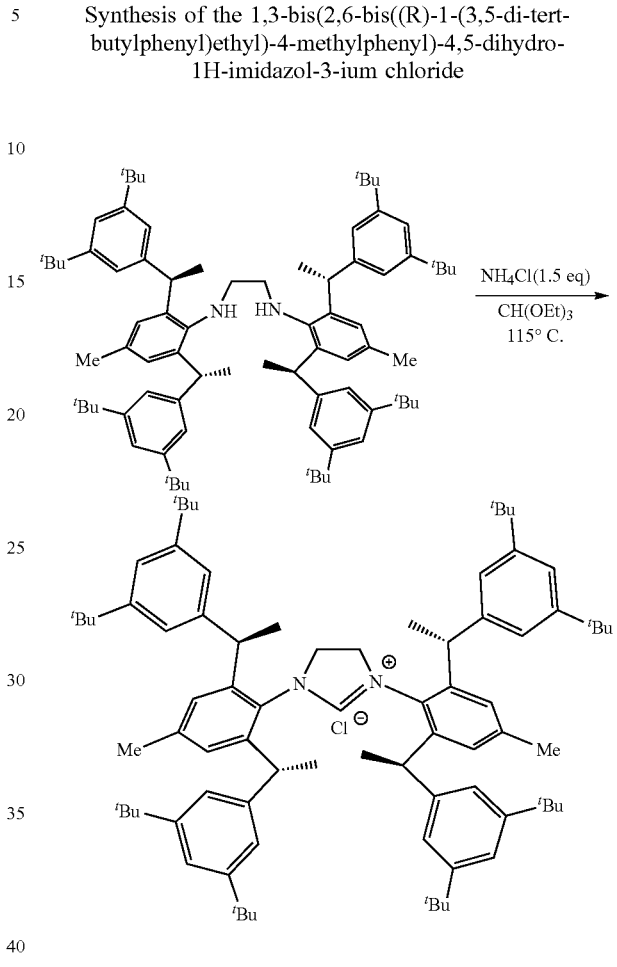

A 10 mL flask equipped with a stir bar was charged with N¹,N²-bis(2,6-bis((R)-1-(3,5-dimethylphenyl)ethyl)-4-methylphenyl)ethane-1,2-diamine (829 mg, 0.75 mmol), NRIC1 (48.1 mg, 0.9 mmo) and 4 mL HC(OEt)₃ under a nitrogen atmosphere. The mixture was stirred at 115° C. for 15 h and then cooled to room temperature. The crude product was was purified by column chromatography to afford the title saturated imidazolium salt (778 mg, Yield=90%). ¹H NMR (400 MHz, CDCl₃) δ: 8.24 (s, 1H), 7.29 (d, J=2.2 Hz, 4H), 7.04 (s, 4H), 6.92 (t, J=1.9 Hz, 8H), 4.49-4.32 (m, 4H), 4.20 (d, J=11.4 Hz, 2H), 3.89 (q, J=7.0 Hz, 2H), 2.31 (s, 6H), 1.84 (d, J=7.0 Hz, 6H), 1.30 (s, 36H), 1.19 (s, 36H), 1.06 (d, J=7.1 Hz, 6H).

Example 11

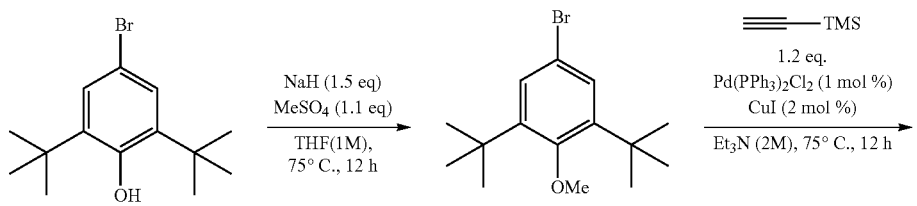

-continued
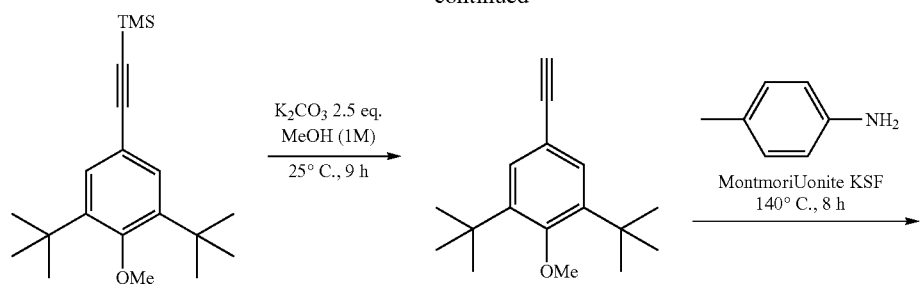
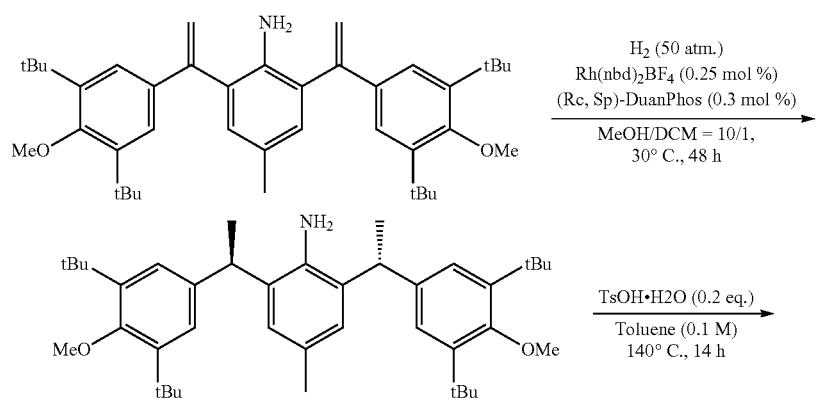
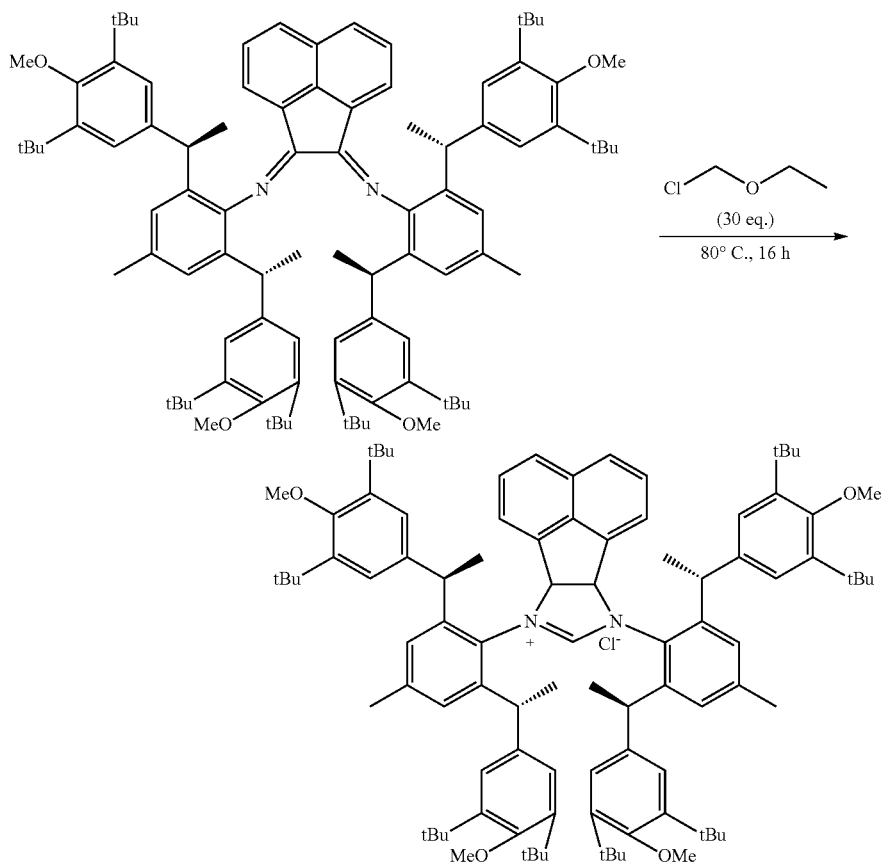

Synthesis of the 5-bromo-1, 3-di-tert-butyl-2-methoxybenzene

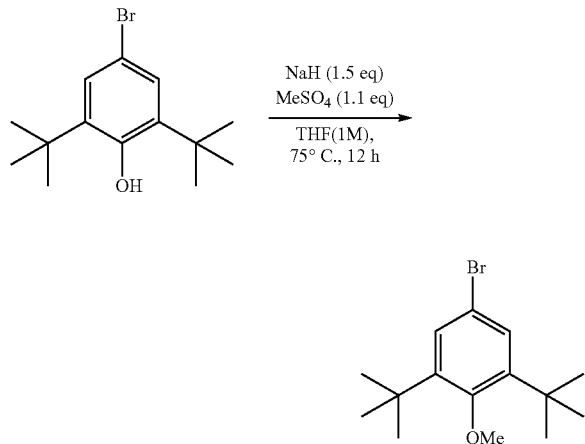

A 500 mL flask equipped with a stir bar was charged with 200 mL THF, NaH (3.2 g, 131.5 mmol), 4-bromo-2, 6-di-tert-butylphenol (25 g, 87.7 mmol) and THF. The mixture was stirred at room temperature for 1 h. After dimethyl sulfate (9.1 mL, 96.4 mmol) was added dropwise, the mixture was heated to 75° C. for 12 h and then cooled to room temperature. 100 mL H₂O was added, and the mixture was extracted with EtOAc, combined organic layer, and dried over Na₂SO₄. The crude product obtained after filtration and concentration in vacuo was purified by column chromatography to afford the title compound (23.4 g, Yield=89%). ¹H NMR (400 MHz, CDCl₃) δ 7.33 (s, 2H), 3.67 (s, 3H), 1.40 (s, 18H).

Synthesis of the ((3, 5-Di-tert-butyl-4-methoxyphenyl) ethynyl) trimethylsilane

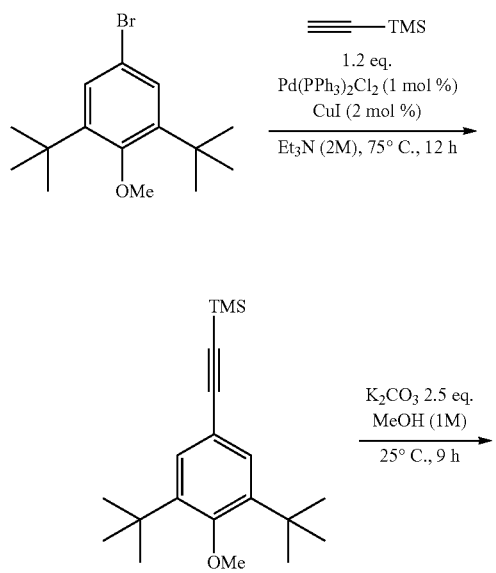

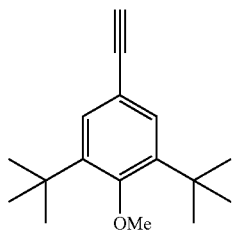

A 300 mL flask equipped with a stir bar was charged with 5-bromo-1,3-di-tert-butyl-2-methoxybenzene (26 g, 87 mmol), trimethylethynyl silicon (14.1 mL, 100 mmol), cuprous iodide (332 mg, 1.74 mmol), bis (triphenylphosphine) palladium (II) chloride (611 mg, 0.87 mmol) and 60 mL Et₃N. The mixture was stirred at 75° C. for 12 h. The crude product was filtration, concentrated and used directly in the next step.

A 1 L round-bottom flask equipped with a stir bar was charged with ((3, 5-Di-tert-butyl-4-methoxyphenyl) ethynyl) trimethylsilane, 120 mL MeOH, K₂CO₃ (30 g, 218 mol). The mixture was stirred at room temperature for 9 h. The MeOH solution was removed by concentrated, diluted with ether. The mixture was washed with water, combined organic layer and dried over Na₂SO₄. The crude product was purified by column chromatography to provide the title compound as a colorless liquid (19.1 g, Yield=90%). ¹H NMR (400 MHz, CDCl₃) δ 7.35 (s, 2H), 3.65 (s, 3H), 1.41 (s, 18H), 0.25 (s, 9H).

Synthesis of the 2, 6-bis (1-(3, 5-di-tert-butyl-4-methoxyphenyl) vinyl)-4-methylaniline

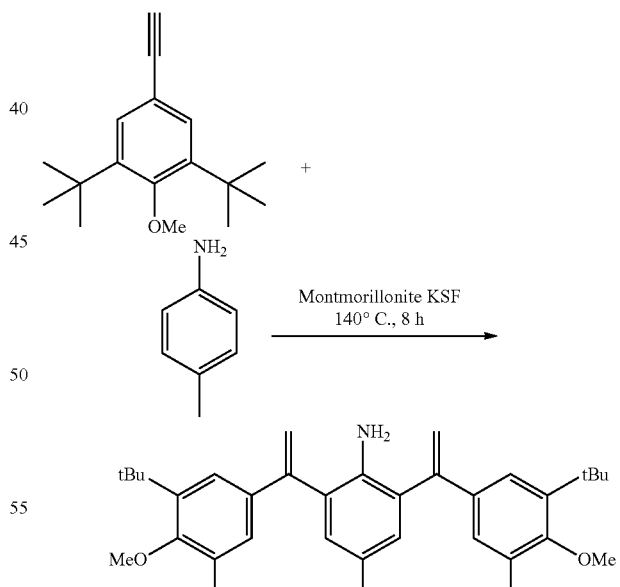

A 350 mL flask equipped with a stir bar was charged with p-methylaniline (7.3 g, 68 mmol, 1 eq.), KSF montmorillonite (5 g), and 1, 3-di-tert-butyl-5-ethynyl-2-methoxybenzene (36.6 g, 150 mmol, 2.2 eq.). The heterogeneous slurry was refluxed with vigorous stirring at 140° C. for 8 h. The reaction vessel was allowed to cool to room temperature before dilution with ethyl acetate and filtration. The solvent was removed from the mother liquor under reduced pressure, and the resultant was purified by column chromatography to provide the title compound as a yellow solid (13.4 g, Yield=33%). $^1$H NMR (400 MHz, CDCl$_3$) δ 7.28 (s, 4H), 6.88 (d, J=0.8 Hz, 2H), 5.71 (d, J=1.6 Hz, 2H), 5.27 (d, J=1.6 Hz, 2H), 3.65 (s, 6H), 2.25 (s, 3H), 1.37 (s, 26H).

Synthesis of the 2, 6-bis ((R)-1-(3, 5-di-tert-butylphenyl-4-methoxyphenyl) ethyl)-4-methylaniline

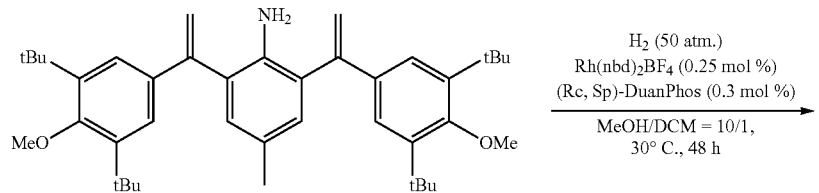

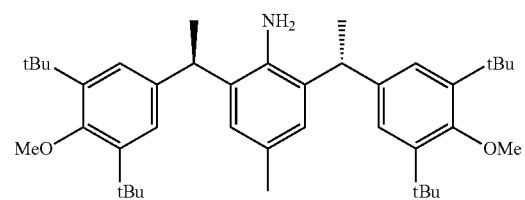

In a 300 mL microwave tube, (NBD)$_2$RhBF$_4$ (0.25 mol %) and (Rc,Sp)-DuanPhos (0.3 mol %) were dissolved in 12 mL DCM under a nitrogen atmosphere and stirred for 15 min. A solution of 2, 6-bis (1-(3, 5-di-tert-butyl-4-methoxyphenyl) vinyl)-4-methylaniline (13.4 g, 22.4 mmol) in 120 mL MeOH was added. The microwave tube was transferred into the autoclave and the reactor was purged three times with H$_2$. The reactor was pressurized to 50 bar H$_2$ and the mixture was stirred at ambient temperature for 48 h. The solvent was removed under reduced pressure, and the residue was purified by column chromatography to provide the title compound as a yellow solid (12.1 g, Yield=90%). $^1$H NMR (400 MHz, CDCl$_3$) δ 7.03 (s, 4H), 6.92 (s, 2H), 3.97 (q, J=7.1 Hz, 2H), 3.64 (s, 6H), 2.31 (s, 3H), 1.56 (d, J=7.1 Hz, 6H), 1.34 (s, 36H).

Synthesis of the (1E,2E)-N$^1$,N$^2$-bis(2,6-bis((R)-1-(3, 5-di-tert-butyl-4-methoxyphenyl)ethyl)-4-methylphenyl)acenaphthylene-1,2-diimine

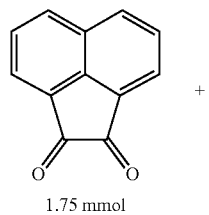

1.75 mmol

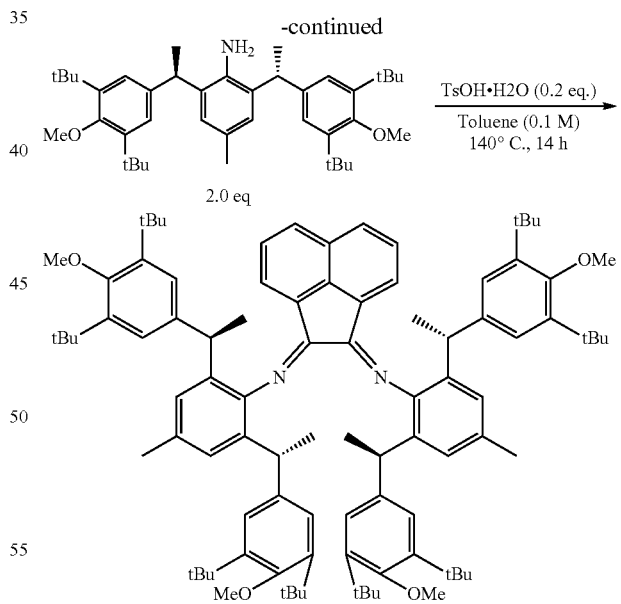

A 100 mL flask equipped with a stir bar was charged with 2, 6-bis ((R)-1-(3, 5-di-tert-butylphenyl-4-methoxyphenyl) ethyl)-4-methylaniline (2.1 g, 3.5 mmol), quinone (318 mg, 1.75 mmol), p-toluenesulfonic acid monohydrate (67 mg, 0.35 mmol) and 35 mL toluene. The mixture was refluxed with vigorous stirring at 140° C. for 14 h. The reaction vessel was allowed to cool to room temperature before suction filtration, and the crude diimine was used directly in the next step.

Synthesis of the 7,9-bis(2,6-bis((R)-1-(3,5-di-tert-butyl-4-methoxyphenyl)ethyl)-4-methylphenyl)-7H-acenaphtho[1,2-d]imidazol-9-ium chloride

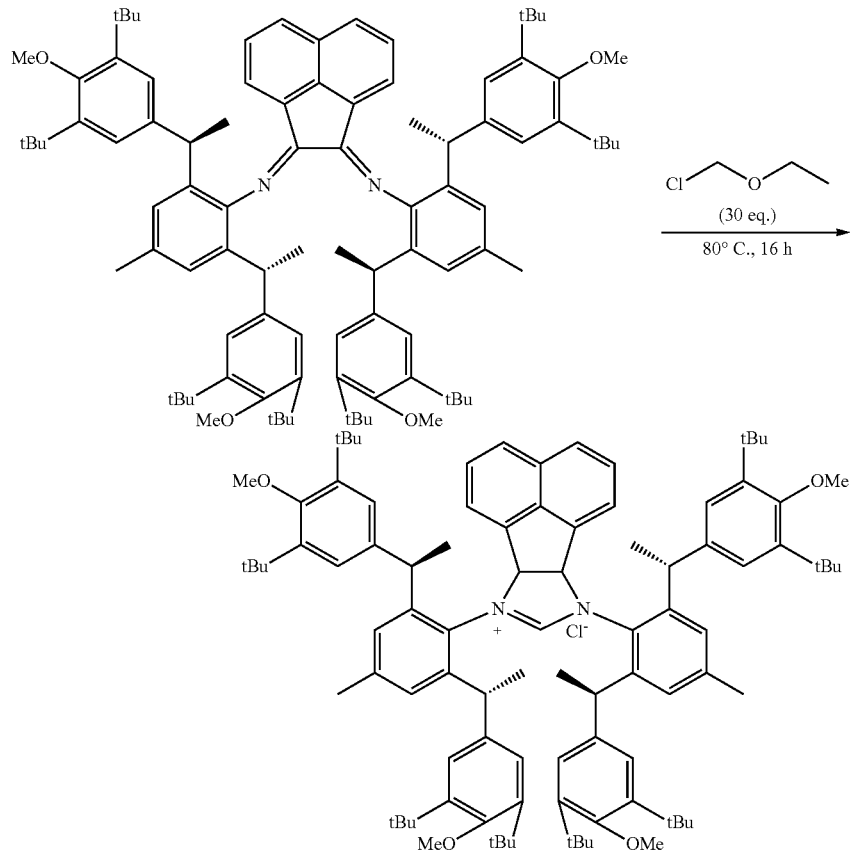

A 100 mL flask equipped with a stir bar was charged with the crude diimine, chloromethyl ether (1.5 g, 16 mmol). The mixture was refluxed with vigorous stirring at 80° C. for 24 h. The residue was purified by column chromatography to provide the title compound (312 mg, Yield=43%). $^1$H NMR (400 MHz, CDCl$_3$) δ 8.66 (s, 1H), 8.00 (d, J=8.3 Hz, 2H), 7.45 (dd, J=8.3, 7.1 Hz, 2H), 7.40 (d, J=1.8 Hz, 2H), 7.28 (s, 1H), 7.26 (s, 2H), 6.89 (d, J=7.0 Hz, 2H), 6.85 (s, 4H), 6.54 (s, 4H), 4.00 (q, J=7.0 Hz, 2H), 3.66 (s, 8H), 3.47 (s, 8H), 3.44 (s, 6H), 3.23 (q, J=7.0 Hz, 2H), 2.54 (s, 6H), 1.59 (d, J=7.1 Hz, 6H), 1.07 (d, J=7.1 Hz, 6H), 1.00 (s, 36H).

Example 12

Synthesis of the 1,3-bis(2,6-bis((R)-1-(3,5-diethylphenyl)ethyl)-4-methylphenyl)-4,5-dihydro-1H-imidazol-3-ium chloride

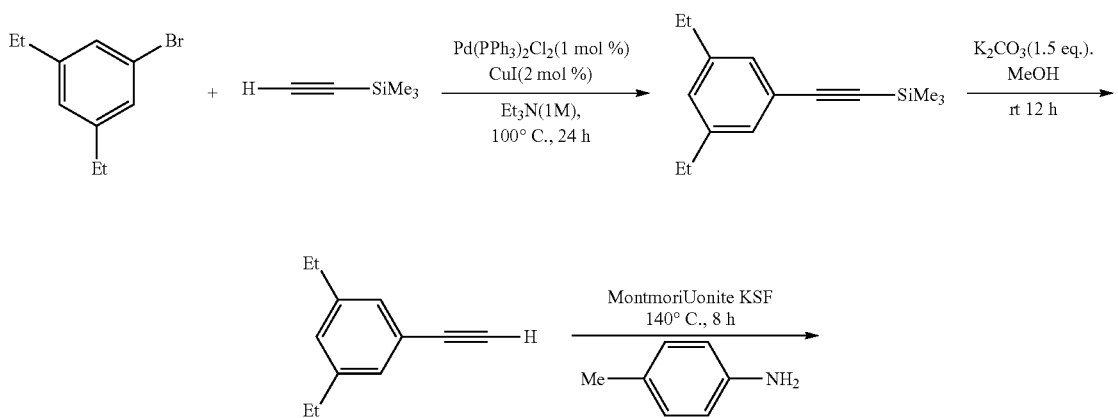

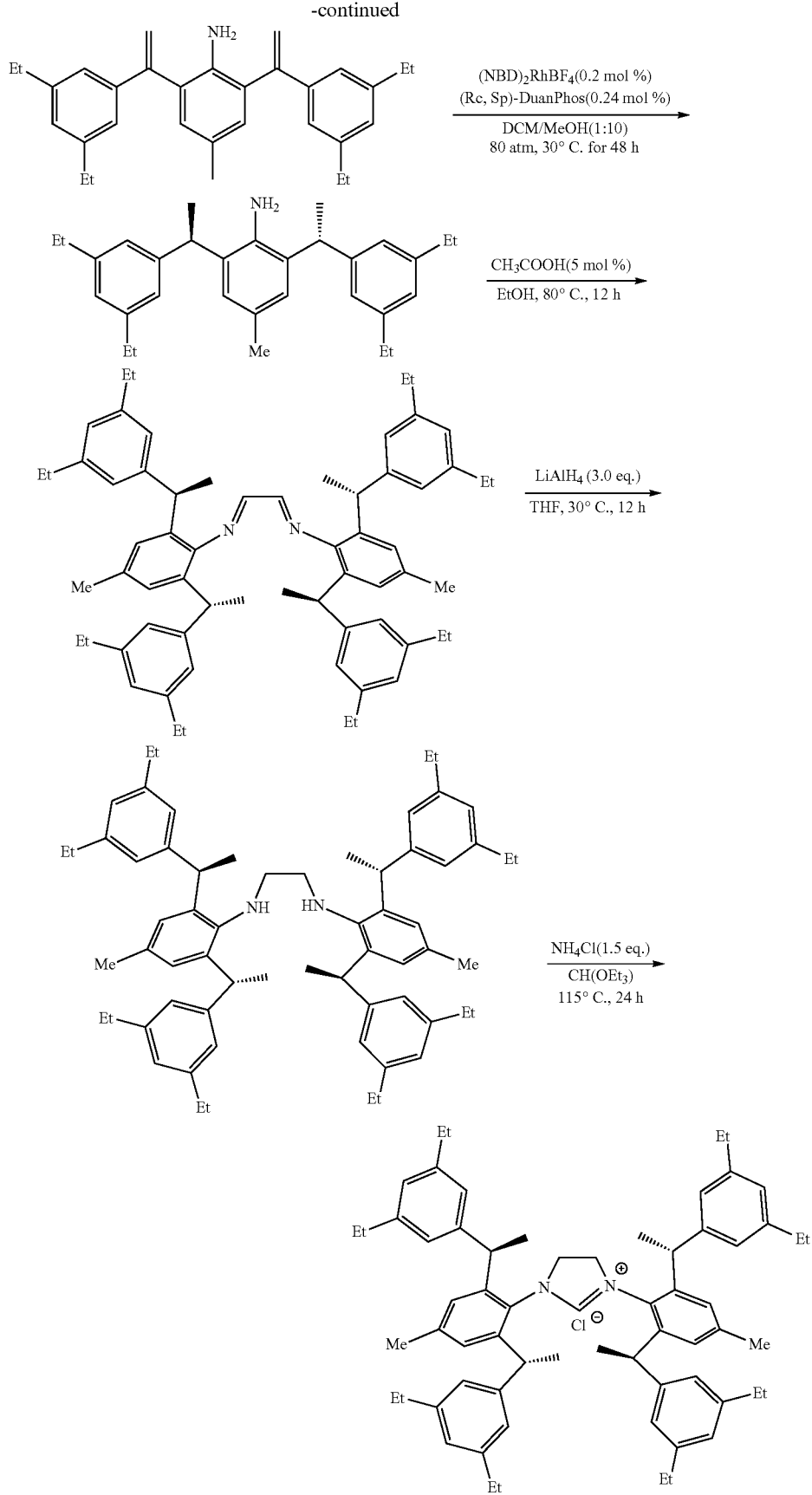

Synthesis of the ((3, 5-diethylphenyl) ethynyl) trimethylsilane

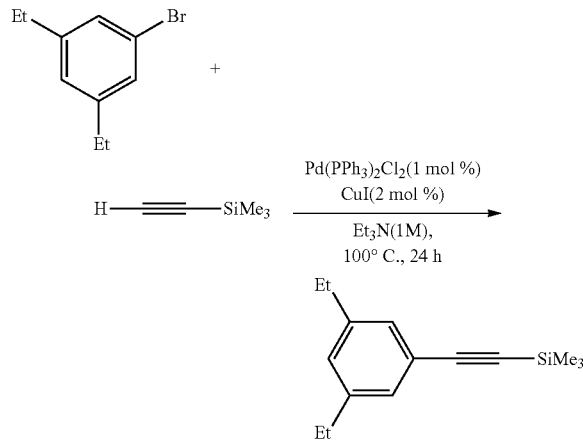

A 300 mL flask equipped with a stir bar was charged with 3, 5-diethylbromobenzene (53.1 g, 249 mmol), trimethylethynyl silicon (31.1 g, 323.7 mmol), cuprous iodide (1.9 g, 4 mmol %), bis (triphenylphosphine) palladium (II) chloride (3.5 g, 2 mmol) and 250 mL Et$_3$N. The mixture was stirred at 100° C. for 24 h and then cooled to room temperature. The crude product was purified by column chromatography (0-2% EtOAc in hexanes) to provide the title compound as a pale yellow liquid (54.6 g, Yield=95.3%). $^1$H NMR (400 MHz, CDCl$_3$) δ: 7.16 (s, 2H), 6.99 (s, 1H), 2.60 (q, J=7.6 Hz, 4H), 1.23 (t, J=7.6 Hz, 6H), 0.26 (s, 9H).

Synthesis of the 1, 3-diethyl-5-ethynylbenzene

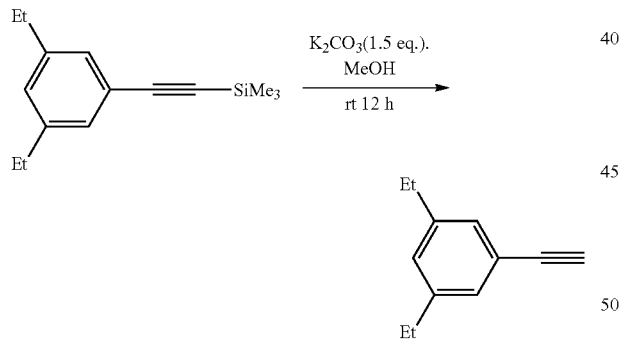

A 1 L flask equipped with a stir bar was charged with ((3, 5-diethylphenyl) ethynyl) trimethylsilane (57.27 g, 249 mmol, 1.0 equiv), 300 mL MeOH, K$_2$CO$_3$ (103.2 g, 747 mmol). The mixture was stirred at room temperature for 12 h. The MeOH solution was removed by concentrated, diluted with ether and the mixture was washed with brine, combined organic layer, and dried over Na$_2$SO$_4$. The crude product was purified by column chromatography to provide the title compound as a pale yellow liquid (36.5 g, Yield=94%). $^1$H NMR (400 MHz, CDCl$_3$) δ: 7.19 (s, 2H), 7.04 (s, 1H), 3.04 (s, 1H), 2.62 (q, J=7.6 Hz, 4H), 1.24 (t, J=7.6 Hz, 6H).

Synthesis of the 2, 6-bis (1-(3, 5-diethylphenyl) vinyl)-4-methylaniline

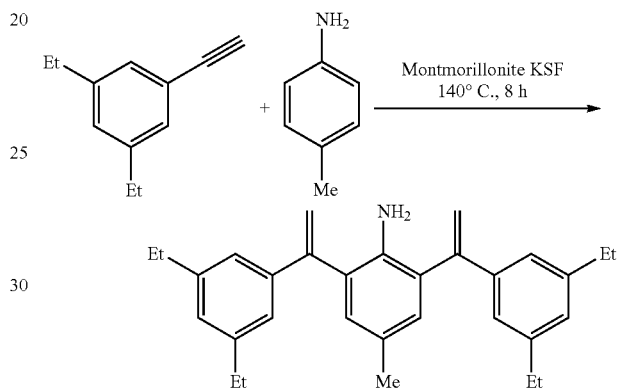

A 100 mL flask equipped with a stir bar was charged with p-methylaniline (10.7 g, 100 mmol, 1 eq.), KSF montmorillonite (10 g), and 1, 3-diethyl-5-ethynylbenzene (34.8 g, 220 mmol, 2.2 eq.). The reaction mixture was refluxed with vigorous stirring at 140° C. for 8 h. The reaction vessel was allowed to cool to room temperature before dilution with ethyl acetate and filtration. The solvent was removed from the mother liquor under reduced pressure, and the resultant was purified by column chromatography (0-2% EtOAc in hexanes) to provide the title compound as a white solid (13.05 g, Yield=30.8%). $^1$H NMR (400 MHz, CDCl$_3$) δ: 7.02 (d, J=1.7 Hz, 4H), 6.95 (d, J=1.0 Hz, 4H), 5.74 (d, J=1.7 Hz, 2H), 5.32 (d, J=1.7 Hz, 2H), 3.39 (s, 2H), 2.58 (q, J=7.6 Hz, 8H), 2.29 (s, 3H), 1.19 (t, J=7.6 Hz, 12H).

Synthesis of the 2, 6-bis ((R)-1-(3, 5-diethylphenyl) ethyl)-4-methylaniline

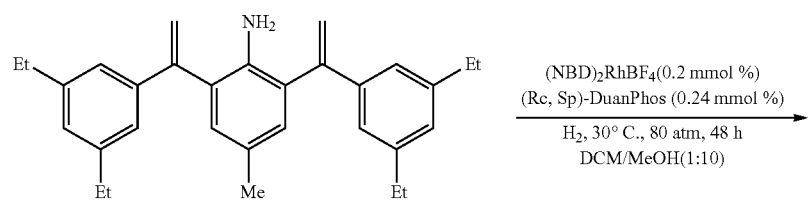

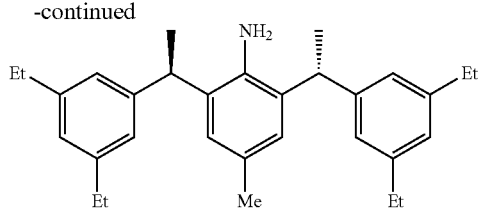

In a 100 mL microwave tube, (NBD)₂RhBF₄ (0.2 mol %) and (Rc,Sp)-DuanPhos (0.24 mol %) were dissolved in 6 mL DCM under a nitrogen atmosphere and stirred for 15 min. A solution of 2, 6-bis (1-(3, 5-diethylphenyl) vinyl)-4-methylaniline (7.3 g, 17.26 mmol, 1.0 equiv) in 60 mL MeOH was added. The microwave tube was transferred into the autoclave and the reactor was purged three times with $H_2$. The reactor was pressurized to 80 bar $H_2$ and the mixture was stirred at ambient temperature for 48 h. The solvent was removed under reduced pressure, and the residue was purified by column chromatography (0-2% EtOAc in hexanes) to provide the title compound as a yellow solid (7.1 g, Yield=96.3%). $^1$H NMR (400 MHz, CDCl₃) δ: 7.04 (s, 2H), 6.85 (d, J=1.6 Hz, 2H), 6.81 (d, J=1.5 Hz, 4H), 3.95 (q, J=7.1 Hz, 2H), 3.28 (s, 2H), 2.55 (q, 0.1=7.6 Hz, 8H), 2.39 (s, 3H), 1.58 (d, 0.1=7.2 Hz, 6H), 1.18 (t, 0.1=7.6 Hz, 12H). $^{13}$C NMR (101 MHz, CDCl₃) δ: 146.0, 144.6, 140.0, 130.3, 126.6, 126.3, 125.5, 124.4, 40.8, 28.9, 22.4, 21.4, 15.7.

Synthesis of the (1E,2E)-N¹,N²-bis(2,6-bis((R)-1-(3, 5-diethylphenyl)ethyl)-4-methylphenyl)ethane-1,2-diimine

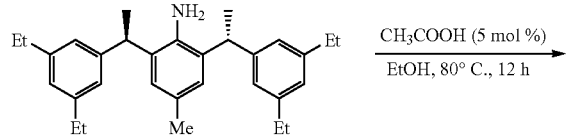

A 50 mL flask equipped with a stir bar was charged with 2, 6-bis ((R)-1-(3, 5-diethylphenyl) ethyl)-4-methylaniline (2.7 g, 6.23 mol) and 40 mL EtOH and was heated under reflux for 1 h. Drops of acetic acid (5 mol %) was then added. A 40% solution of glyoxal (0.5 eq) in water was added with the aid of a dropping funnel over a period of 30 min, and the resulting mixture was heated at 80° C. for further 12 h and then cooled to room temperature. The mixture was purified by column chromatography to provide the title compound as a yellow solid (2.23 g, Yield=81%). $^1$H NMR (400 MHz, CDCl₃) δ: 7.85 (s, 2H), 7.04 (s, 2H), 6.92 (s, 4H), 6.89-6.83 (m, 8H), 6.80 (d, 0.1=1.6 Hz, 2H), 4.06 (t, 0.1=6.9 Hz, 2H), 3.95 (q, 0.1=7.2 Hz, 2H), 2.55 (m, 16H), 2.28 (s, 6H), 1.58 (d, J=6.9 Hz, 6H), 1.49 (d, J=7.2 Hz, 6H), 1.22-1.13 (m, 24H).

Synthesis of the N¹, N²-bis (2, 6-bis ((R)-1-(3, 5-diethylphenyl) ethyl)-4-methylphenyl) ethane-1, 2-diamine

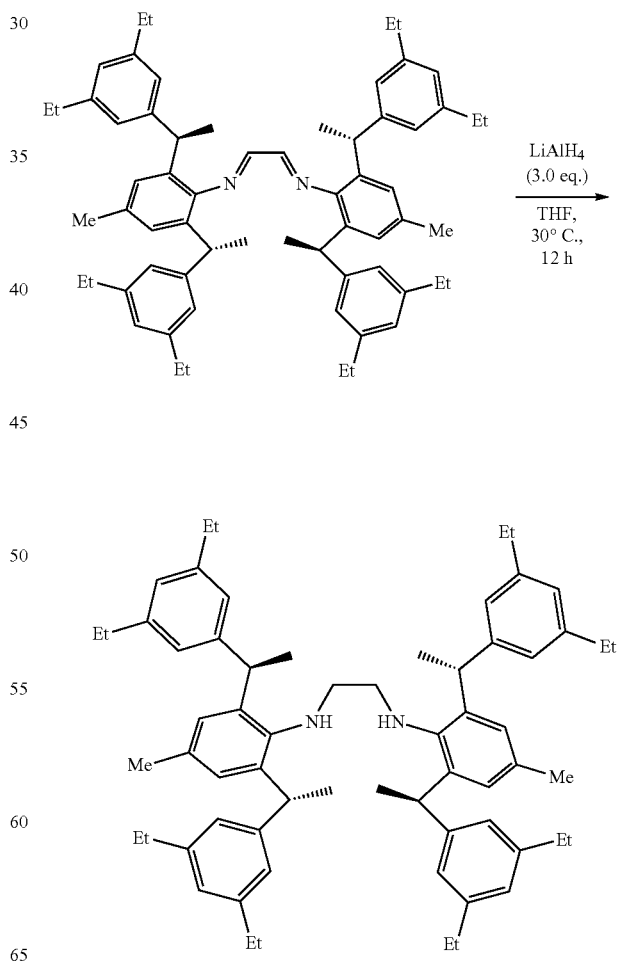

A 100 mL flask equipped with a stir bar was charged with (1E,2E)-N$^1$,N$^2$-bis(2,6-bis((R)-1-(3,5-diethylphenyl)ethyl)-4-methylphenyl)ethane-1,2-diimine (2.2 g, 2.51 mmol), 40 mL THF, and LiAlH$_4$ (3.0 eq) under a nitrogen atmosphere. The mixture was stirred for 12 h. Saturated KOH solution was added, and the mixture was extracted with EtOAc, combined organic layer and dried over Na$_2$SO$_4$. After filtration and concentration in vacuo, the residue was purified by column chromatography to afford the title compound (2.05 g, Yield=93%). $^1$H NMR (400 MHz, CDCl$_3$) δ: 6.90 (d, J=4.8 Hz, 4H), 6.81 (m, 12H), 4.42 (q, J=7.2 Hz, 4H), 2.88 (d, J=7.2 Hz, 2H), 2.59 (d, J=7.3 Hz, 2H), 2.49 (q, J=7.6 Hz, 16H), 2.26 (s, 6H), 1.54 (d, J=7.2 Hz, 12H), 1.12 (t, J=7.6 Hz, 24H).

Synthesis of the 1,3-bis(2,6-bis((R)-1-(3,5-diethylphenyl)ethyl)-4-methylphenyl)-4,5-dihydro-1H-imidazol-3-ium chloride

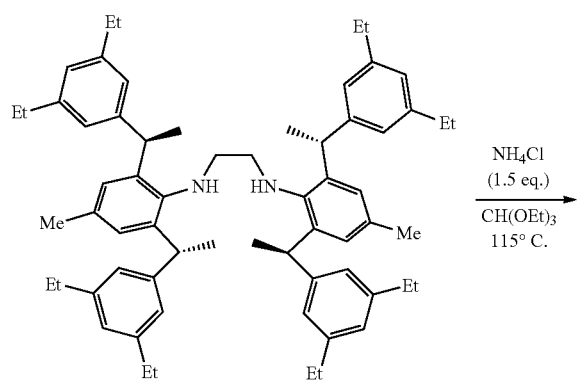

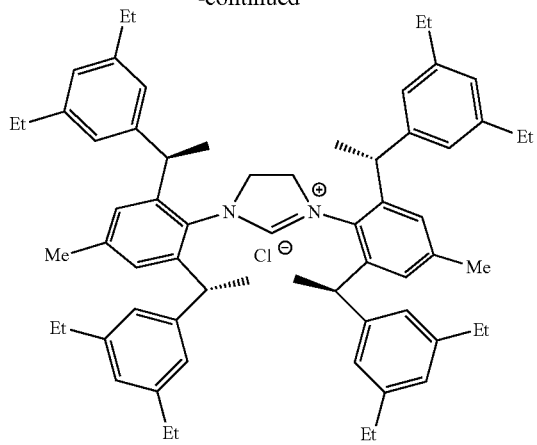

A 50 mL flask equipped with a stir bar was charged with N$^1$, N$^2$-bis (2, 6-bis ((R)-1-(3, 5-diethylphenyl) ethyl)-4-methylphenyl) ethane-1, 2-diamine (1.22 g, 1.38 mmol), NH$_4$Cl (111 mg, 2.07 mmol, 1.5 eq.) and 10 mL HC(OEt)$_3$ under a nitrogen atmosphere. The mixture was stirred at 115° C. for 15 h and then cooled to room temperature. The crude product was was purified by column chromatography to afford the title compound as a white solid (866 mg, Yield=67.6%). $^1$H NMR (400 MHz, CDCl$_3$) δ: 10.41 (s, 1H), 7.13 (m, 4H), 7.00-6.80 (m, 12H), 4.25 (q, J=7.0 Hz, 2H), 4.01 (q, J=6.8 Hz, 2H), 3.69-3.60 (m, 2H), 3.22-3.13 (m, 2H), 2.66-2.57 (m, 16H), 2.34 (s, 6H), 1.72 (d, J=7.0 Hz 6H), 1.37 (d, J=7.0 Hz, 6H), 1.21-1.14 (m, 24H).

Example 13

Synthesis of the 7,9-bis(2,6-bis((R)-1-(3,5-diethylphenyl)ethyl)-4-methylphenyl)-7H-acenaphtho[1,2-d]imidazol-9-ium chloride

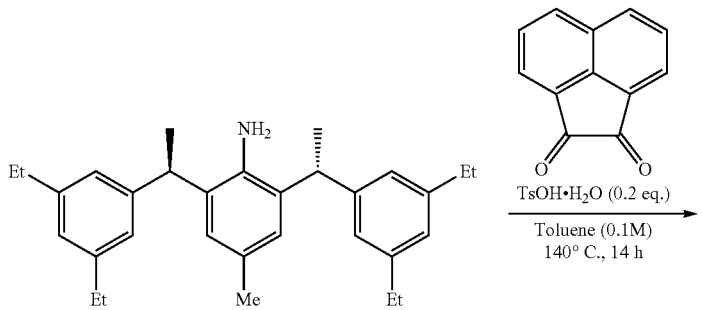

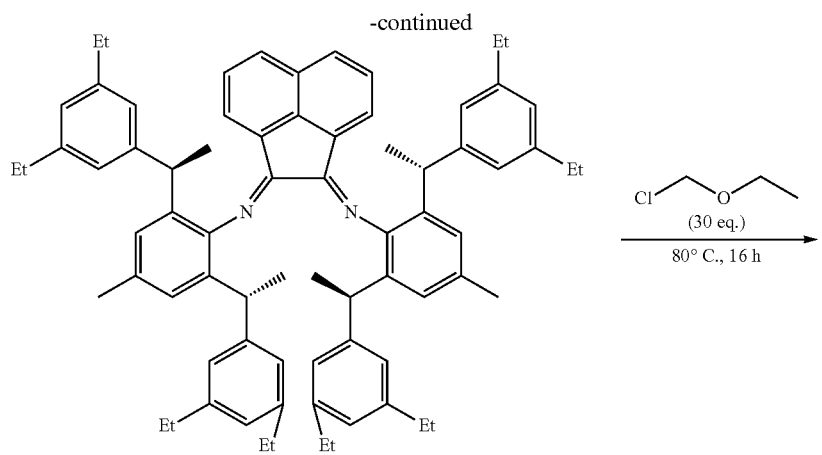

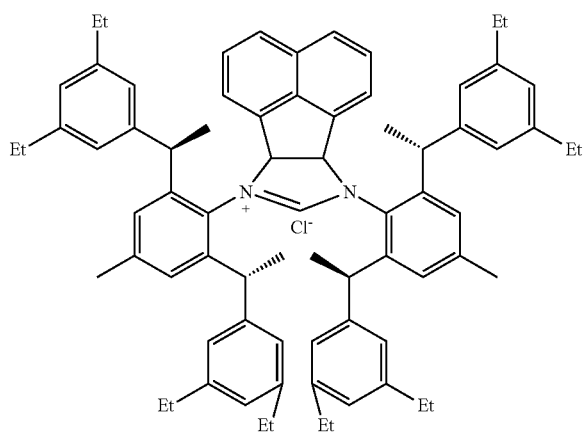

A 100 mL flask equipped with a stir bar was charged with 2,6-bis ((R)-1-(3,5-diethylphenyl) ethyl)-4-methylaniline (3 g, 7.0 mmol), quinone (609 mg, 3.3 mmol), p-toluenesulfonic acid monohydrate (251 mg, 1.32 mmol) and 30 mL toluene. The mixture was refluxed with vigorous stirring at 140° C. for 14 h. The reaction vessel was cooled to room temperature before suction filtration, and the crude diimine was used directly in the next step. A 100 mL flask equipped with a stir bar was charged with the crude diimine compound, chloromethyl ether (20 g, 210 mmol). The mixture was refluxed with vigorous stirring at 80° C. for 24 h. The residue was purified by column chromatography to provide the title compound (3.01 g, Yield=41%). $^1$H NMR (400 MHz, CDCl$_3$) δ: 10.08 (s, 1H), 7.80 (d, J=8.3 Hz, 2H), 7.43 (d, J=1.8 Hz, 2H), 7.25-7.09 (m, 6H), 6.90 (m, 8H), 6.60 (d, J=7.0 Hz, 2H), 6.17 (m, 2H), 4.06 (q, J=7.0 Hz, 4H), 2.59 (q, J=7.4 Hz, 16H), 2.53 (s, 6H), 1.59 (d, J=7.1 Hz, 12H), 1.14 (t, J=7.6 Hz, 24H).

APPLICATION EXAMPLES

In the following application examples, branched/linear ratio (rr) was determined by $^1$H NMR, GC, and GC-MS analysis.

Application Examples 1

Catalytic Asymmetric Hydroboration Reactions by Using Carbene Precursor 7:

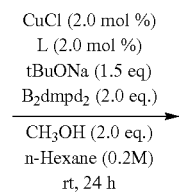

S1

CuCl (2.0 mol %)
L (2.0 mol %)
tBuONa (1.5 eq)
B$_2$dmpd$_2$ (2.0 eq.)
―――――――――→
CH$_3$OH (2.0 eq.)
n-Hexane (0.2M)
rt, 24 h

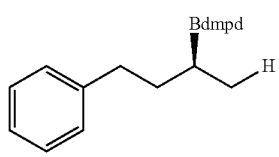

37a

L = 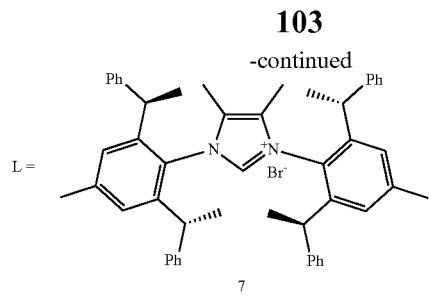

7

L = 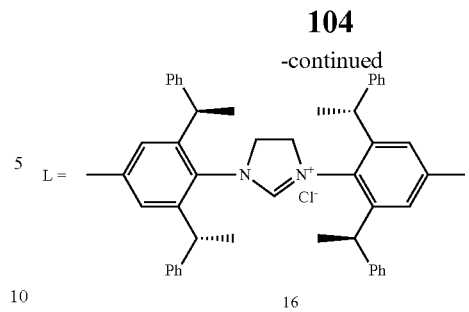

16

In a nitrogen-filled glove box, CuCl (0.4 mg, 0.004 mmol, 2.0 mol %), carbene precursor 7 (3.1 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (75:25 rr) was purified by column chromatography to provide the title compound as a colorless liquid in 61% yield. $^1$H NMR (400 MHz, CDCl$_3$) δ: 7.27 (t, J=7.1 Hz, 2H), 7.22-7.17 (m, 3H), 2.65-2.56 (m, 2H), 1.79-1.71 (m, 3H), 1.58-1.49 (m, 1H), 1.34-1.28 (m, 12H), 0.97 (d, J=6.4 Hz, 3H), 0.93-0.90 (m, 1H); $^{13}$C NMR (101 MHz, CDCl$_3$) δ: 143.77, 128.46, 128.13, 125.32, 69.99, 48.86, 35.81, 35.60, 31.83, 15.93. $[\alpha]_D^{20}$=+5.2° (c=0.25, CHCl3). HPLC (OD-H, 5% IPA in hexanes, 1 mL/min, 220 nm), ee=80%: tR (minor)=9.3 min, tR (major)=12.6 min. HRMS (ESI) calculated for $C_{17}H_{28}BO_2$ [M+H]$^+$ m/z 274.2213, found 274.2213.

Application Examples 2

Catalytic Asymmetric Hydroboration Reactions by Using Carbene Precursor 16:

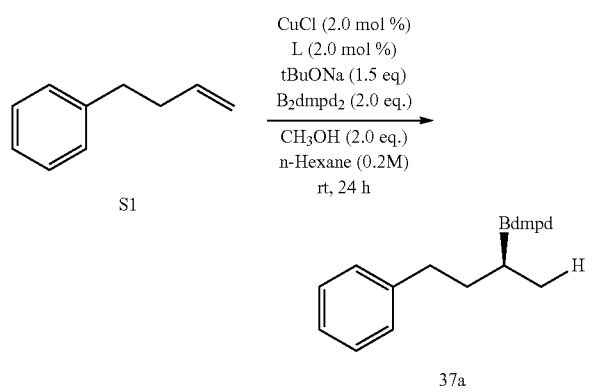

37a

In a nitrogen-filled glove box, CuCl (0.4 mg, 0.004 mmol, 2.0 mol %), carbene precursor 16 (2.9 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (79:21 rr) was purified by column chromatography to provide the title compound as a colorless liquid in 54% yield. HPLC (OD-H, 5% IPA in hexanes, 1 mL/min, 220 nm), ee=84%: tR (minor)=9.3 min, tR (major)= 12.6 min.

Application Examples 3

Catalytic asymmetric hydroboration reactions by using Cu/NHC complex 17:

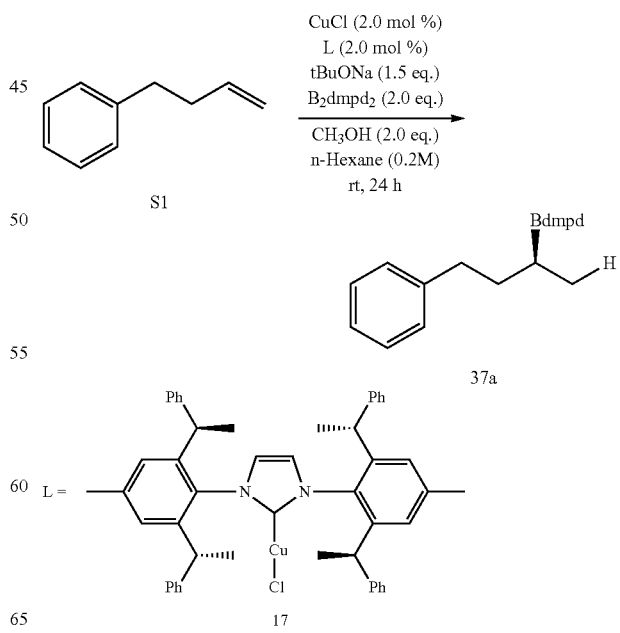

17

In a nitrogen-filled glove box, compound 17 (3.1 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (75:25 rr) was purified by column chromatography to provide the title compound as a colorless liquid in $6_5$% yield. HPLC (OD-H, 5% IPA in hexanes, 1 mL/min, 220 nm), ee=80%: $t_R$ (minor)=9.3 min, $t_R$ (major)= 12.6 min.

Application Examples 4

Catalytic Asymmetric Hydroboration Reactions by Using Carbene Precursor:

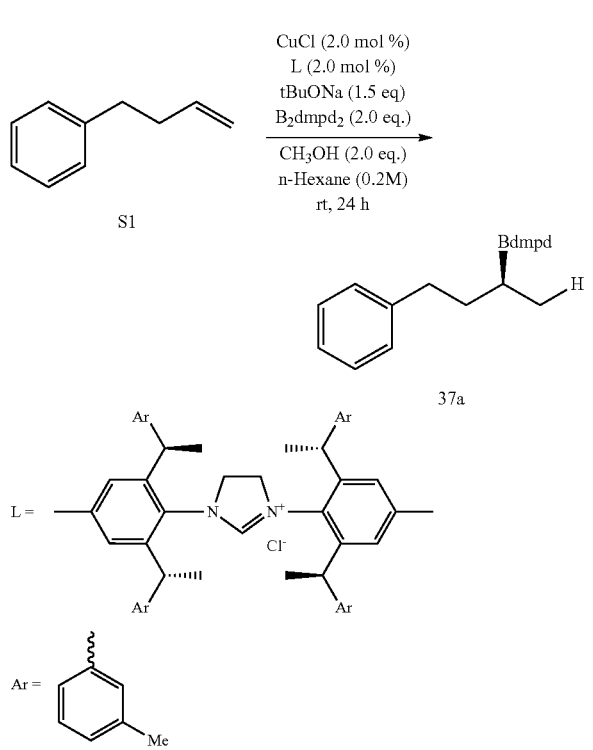

In a nitrogen-filled glove box, CuCl (0.4 mg, 0.004 mmol, 2.0 mol %), 1,3-bis (2,6-bis ((R)-1-(3-methylphenyl) ethyl)-2-methylphenyl)-4,5-dihydro-1H-imidazole chloride (3.2 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (82:18 rr) was purified by column chromatography to provide the title compound as a colorless liquid in 76% yield. HPLC (OD-H, 5% IPA in hexanes, 1 mL/min, 220 nm), ee=96%: $t_R$ (minor)=9.3 min, $t_R$ (major)= 12.6 min.

Application Examples 5

Catalytic Asymmetric Hydroboration Reactions by Using Carbene Precursor:

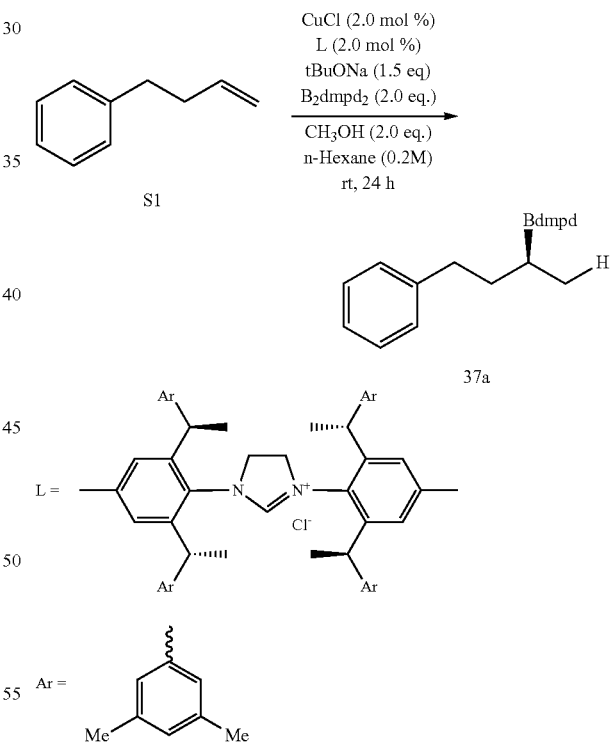

In a nitrogen-filled glove box, CuCl (0.4 mg, 0.004 mmol, 2.0 mol %), 1,3-bis (2,6-bis ((R)-1-(3,5-dimethylphenyl) ethyl)-2-methylphenyl)-4,5-dihydro-1H-imidazole chloride (3.2 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (86:14 rr) was purified by column chromatography to provide the title compound as a colorless liquid in 79% yield. HPLC (OD-H, 5% IPA in hexanes, 1 mL/min, 220 nm), ee=97%: $t_R$ (minor)=9.3 min, $t_R$ (major)= 12.6 min.

Application Examples 6

Catalytic Asymmetric Hydroboration Reactions by Using Carbene Precursor:

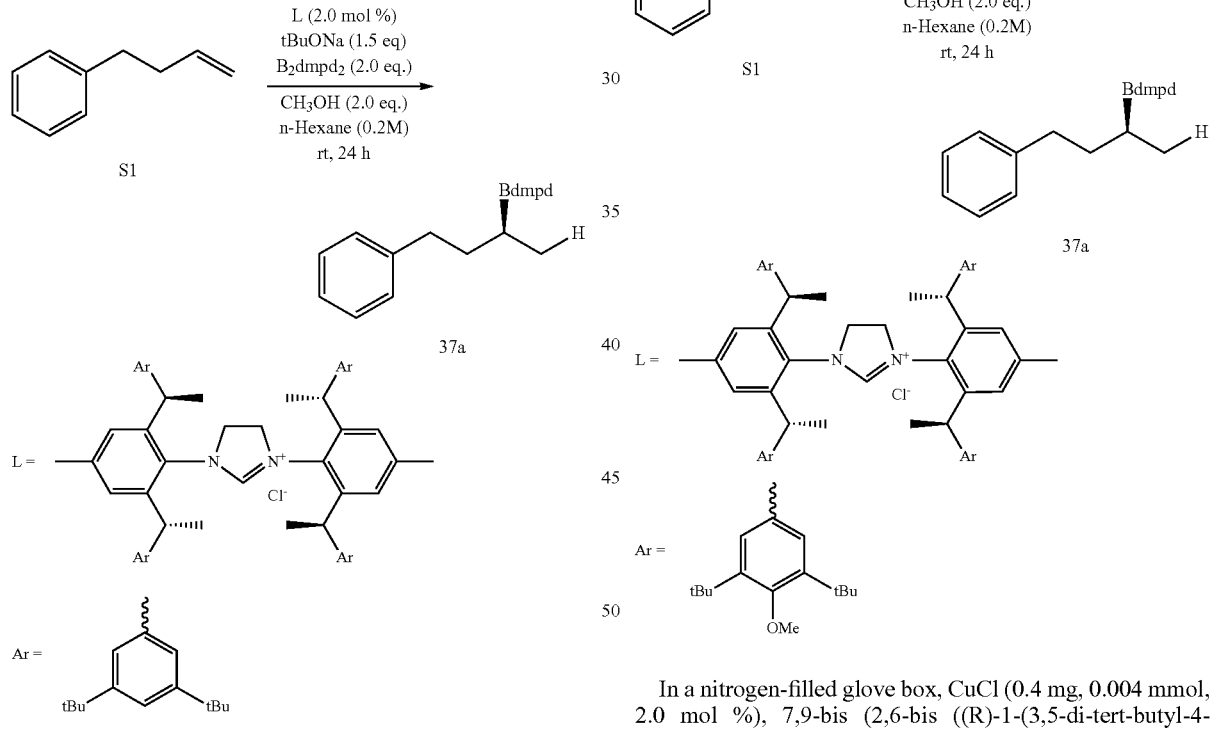

In a nitrogen-filled glove box, CuCl (0.4 mg, 0.004 mmol, 2.0 mol %), 1,3-bis (2,6-bis ((R)-1-(3,5-di-tert-butylphenyl) ethyl)-2-methylphenyl)-4,5-dihydro-1H-imidazole chloride (3.6 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (90:10 rr) was purified by column chromatography to provide the title compound as a colorless liquid in 80% yield. HPLC (OD-H, 5% IPA in hexanes, 1 mL/min, 220 nm), ee=97%: $t_R$ (minor)=9.3 min, $t_R$ (major)= 12.6 min.

Application Examples 7

Catalytic Asymmetric Hydroboration Reactions by Using Carbene Precursor:

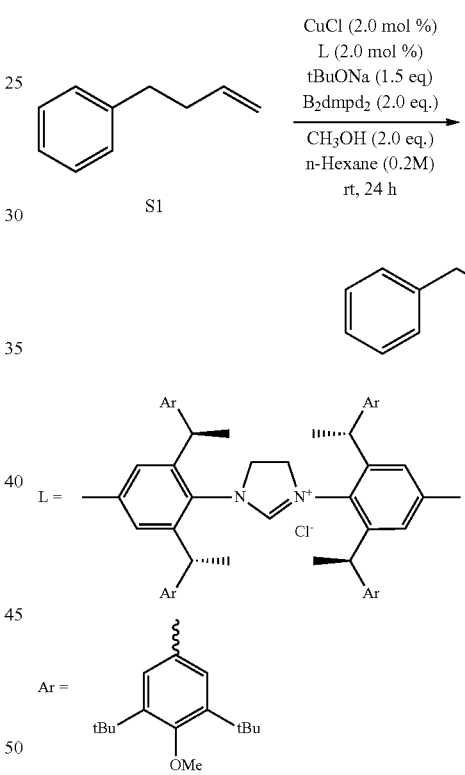

In a nitrogen-filled glove box, CuCl (0.4 mg, 0.004 mmol, 2.0 mol %), 7,9-bis (2,6-bis ((R)-1-(3,5-di-tert-butyl-4-methoxyphenyl) ethyl)-4-methylphenyl)-7H-Pyre [1,2-d] imidazole chloride (4.2 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (90:10 rr) was purified by column chromatography to provide the title compound as a colorless liquid in 80% yield. HPLC (OD-H, 5% IPA in hexanes, 1 mL/min, 220 nm), ee=97%: $t_R$ (minor)=9.3 min, $t_R$ (major)=12.6 min.

Application Examples 8

Catalytic Asymmetric Hydroboration Reactions by Using Carbene Precursor:

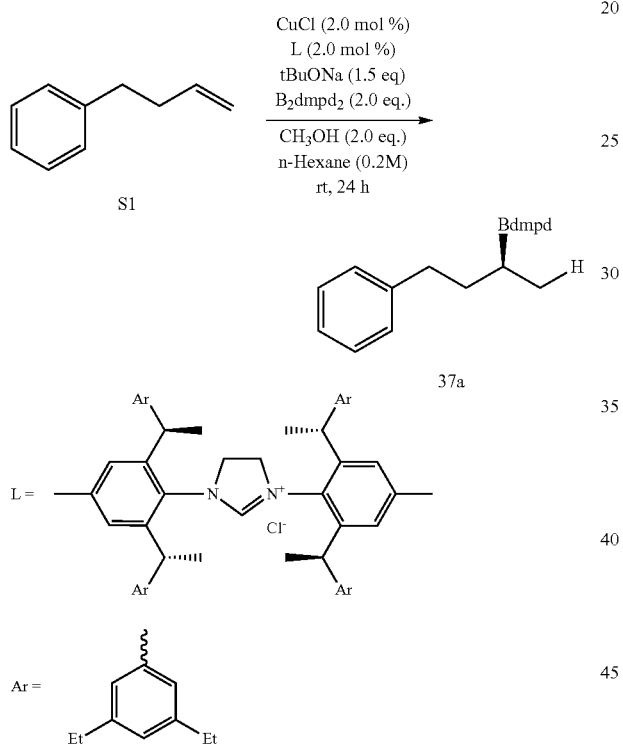

In a nitrogen-filled glove box, CuCl (0.4 mg, 0.004 mmol, 2.0 mol %), 1,3-bis (2,6-bis ((R)-1-(3,5-diethylphenyl) ethyl)-2-methylphenyl)-4,5-dihydro-1H-imidazole chloride (3.6 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee) values were determined by either chiral HPLC or SFC analysis following oxidation ($H_2O_2$/NaOH) of the isolated products unless otherwise stated.

The crude product (88:12 rr) was purified by column chromatography to provide the title compound as a colorless liquid in 78% yield. HPLC (OD-H, 5% IPA in hexanes, 1 mL/min, 220 nm), ee=96%: $t_R$ (minor)=9.3 min, $t_R$ (major)=12.6 min.

Application Examples 9

Catalytic Asymmetric Hydroboration Reactions by Using Carbene Precursor:

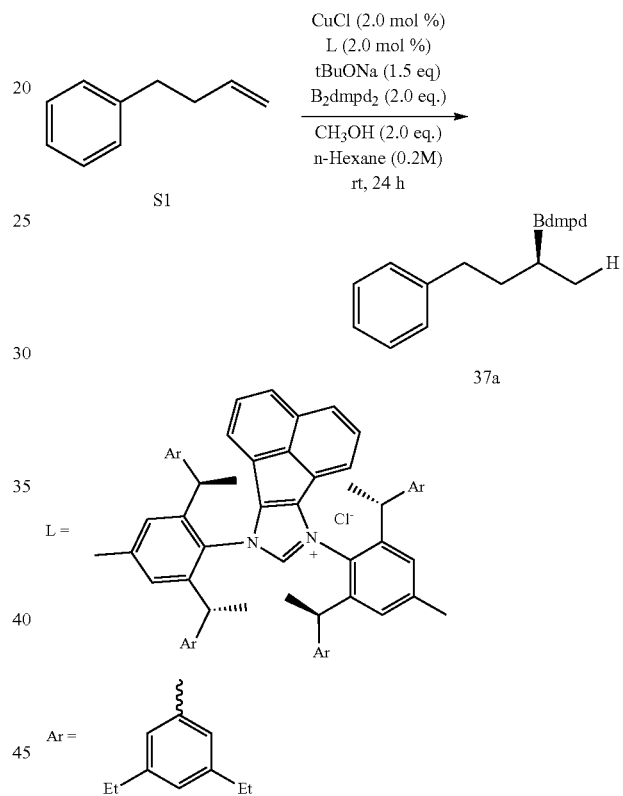

In a nitrogen-filled glove box, CuCl (0.4 mg, 0.004 mmol, 2.0 mol %), 7,9-bis (2,6-bis ((R)-1-(3,5-diethylphenyl) ethyl)-4-methylphenyl)-7H-pyrene [1,2-d] imidazole chloride (4.1 mg, 0.004 mmol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of $B_2dmpd_2$ (113 mg, 0.4 mmol, 2.0 equiv). Stirring was continued for an additional 0.5 h at rt. The unactivated terminal alkene S1 (26.4 mg, 0.2 mmol) and MeOH (16 uL, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography (PE:EA=40:1) to afford the desired product 37a. Enantiomeric excess (ee)

values were determined by either chiral HPLC or SFC analysis following oxidation (H₂O₂/NaOH) of the isolated products unless otherwise stated.

The crude product (88:12 rr) was purified by column chromatography to provide the title compound as a colorless liquid in 80% yield. HPLC (OD-H, 5% IPA in hexanes, 1 mL/min, 220 nm), ee=97%: $t_R$ (minor)=9.3 min, $t_R$ (major)= 12.6 min.

Application Examples 10

Synthesis of the (R,R,R,R)-ANIPE-CuCl (compound 35)

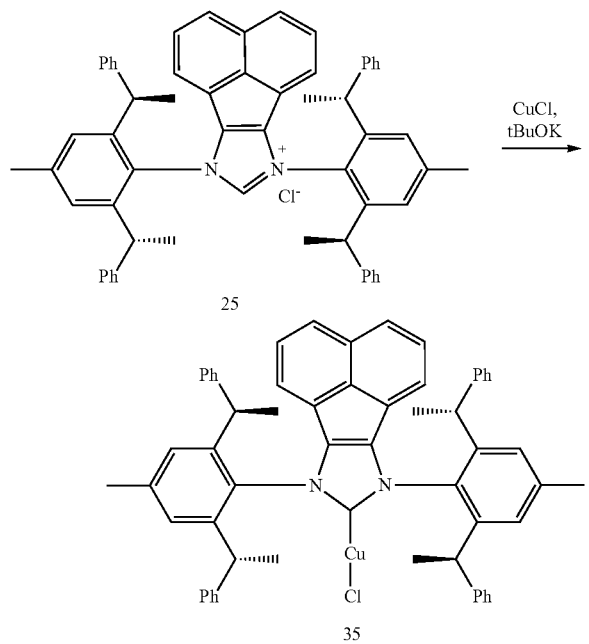

CuCl (100 mg, 1.0 mmol, 1.0 equiv), tBuOK (112 mg, 1.0 mmol, 1.0 equiv), (R,R,R,R)-ANIPE/HCl compound 25 (824 mg, 1.0 mmol, 1.0 equiv) and THF (5 mL) were added to a flame-dried Schlenk tube. The mixture was stirred at rt for 12 h. The reaction mixture was filtered through a short pad of Celite, and the solvent was removed in vacuo. The crude product was purified by flash column chromatography (DCM) to provide the title compound as a yellow powder in 90% yield (779 mg). Melting point: 159-160° C. IR: 2967, 2920, 1603, 1490, 1446, 1064, 756, 700; ¹H NMR (400 MHz, CDCl₃) δ: 7.70 (d, J=8.2 Hz, 2H), 7.41 (d, J=7.5 Hz, 4H), 7.33 (t, 0.1=7.4 Hz, 4H), 7.27 (t, 0.1=7.7 Hz, 2H), 7.22-7.15 (m, 4H), 7.03 (s, 2H), 6.83-6.70 (m, 12H), 4.24 (q, J=6.3 Hz, 2H), 3.96 (q, J=6.5 Hz, 2H), 2.40 (s, 6H), 1.49 (dd, J=13.3, 7.0 Hz, 12H). ¹³C NMR (101 MHz, CDCl₃) δ: 186.13, 144.85, 143.92, 143.60, 143.20, 140.58, 139.05, 131.99, 130.38, 129.26, 128.77, 128.00, 127.91, 127.77, 127.48, 127.31, 127.14, 126.41, 125.81, 124.85, 121.43, 39.78, 38.39, 22.64, 21.88, 21.62. $[\alpha]_D^{20}$=+251.2° (c=0.90, CHCl₃). HRMS (ESI) calculated for $C_{59}H_{52}N_2ClCu$ [M]⁺ m/z 886.3110, found 886.3105.

Synthesis of the Single Crystal of (R,R,R,R)-ANIPE-CuCl (Compound 35)

(R,R,R,R)-ANIPE-CuCl (10 mg) was dissolved in 2 ml ether and sonicated for 1 min. Filtered with cotton into an 8 ml vial. After sealing the membrane tightly, pierce 3 to 5 small holes with a capillary. The vial was carefully placed in a wide-mouth bottle containing n-pentane. After standing for one week, the square crystals were taken out under a microscope and tested for single crystals. FIG. 1 shows the single-crystal diffraction pattern of compound 35.

Example 11

Catalytic Asymmetric Markovnikov Hydroboration of α-Olefins

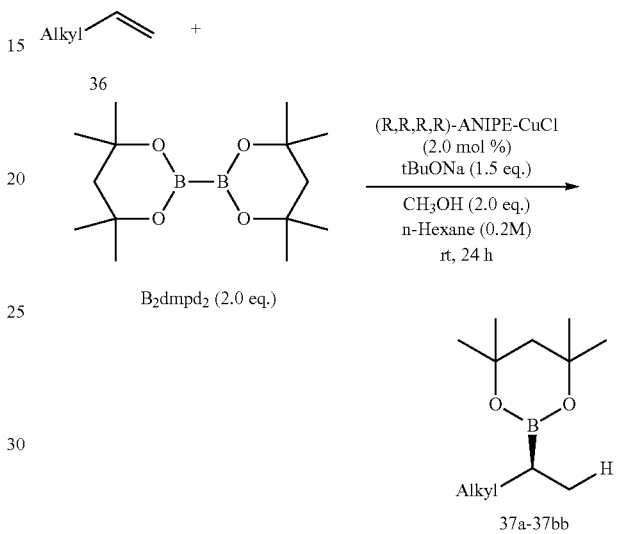

In a nitrogen-filled glove box, (R,R,R,R)-ANIPE-CuCl (3.4 mg, 4 mol, 2.0 mol %), tBuONa (28.8 mg, 0.3 mmol, 1.5 equiv) and n-hexane (1.0 mL) were charged to a 8 ml vial equipped with a magnetic stirrer bar. The reaction mixture was allowed to stir at rt for 1 h, followed by addition of B₂dmpd₂ (113 mg, 0.4 mmol, 2.0 equiv). Stirring was continued for an additional 0.5 h at rt. The alkene (0.2 mmol) and MeOH (16 L, 0.4 mmol, 2.0 equiv) were then added. The reaction vial was removed from the glove box, and the reaction mixture was stirred within the sealed vial at rt for 24 h. The resulting mixture was then filtered through a short pad of silica gel, eluting with EtOAc. The branched/linear ratio (rr) was determined by GC-MS analysis at this stage. The solvent was removed in vacuo, and the crude residue was purified via column chromatography to afford the desired product. Enantiomeric excess (ee) values were determined by either chiral HPLC or SFC analysis following oxidation (H₂O₂/NaOH or NaBO₃) of the isolated products unless otherwise stated.

Compound 37a

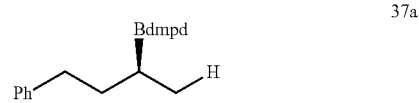

The regioselectivity of the crude product is (Markov:anti-Markov) 80:20, anhydrous oil, yield=67%, ¹H NMR (400 MHz, CDCl₃) δ: 7.27 (t, J=7.1 Hz, 2H), 7.22-7.17 (m, 3H), 2.65-2.56 (m, 2H), 1.79-1.71 (m, 3H), 1.58-1.49 (m, 1H), 1.34-1.28 (m, 12H), 0.97 (d, J=6.4 Hz, 3H), 0.93-0.90 (m, 1H); $^{13}$C NMR (101 MHz, CDCl$_3$) δ: 143.77, 128.46, 128.13, 125.32, 69.99, 48.86, 35.81, 35.60, 31.83, 15.93. $[α]_D^{20}$=+5.2° (c=0.25, CHCl$_3$). HPLC (OD-H, 5% IPA in hexanes, 1 mL/min, 220 nm), ee=96%: $t_R$ (minor)=9.3 min, $t_R$ (major)=12.6 min. HRMS (ESI) calculated for C$_{17}$H$_{28}$BO$_2$ [M+H]$^+$ 274.2213, found 274.2213.

Compound 37b

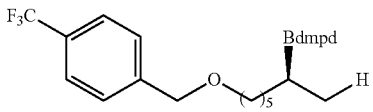

The regioselectivity of the crude product is (Markov:anti-Markov) 81:19, yellow oil, yield=50%, $^1$H NMR (400 MHz, CDCl$_3$) δ: 7.58 (d, J=8.0 Hz, 2H), 7.44 (d, J=8.0 Hz, 2H), 4.54 (s, 2H), 3.47 (t, J=6.6 Hz, 2H), 1.75 (s, 2H), 1.67-1.54 (m, 2H), 1.46-1.33 (m, 4H), 1.29 (s, 12H), 1.26-1.16 (m, 2H), 0.88 (d, J=7.0 Hz, 3H), 0.84-0.74 (m, 1H); $^{13}$C NMR (101 MHz, CDCl$_3$) δ: 142.91, 127.42, 125.24, 125.20, 71.98, 71.02, 69.85, 48.85, 33.39, 31.75, 29.72, 28.81, 26.43, 15.91. $[α]_D^{20}$=+3.8° (c=0.4, CHCl$_3$). HPLC (IA, 2% IPA in hexanes, 0.8 mL/min, 220 nm) ee=92%: $t_R$ (major)=21.2 min, $t_R$ (minor)=22.2 min. HRMS (ESI) calculated for C$_{22}$H$_{38}$BO$_3$NF$_3$ [M+NH$_4$]$^+$ 431.2928, found 431.2922.

Compound 37c

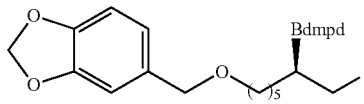

The regioselectivity of the crude product is (Markov:anti-Markov) 86:14, yellow oil, yield=67%. $^1$H NMR (400 MHz, CDCl$_3$) δ: 6.84 (s, 1H), 6.78-6.77 (m, 2H), 5.93 (s, 2H), 4.38 (s, 2H), 3.41 (t, J=6.7 Hz, 2H), 1.75 (s, 2H), 1.63-1.53 (m, 2H), 1.45-1.30 (m, 4H), 1.29 (s, 12H), 1.26-1.13 (m, 2H), 0.87 (d, J=7.0 Hz, 3H), 0.83-0.72 (in, 1H); $^{13}$C NMR (101 MHz, CDCl$_3$) δ: 147.66, 146.91, 132.64, 121.11, 108.39, 107.97, 104.99, 100.87, 72.69, 70.42, 69.84, 48.86, 33.41, 31.77, 29.76, 28.85, 26.47, 15.92. $[α]_D^{20}$=+4.5° (c=0.24, CHCl$_3$). HPLC (IA, 2% IPA in hexanes, 0.8 mL/min, 220 nm) ee=91%: $t_R$ (major)=44.2 min, $t_R$ (minor)=46.3 min. HRMS (ESI) calculated for C$_{22}$H$_{39}$BNO$_5$ [M+NH$_4$] 407.2952, found 407.2948.

Compound 37d

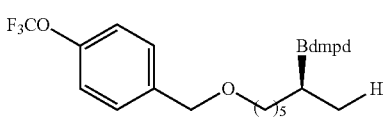

The regioselectivity of the crude product is (Markov:anti-Markov) 84:16, colorless oil, yield=61%; $^1$H NMR (400 MHz, CDCl$_3$) δ: 7.35 (d, J=8.4 Hz, 2H), 7.17 (d, J=8.1 Hz, 2H), 4.47 (s, 2H), 3.46 (t, J=6.7 Hz, 2H), 1.75 (s, 2H), 1.65-1.58 (m, 2H), 1.46-1.33 (m, 4H), 1.29 (s, 12H), 1.26-1.15 (m, 2H), 0.88 (d, J=6.9 Hz, 3H), 0.84-0.72 (m, 1H); $^{13}$C NMR (101 MHz, CDCl$_3$) δ: 148.48, 137.54, 128.81, 120.84, 71.91, 70.89, 69.84, 48.85, 33.39, 31.75, 29.73, 28.82, 26.44, 15.90. $[α]_D^{20}$=+3.6° (c=0.34, CHCl$_3$). HPLC (IA, 2% IPA in hexanes, 0.8 mL/min, 220 nm) ee=90%: $t_R$ (major)=18.4 min, $t_R$(minor)=19.2 min. HRMS (ESI) calculated for C$_{22}$H$_{38}$BF$_3$NO$_4$ [M+NH$_4$]$^+$ 447.2877, found 447.2877.

Compound 37e

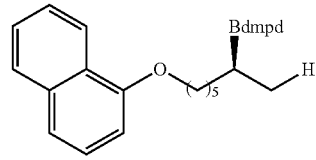

The regioselectivity of the crude product is (Markov:anti-Markov) 83:17, colorless oil, yield=74%; $^1$H NMR (400 MHz, CDCl$_3$) δ: 8.31 (d, J=6.8 Hz, 1H), 7.79 (d, J=8.4 Hz, 1H), 7.51-7.44 (m, 2H), 7.43-7.32 (m, 2H), 6.80 (d, 0.1=7.3 Hz, 1H), 4.13 (t, 0.1=6.4 Hz, 2H), 1.98-1.89 (m, 2H), 1.76 (s, 2H), δ 1.60-1.50 (m, 2H), 1.52-1.33 (m, 4H), 1.30 (s, 12H), 0.93 (d, J=6.8 Hz, 3H), 0.90-0.85 (m, 1H); $^{13}$C NMR (101 MHz, CDCl$_3$) δ: 154.94, 134.48, 127.35, 126.25, 125.89, 125.78, 124.98, 122.15, 119.83, 104.49, 69.89, 68.19, 48.87, 33.45, 31.79, 29.34, 28.83, 26.55, 15.98. $[α]_D^{20}$=+5.1° (c=0.11, CHCl$_3$). SFC (OD, 10% IPA in CO$_2$, 1.3 mL/min, 214 nm) ee=95%: $t_R$ (major)=30.9 min, $t_R$ (minor)=32.3 min. HRMS (ESI) calculated for C$_{24}$H$_{39}$BNO$_3$ [M+NH$_4$]$^+$399.3054, found 399.3053.

Compound 37f:

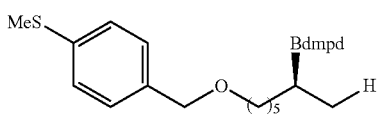

The regioselectivity of the crude product is (Markov:anti-Markov) 85:15, yellow oil, yield=63%; $^1$H NMR (400 MHz, CDCl$_3$) δ: 7.24 (s, 4H), 4.44 (s, 2H), 3.43 (t, J=6.7 Hz, 2H), 2.47 (s, 3H), 1.75 (s, 2H), 1.66-1.53 (m, 2H), 1.46-1.31 (m, 3H), 1.29 (s, 12H), 1.26-1.11 (m, 3H), 0.87 (d, J=7.1 Hz, 3H), 0.83-0.72 (m, 1H); $^{13}$C NMR (101 MHz, CDCl$_3$) δ: 137.38, 135.73, 128.21, 126.74, 72.38, 70.59, 69.85, 48.86, 33.41, 31.78, 29.77, 28.85, 26.47, 16.05, 15.92. $[α]_D^{20}$=+4.2° (c=0.27, CHCl$_3$). HPLC (IA, 2% IPA in hexanes, 0.8 mL/min, 220 nm) ee=90%: $t_R$ (major)=41.5 min, $t_R$ (minor)=43.1 min. HRMS (ESI) calculated for C$_{22}$H$_{41}$O$_3$BNS [M+NH$_4$]$^+$409.2923, found 409.2931.

Compound 37g

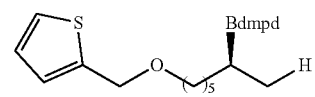

The regioselectivity of the crude product is (Markov:anti-Markov) 86:14, yellow oil, yield=53%; $^1$H NMR (400 MHz, CDCl$_3$) δ: 7.26 (d, 0.1=4.9 Hz, 1H), 6.96 (d, 0.1=7.5 Hz, 2H), 4.64 (s, 2H), 3.46 (t, 0.1=6.7 Hz, 2H), 1.75 (s, 2H), 1.60-1.55 (m, 2H), 1.46-1.30 (m, 4H), 1.29 (s, 12H), 1.26-1.14 (m, 2H), 0.87 (d, J=7.2 Hz, 3H), 0.83-0.74 (m, 1H); $^{13}$C NMR (101 MHz, CDCl$_3$) δ: 141.57, 126.52, 126.02, 125.50, 70.36, 69.84, 67.27, 48.86, 33.41, 31.78, 29.68, 28.84, 26.41, 15.92. $[\alpha]_D^{20}$=+5.3° (c=0.41, CHCl$_3$). HPLC (AS-H, 5% IPA in hexanes, 1 mL/min, 220 nm) ee=95%: $t_R$ (major)= 6.8 min, $t_R$ (minor)=10.1 min. HRMS (ESI) calculated for C$_{19}$H$_{37}$BNO$_3$S[M+NH$_4$]$^+$369.2618, found 369.2615.

Compound 37h

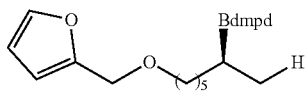

The regioselectivity of the crude product is (Markov:anti-Markov) 83:17, anhydrous oil, yield=53%; $^1$H NMR (400 MHz, CDCl$_3$) δ: $^1$H NMR (400 MHz, CDCl$_3$) δ: 7.38 (d, J=0.9 Hz, 1H), 6.31 (d, J=1.8 Hz, 1H), 6.28 (d, J=3.0 Hz, 1H), 4.42 (s, 2H), 3.44 (t, J=6.8 Hz, 2H), 1.75 (s, 2H), 1.62-1.54 (m, 3H), 1.38 m, 2H), 1.28 (s, 12H), 1.26-1.11 (m, 3H), 0.86 (d, J=7.0 Hz, 3H), 0.80-0.77 m, 1H); $^{13}$C NMR (101 MHz, CDCl$_3$) δ: 152.15, 142.56, 110.14, 108.85, 104.99, 100.24, 70.58, 69.84, 64.69, 48.85, 33.39, 31.77, 29.62, 28.81, 26.36, 15.90. $[\alpha]_D^{20}$=+4.9° (c=0.25, CHCl$_3$). HPLC (AS-H, 5% IPA in hexanes, 1 mL/min, 220 nm) ee=92%: $t_R$ (major)=7.2 min, $t_R$ (minor)=11.9 min. HRMS (ESI) calculated for C$_{19}$H$_{37}$O$_4$BN [M+NH$_4$]$^+$ 353.2846, found 353.2844.

Compound 37i

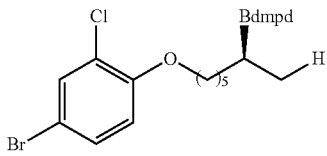

The regioselectivity of the crude product is (Markov:anti-Markov) 85:15, anhydrous oil, yield=50%; $^1$H NMR (400 MHz, CDCl$_3$) δ: 7.48 (t, J=2.7 Hz, 1H), 7.33-7.22 (m, 1H), 6.77 (d, J=8.8 Hz, 1H), 3.98 (t, 0.1=6.6 Hz, 2H), 1.87-1.77 (m, 2H), 1.76 (s, 2H), 1.51-1.39 (m, 4H), 1.29 (s, 12H), 1.27-1.17 (m, 2H), 0.89 (d, J=6.9 Hz, 3H), 0.85-0.77 (m, 1H); $^{13}$C NMR (101 MHz, CDCl$_3$) δ: 153.97, 132.54, 130.35, 123.99, 114.42, 112.09, 69.88, 69.44, 48.83, 33.30, 31.77, 28.96, 28.64, 26.11, 15.92. $[\alpha]_D^{20}$=+4.4° (c=0.36, CHCl$_3$). HPLC analysis (AS-H, 1% IPA in hexanes, 1 mL/min, 254 nm) indicated 92% ee: $t_R$ (major)=13.7 min, $t_R$ (minor)=15.6 min. HRMS (EI) calculated for C$_{20}$H$_{31}$O$_3$BClBr [M]$^+$ m/z 443.1274, found 443.1283.

Compound 37j

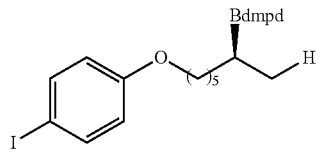

The regioselectivity of the crude product is (Markov:anti-Markov) 82:18, anhydrous oil, yield=55%; $^1$H NMR (400 MHz, CDCl$_3$) δ: 7.51 (d, 0.1=7.6 Hz, 2H), 6.64 (d, 0.1=7.7 Hz, 2H), 3.88 (t, 0.1=6.6 Hz, 2H), 1.77-1.70 (m, 4H), 1.45-1.31 (m, 5H), 1.28 (s, 12H), 1.25-1.18 (m, 1H), 0.87 (d, J=7.1 Hz, 3H), 0.84-0.73 (m, 1H); $^{13}$C NMR (101 MHz, CDCl$_3$) δ: 159.01, 138.07, 116.90, 104.99, 82.27, 69.87, 68.15, 48.83, 33.33, 31.77, 29.10, 28.67, 26.20, 15.94. $[\alpha]_D^{20}$=+4.9° (c=0.78, CHCl$_3$). HPLC (OD-H, 1% IPA in hexanes, 1 mL/min, 220 nm) ee=94%: $t_R$ (minor)=44.3 min, $t_R$ (major)=47.8 min. HRMS (EI) calculated for C$_{20}$H$_{32}$O$_3$BI [M]$^+$ 457.1526, found 457.1521.

Compound 37k

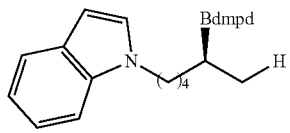

The regioselectivity of the crude product is (Markov:anti-Markov) 84:16, anhydrous oil, yield=60%; $^1$H NMR (400 MHz, CDCl$_3$) δ: 7.63 (d, J=7.9 Hz, 1H), 7.36 (d, J=8.4 Hz, 1H), 7.20 (t, J=7.6 Hz, 1H), 7.14-7.02 (m, 2H), 6.48 (s, 1H), 4.11 (t, J=7.1 Hz, 2H), 1.89-1.78 (m, 2H), 1.73 (s, 2H), 1.51-1.41 (m, 1H), 1.40-1.29 (m, 3H), 1.27 (s, 12H), 0.90 (d, J=7.0 Hz, 3H), 0.86-0.81 (m, 1H); $^{13}$C NMR (101 MHz, CDCl$_3$) δ: 135.95, 128.55, 127.79, 121.18, 120.83, 119.02, 109.41, 100.68, 69.94, 48.80, 46.42, 33.07, 31.75, 30.53, 29.73, 28.59, 27.28, 15.97. $[\alpha]_D^{20}$=+7.2° (c=0.23, CHCl$_3$). HPLC (OD-H, 10% IPA in hexanes, 1 mL/min, 220 nm) ee=98%: $t_R$ (major)=13.1 min, $t_R$ (minor)=14.6 min. HRMS (ESI) calculated for C$_{21}$H$_{33}$BNO$_2$ [M+H]$^+$ 341.2635, found 341.2634.

Compound 37l

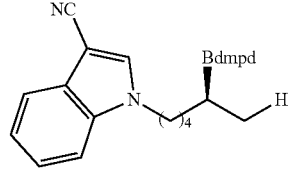

The regioselectivity of the crude product is (Markov:anti-Markov) 83:17, anhydrous oil, yield=53%; $^1$H NMR (400 MHz, CDCl$_3$) δ: 7.75 (d, J=7.7 Hz, 1H), 7.60 (s, 1H), 7.41 (d, J=8.1 Hz, 1H), 7.32 (t, J=7.1 Hz, 1H), 7.27 (t, J=7.3 Hz, 1H), 4.14 (t, J=7.1 Hz, 2H), 2.04-1.77 (m, 2H), 1.71 (s, 2H), 1.48-1.38 (m, 1H), 1.37-1.25 (m, 3H), 1.23 (d, J=3.6 Hz, 12H), 0.87 (d, J=7.0 Hz, 3H), 0.84-0.75 (m, 1H); $^{13}$C NMR (101 MHz, CDCl$_3$) δ: 135.31, 134.65, 127.93, 123.60, 121.94, 119.87, 116.05, 110.58, 85.26, 69.99, 48.73, 47.27, 32.90, 31.69, 31.68, 30.05, 26.10, 15.96. $[\alpha]_D^{20}$=+11.3° (c=0.54, CHCl$_3$). HPLC (OD-H, 10% IPA in hexanes, 1 mL/min, 220 nm) ee=94%: $t_R$ (major)=25.3 min, $t_R$ (minor)= 27.2 min. HRMS (ESI) calculated for C$_{22}$H$_{35}$O$_2$BN$_3$ [M+NH$_4$]$^+$ 383.2853, found 383.2853.

Compound 37m

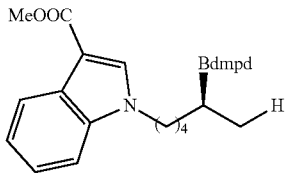

The regioselectivity of the crude product is (Markov:anti-Markov) 85:15, anhydrous oil, yield=67%; $^1$H NMR (400 MHz, CDCl$_3$) δ: 8.28-8.06 (m, 1H), 7.82 (s, 1H), 7.38-7.35 (m, 1H), 7.28-7.25 (m, 2H), 4.12 (t, J=7.1 Hz, 2H), 3.90 (s, 3H), 1.94-1.78 (m, 2H), 1.70 (s, 2H), 1.47-1.37 (m, 1H), 1.37-1.25 (m, 3H), 1.23 (d, J=4.1 Hz, 12H), 0.88 (d, J=6.9 Hz, 3H), 0.83-0.77 (m, 1H); $^{13}$C NMR (101 MHz, CDCl$_3$) δ: 165.51, 136.47, 134.25, 126.72, 122.52, 121.67, 121.64, 110.02, 106.60, 69.94, 50.87, 48.73, 47.06, 32.98, 31.67, 31.66, 30.10, 26.21, 15.94. $[\alpha]_D^{20}$=+15.1° (c=0.70, CHCl$_3$). HPLC (OJ-H, 10% IPA in hexanes, 1 mL/min, 254 nm) ee=97%: $t_R$ (minor)=22.4 min, $t_R$ (major)=24.0 min. HRMS (ESI) calculated for C$_{23}$H$_{35}$O$_4$BN [M+H]$^+$ 399.2690, found 399.2687.

Compound 37n

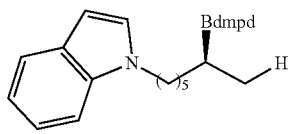

The regioselectivity of the crude product is (Markov:anti-Markov) 83:17, anhydrous oil, yield=71%; $^1$H NMR (400 MHz, CDCl$_3$) δ: 7.65 (d, J=7.8 Hz, 1H), 7.37 (d, J=8.2 Hz, 1H), 7.22 (t, J=7.6 Hz, 1H), 7.10 (d, J=8.3 Hz, 2H), 6.50 (s, 1H), 4.12 (t, J=7.1 Hz, 2H), 1.85 (s, 2H), 1.78 (s, 2H), 1.48-1.10 (m, 18H), 0.91 (d, J=6.9 Hz, 3H), 0.86-0.76 (m, 1H); $^{13}$C NMR (101 MHz, CDCl$_3$) δ: 135.94, 128.54, 127.79, 121.22, 120.88, 119.08, 109.40, 100.74, 69.93, 48.88, 46.41, 33.31, 31.82, 30.23, 29.73, 28.59, 27.28, 15.98. $[\alpha]_D^{20}$=+2.7° (c=0.26, CHCl$_3$). HPLC (SFC, OD, 15% IPA in CO$_2$, 1.3 mL/min, 214 nm) ee=90%: $t_R$ (major)=32.3 min, $t_R$ (minor)=33.4 min. HRMS (ESI) calculated for C$_{22}$H$_{35}$O$_2$BN [M+H]$^+$ 355.2792, found 355.2791.

Compound 37o

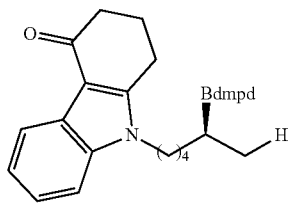

The regioselectivity of the crude product is (Markov:anti-Markov) 85:15, yellow oil, yield=43%; $^1$H NMR (400 MHz, CDCl$_3$) δ: 8.23 (dd, J=5.9, 3.0 Hz, 1H), 7.30-7.27 (m, 1H), 7.25-7.19 (m, 2H), 4.04 (t, J=7.4 Hz, 2H), 2.90 (t, J=6.1 Hz, 2H), 2.59-2.50 (m, 2H), 2.27-2.15 (m, 2H), 1.80-1.70 (m, 2H), 1.68 (s, 2H), 1.47-1.26 (m, 4H), 1.21 (d, 0.1=3.5 Hz, 12H), 0.86 (d, J=7.0 Hz, 3H), 0.81-0.75 (m, 1H); $^{13}$C NMR (101 MHz, CDCl$_3$) δ: 193.77, 151.46, 136.68, 124.89, 122.78, 122.33, 121.61, 112.52, 109.47, 69.97, 48.72, 43.86, 37.87, 33.01, 31.69, 31.67, 30.03, 26.35, 23.45, 22.33, 15.90. $[\alpha]_D^{20}$=+8.2° (c=0.57, CHCl$_3$). HPLC (OD-H, 10% IPA in hexanes, 1 mL/min, 220 nm) ee=97%: $t_R$ (major)=45.8 min, $t_R$ (minor)=53.7 min. HRMS (ESI) calculated for C$_{25}$H$_{37}$O$_3$BN [M+H]$^+$ 409.2897, found 409.2897.

Compound 37p

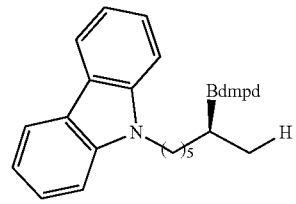

The regioselectivity of the crude product is (Markov:anti-Markov) 82:18, colorless oil, yield=60%; $^1$H NMR (400 MHz, CDCl$_3$) δ: 8.13 (d, J=7.7 Hz, 2H), 7.54-7.39 (m, 4H), 7.25 (t, J=7.3 Hz, 2H), 4.31 (t, J=7.3 Hz, 2H), 1.91-1.87 (m, 2H), 1.78 (s, 2H), δ 1.50-1.36 (m, 5H), 1.32 (s, 12H), 1.27-1.15 (m, 1H) 0.93 (d, J=7.0 Hz, 3H), 0.87-0.75 (m, 1H); $^{13}$C NMR (101 MHz, CDCl$_3$) δ: 140.44, 125.54, 122.80, 120.30, 118.63, 108.69, 69.93, 48.88, 43.10, 33.34, 31.82, 28.90, 28.75, 27.58, 16.02. $[\alpha]_D^{20}$=+3.7° (c=0.22, CHCl$_3$). HPLC (AD-H, 5% IPA in hexanes, 1 mL/min, 220 nm) ee=95%: $t_R$ (minor)=17.6 min, $t_R$ (major)=19.1 min. HRMS (ESI) calculated for C$_{26}$H$_{37}$O$_2$BN [M+H]$^+$ 405.2948, found 405.2942.

Compound 37q

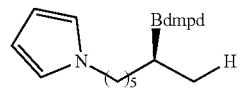

The regioselectivity of the crude product is (Markov:anti-Markov) 81:19, colorless oil, yield=44%; $^1$H NMR (400 MHz, CDCl$_3$) δ: 6.65 (s, 2H), 6.13 (s, 2H), 3.85 (t, J=7.3 Hz, 2H), 1.80-1.72 (m, 4H), 1.50-1.32 (m, 4H), 1.30 (s, 12H), 1.26-1.13 (m, 2H), 0.89 (d, J=7.0 Hz, 3H), 0.84-0.73 (m, 1H); $^{13}$C NMR (101 MHz, CDCl$_3$) δ: 120.43, 107.65, 69.91, 49.63, 48.87, 33.27, 31.80, 31.56, 28.52, 27.03, 15.93. $[\alpha]_D^{20}$=+4.9° (c=0.18, CHCl$_3$). HPLC (OJ-H, 5% IPA in hexanes, 1 mL/min, 220 nm) ee=95%: $t_R$ (major)=22.6 min, $t_R$ (minor)=28.6 min. HRMS (ESI) calculated for C$_{18}$H$_{33}$BNO$_2$ [M+H]$^+$ 305.2635, found 305.2633.

Compound 37r

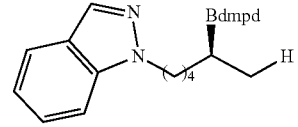

The regioselectivity of the crude product is (Markov:anti-Markov) 86:14, yellow oil, yield=62%; $^1$H NMR (400 MHz, CDCl$_3$) δ: 7.95 (s, 1H), 7.69 (d, J=8.0 Hz, 1H), 7.40 (d, J=8.5 Hz, 1H), 7.33 (t, J=7.6 Hz, 1H), 7.10 (t, J=7.4 Hz, 1H), 4.35 (t, J=7.1 Hz, 2H), 1.98-1.81 (m, 2H), 1.68 (s, 2H), 1.43 (d, J=8.0 Hz, 1H), 1.37-1.24 (m, 3H), 1.22 (s, 12H), 0.85 (d, J=7.0 Hz, 3H), 0.80-0.73 (m, 1H); $^{13}$C NMR (101 MHz, CDCl$_3$) δ: 132.48, 125.91, 120.98, 120.21, 109.08, 69.87, 49.04, 48.75, 33.07, 31.70, 30.23, 26.27, 15.89. [α]$_D^{20}$=+25.0° (c=0.60, CHCl$_3$). HPLC (IA, 5% IPA in hexanes, 1 mL/min, 220 nm) ee=86%: t$_R$ (major)=21.1 min, t$_R$ (minor)=22.4 min. HRMS (ESI) calculated for C$_{20}$H$_{32}$O$_2$BN$_2$ [M+H]$^+$ 342.2588, found 342.2584.0

Compound 37s

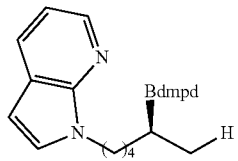

37s

The regioselectivity of the crude product is (Markov:anti-Markov) 85:15, colorless oil, yield=56%; $^1$H NMR (400 MHz, CDCl$_3$) δ: 8.29 (d, J=4.6 Hz, 1H), 7.86 (d, J=7.7 Hz, 1H), 7.20 (d, J=3.3 Hz, 1H), 7.00 (dd, J=7.5, 4.7 Hz, 1H), 6.40 (d, J=3.2 Hz, 1H), 4.26 (t, J=7.2 Hz, 2H), 1.94-1.77 (m, 2H), 1.69 (s, 2H), 1.49-1.36 (m, 1H), 1.35-1.25 (m, 3H), 1.22 (s, 12H), 0.85 (d, J=7.0 Hz, 3H), 0.81-0.71 (m, 1H); $^{13}$C NMR (101 MHz, CDCl$_3$) δ: 147.36, 142.51, 128.54, 127.98, 120.55, 115.34, 99.01, 69.88, 48.77, 44.60, 33.10, 31.71, 31.70, 30.70, 26.26, 15.93. [α]$_D^{20}$=+6.8° (c=0.56, CHCl$_3$). HPLC (OD-H, 10% IPA in hexanes, 1 mL/min, 220 nm) ee=91%: t$_R$ (major)=9.7 min, t$_R$ (minor)=10.5 min. HRMS (ESI), calculated for C$_{20}$H$_{32}$O$_2$BN$_2$ [M+H]$^+$ 342.2588, found 342.2582.

Compound 37t

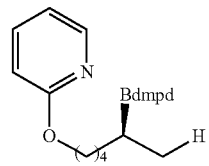

37t

The regioselectivity of the crude product is (Markov:anti-Markov) 83:17, colorless oil, yield=53%; $^1$H NMR (400 MHz, CDCl$_3$) δ: 8.13 (d, J=4.3 Hz, 1H), 7.52 (t, J=7.6 Hz, 1H), 6.85-6.77 (m, 1H), 6.69 (d, J=8.3 Hz, 1H), 4.25 (t, J=6.7 Hz, 2H), 1.79-1.71 (m, 4H), 1.48-1.39 (m, 3H), 1.35-1.30 (m, 1H), 1.29 (s, 12H), 0.89 (d, J=6.5 Hz, 3H), 0.86-0.77 (m, 1H); $^{13}$C NMR (101 MHz, CDCl$_3$) δ: 164.09, 146.82, 138.37, 116.31, 111.06, 69.90, 66.12, 48.83, 33.23, 31.76, 31.55, 29.40, 25.43, 15.91. [α]$_D^{20}$=+6.7° (c=0.42, CHCl$_3$). HPLC (OD-H, 5% IPA in hexanes, 1 mL/min, 254 nm) ee=90%: t$_R$ (minor)=10.0 min, t$_R$ (major)=11.0 min. HRMS (ESI) calculated for C$_{18}$H$_{31}$O$_3$BN [M+H]$^+$ 319.2428, found 319.2423.

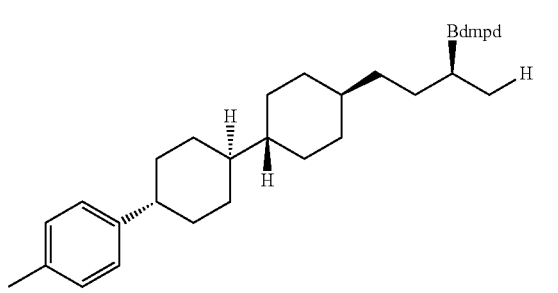

37u

Compound 37u

The regioselectivity of the crude product is (Markov:anti-Markov) 90:10, white power, melting point: 85-86° C., yield=62%, $^1$H NMR (400 MHz, CDCl$_3$) δ: 7.11 (s, 4H), 2.45-2.39 (m, 1H), 2.32 (s, 3H), 2.01-1.67 (m, 10H), 1.52-1.36 (m, 3H), 1.32 (s, 12H), 1.28-0.94 (m, 10H), 0.94-0.68 (m, 6H); $^{13}$C NMR (101 MHz, CDCl$_3$) δ: 144.95, 135.11, 128.93, 126.67, 69.85, 48.89, 44.26, 43.48, 42.97, 38.28, 37.00, 34.74, 33.79, 33.71, 31.83, 30.97, 30.42, 30.17, 20.99, 16.07. [α]$_D^{20}$=+6.3° (c=0.21, CHCl$_3$). HPLC (OJ-H, 1% IPA in hexanes, 1 mL/min, 220 nm) ee=96%: t$_R$(minor)=16.2 min, t$_R$ (major)=18.6 min.

Compound 37v

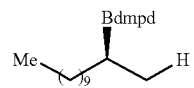

37v

The regioselectivity of the crude product is (Markov:anti-Markov) 82:18, colorless oil, yield=50%; $^1$H NMR (400 MHz, CDCl$_3$) δ: 1.76 (s, 2H), 1.42-1.33 (m, 2H), 1.30 (s, 12H), 1.27-1.12 (m, 16H), 0.87 (t, J=6.2 Hz, 6H), 0.83-0.70 (m, 1H); $^{13}$C NMR (101 MHz, CDCl$_3$) δ: 69.81, 48.88, 33.56, 31.91, 31.77, 29.98, 29.69, 29.67, 29.64, 29.35, 29.04, 22.67, 15.94, 14.08. [α]$_D^{20}$=+4.9° (c=0.41, CHCl$_3$). The compound is oxidized into alcohol, and reacted with benzoyl chloride to determine the enantioselectivity, HPLC (OD-H, 0.1% IPA in hexanes, 1 mL/min, 220 nm) ee=91% t$_R$ (minor)=7.2 min, t$_R$ (major)=8.0 min. HRMS (EI) calculated for C$_{19}$H$_{39}$O$_2$B [M]$^+$09.3079, found 309.3073.

Compound 37w

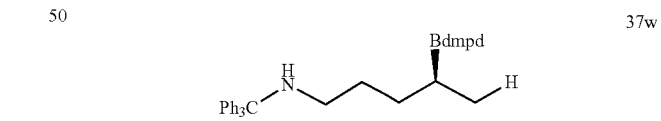

37w

The regioselectivity of the crude product is (Markov:anti-Markov) 90:10, colorless oil, yield=78%; $^1$H NMR (400 MHz, CDCl$_3$) δ: 7.50 (d, J=7.9 Hz, 6H), 7.28 (t, J=7.6 Hz, 6H), 7.18 (t, J=7.2 Hz, 3H), 2.13-2.12 (m, 2H), 1.78 (s, 2H), 1.58-1.37 (m, 4H), 1.32 (s, 12H), 1.27-1.11 (m, 1H), 0.90 (d, J=7.2 Hz, 3H), 0.84-0.74 (m, 1H); $^{13}$C NMR (101 MHz, CDCl$_3$) δ: 146.49, 128.71, 127.67, 126.06, 70.86, 69.92, 48.88, 44.02, 31.82, 31.12, 30.40, 15.87. [α]$_D^{20}$=+0.9° (c=0.22, CHCl$_3$). HPLC (OD-H, 5% IPA in hexanes, 1 mL/min, 220 nm) ee=95%: t$_R$(minor)=7.4 min, t$_R$ (major)=8.5 min. HRMS (ESI) calculated for C$_{31}$H$_{41}$O$_2$BN [M+H]$^+$ 469.3261, found 469.3259.

Compound 37x

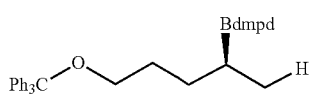

The regioselectivity of the crude product is (Markov:anti-Markov) 88:12, colorless oil, yield=67%; $^1$H NMR (400 MHz, CDCl$_3$) δ: 7.47 (d, J=8.1 Hz, 6H), 7.29 (t, J=7.6 Hz, 6H), 7.26-7.21 (m, 3H), 3.04 (t, J=6.8 Hz, 2H), 1.78 (s, 2H), 1.67-1.64 in, 2H), 1.56-1.45 in, 1H), 1.31 (s, 12H), 1.29-1.16 (m, 1H), 0.91 (d, 0.1=7.2 Hz, 3H), 0.86-0.78 (m, 1H); $^{13}$C NMR (101 MHz, CDCl$_3$) δ: 144.67, 128.73, 127.63, 126.70, 86.19, 69.92, 64.32, 48.87, 31.82, 29.94, 29.53, 15.87. $[α]_D^{20}$=+2.1° (c=0.28, CHCl$_3$). HPLC (OD-H, 5% IPA in hexanes, 1 mL/min, 220 nm) ee=91%: $t_R$(minor)=7.5 min, $t_R$ (major)=10.0 min.

Compound 37y

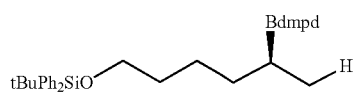

The regioselectivity of the crude product is (Markov:anti-Markov) 82:18, colorless oil, yield=50%; $^1$H NMR (400 MHz, CDCl$_3$) δ: 7.67 (d, 0.1=6.8 Hz, 4H), 7.47-7.29 (m, 6H), 3.64 (t, 0.1=6.6 Hz, 2H), 1.75 (s, 2H), 1.61-1.53 (m, 2H), 1.51-1.39 (m, 1H), 1.28 (s, 12H), 1.22-1.17 (m, 1H), 1.04 (s, 9H), 0.88 (d, J=7.0 Hz, 3H), 0.84-0.70 (m, 1H); $^{13}$C NMR (101 MHz, CDCl$_3$) δ: 135.55, 134.32, 129.35, 127.49, 69.87, 64.58, 48.83, 32.08, 31.77, 29.52, 26.87, 19.23, 15.87. $[α]_D^{20}$=+3.7° (c=0.74, CHCl$_3$). HPLC (OD-H, 1% IPA in hexanes, 1 mL/min, 220 nm) ee=90%: $t_R$ (minor)= 12.7 min, $t_R$ (major)=14.8 min. HRMS (ESI) calculated for C$_{28}$H$_{44}$O$_3$BSi [M+H]$^+$ 466.3184, found 466.3183.

Compound 37z

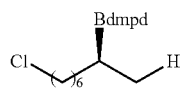

The regioselectivity of the crude product is (Markov:anti-Markov) 85:15, colorless oil, yield=45%; $^1$H NMR (400 MHz, CDCl$_3$) δ: 3.52 (t, J=6.8 Hz, 2H), 1.82-1.70 (m, 4H), 1.47-1.36 (m, 3H), 1.34-1.11 (m, 17H), 0.88 (d, J=7.0 Hz, 3H), 0.81-0.78 (m, 1H); $^{13}$C NMR (101 MHz, CDCl$_3$) δ: 69.89, 48.85, 45.24, 33.35, 32.66, 31.78, 29.16, 28.80, 26.89, 15.95. $[α]_D^{20}$=+6.5° (c=0.24, CHCl$_3$). The compound is oxidized into alcohol, and reacted with benzoyl chloride to determine the enantioselectivity, HPLC (AD-H, 1% IPA in hexanes, 0.5 mL/min, 220 nm) ee=91%: $t_R$(minor)=10.5 min, $t_R$ (major)=12.6 min. HRMS (EI) calculated for C$_{15}$H$_{30}$O$_2$BCl [M]$^+$287.2064, found 287.2071.

Compound 37aa

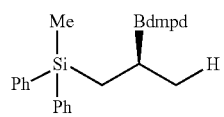

The regioselectivity of the crude product is (Markov:anti-Markov) 94:4, colorless oil, yield=83%; $^1$H NMR (400 MHz, CDCl$_3$) δ: 7.56 (d, J=5.2 Hz, 4H), 7.35 (s, 6H), 1.66 (s, 2H), 1.45 (dd, J=14.7, 8.9 Hz, 1H), 1.25 (s, 12H), 1.09-1.04 (m, 1H), 1.00 (d, J=6.8 Hz, 3H), 0.94 (dd, J=14.6, 4.5 Hz, 1H), 0.58 (s, 3H); $^{13}$C NMR (101 MHz, CDCl$_3$) δ: 138.45, 138.43, 134.67, 134.60, 128.76, 127.62, 69.91, 48.55, 31.68, 31.62, 20.74, 17.39. $[α]_D^{20}$=+13.1° (c=0.35, CHCl$_3$). HPLC (OD-H, 5% IPA in hexanes, 1 mL/min, 220 nm) ee=96%: $t_R$ (minor)=9.8 min, $t_R$ (major)=13.9 min. HRMS (ESI) calculated for C$_{23}$H$_{37}$O$_2$BNSi [M+NH$_4$]$^+$ 397.2717, found 397.2713.

Compound 37bb

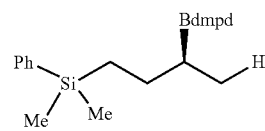

The regioselectivity of the crude product is (Markov:anti-Markov) 87:13, colorless oil, yield=80%; $^1$H NMR (400 MHz, CDCl$_3$) δ: 7.54-7.53 (m, 2H), 7.35-7.34 (m, 3H), 1.78 (s, 2H), 1.47-1.43 (m, 1H), 1.31 (s, 12H), 1.28-1.12 (m, 1H), 0.91-0.83 (m, 4H), 0.78-0.74 (m, 2H), 0.26 (s, 6H); $^{13}$C NMR (101 MHz, CDCl$_3$) δ: 140.11, 133.59, 128.56, 127.59, 69.89, 48.90, 31.83, 27.51, 15.74, 14.89. $[α]_D^{20}$=+6.2° (c=0.26, CHCl$_3$). HPLC (OD-H, 5% IPA in hexanes, 1 mL/min, 220 nm) ee=94%: $t_R$ (major)=6.4 min, $t_R$(minor)= 7.5 min. HRMS (ESI) calculated for C$_{19}$H$_{37}$BNO$_2$Si [M+NH$_4$]$^+$ 349.2717, found 349.2711.

Although the specific embodiments of this present invention are described above, those skilled in the art should understand that these are merely examples, and without departing from the principle and essence of the invention, various changes or modifications can be made to these embodiments. Therefore, the scope of protection of this present invention is defined by the appended claims.

What we claim is:

1. A chiral 1, 3-diaryl imidazole carbene precursor as shown in formula S:

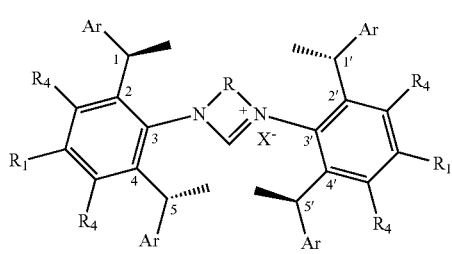

wherein

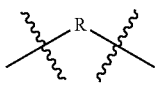

is selected from the group consisting of

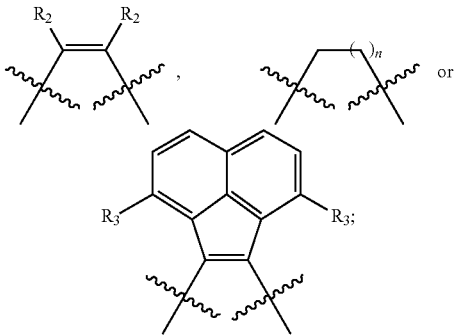

each $R^1$ is independently selected from the group consisting of substituted or unsubstituted $C_{1-4}$ alkyl, substituted or unsubstituted $C_{3-6}$ cycloalkyl, and substituted or unsubstituted $C_{1-4}$ alkoxy; wherein the substituent of substituted $C_{1-4}$ alkyl, substituted $C_{3-6}$ cycloalkyl and substituted $C_{1-4}$ alkoxy is one or more selected from the group consisting of halogen, cyano, nitro, carbonyl, $C_{1-4}$ alkyl, halogen-substituted $C_{1-4}$ alkyl, hydroxy-substituted $C_{1-4}$ alkyl, $C_{1-4}$ alkoxy, $C_{3-6}$ cycloalkyl, $C_{2-6}$ heterocyclic, $C_{6-14}$ aryl, $C_{2-10}$ heteroaryl, carboxyl and

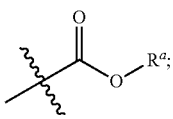

when there are multiple substituents, each substituent is the same or different; $R^a$ is $C_{1-4}$ alkyl; the term "$C_{2-6}$ heterocyclic" as used herein means $C_{2-6}$ heterocyclic comprising 1-4 heteroatoms selected from the group consisting of N, O and S; the term "$C_{2-10}$ heteroaryl" as used herein means $C_{2-10}$ heteroaryl comprising 1-4 heteroatoms selected from the group consisting of N, O and S;

each $R^2$ is independently selected from the group consisting of $C_{1-4}$ alkyl, halo,

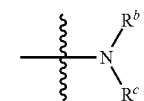

and $C_{6-14}$ aryl, wherein $R^b$ and $R^c$ are independently $C_{1-4}$ alkyl;
each $R^3$ is independently H or $C_{1-4}$ alkyl;
each $R^4$ is independently H or $C_{1-4}$ alkyl;
each Ar is independently $C_{6-14}$ aryl or $C_{2-10}$ heteroaryl;
or each Ar is further substituted by one or more substituents selected from the group consisting of halo, cyano, nitro, carbonyl, $C_{1-4}$ alkyl, halogen-substituted $C_{1-4}$ alkyl, hydroxy-substituted $C_{1-4}$ alkyl, $C_{1-4}$ alkoxy, $C_{3-6}$ cycloalkyl, $C_{2-6}$ heterocyclic, $C_{6-14}$ aryl, $C_{2-10}$ heteroaryl, carboxyl and

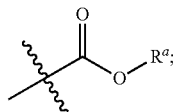

wherein when there are multiple substituents, each substituent is the same or different; $R^a$ is $C_{1-4}$ alkyl; the term "$C_{2-6}$ heterocyclic" as used herein means $C_{2-6}$ heterocyclic comprising 1-4 heteroatoms selected from the group consisting of N, O and S; the term "$C_{2-10}$ heteroaryl" as used herein means $C_{2-10}$ heteroaryl comprising 1-4 heteroatoms selected from the group consisting of N, O and S;
the term "$C_{2-10}$ heteroaryl" as used in Ar means $C_{2-10}$ heteroaryl comprising 1-4 heteroatoms selected from the group consisting of N, O and S;
n is 1, 2 or 3;
X is Cl⁻, Br⁻, I⁻, OTf⁻ or BF₄⁻.

2. The chiral 1, 3-diaryl imidazole carbene precursor as shown in formula S according to claim 1, wherein,
each Ar is independently selected from $C_{6-14}$ aryl;
and/or, each Ar is further substituted by one or more from $C_{1-4}$ alkyl or $C_{1-4}$ alkoxy
and/or each $R^1$ is independently $C_{1-4}$ alkyl or $C_{1-4}$ alkoxy;
and/or each $R^2$ is independently $C_{1-4}$ alkyl;
and/or each $R^4$ is independently H or methyl;
and/or n is 1 or 2;
and/or X is Cl⁻, Br⁻, I⁻or BF₄⁻;
and/or each $R^1$ is the same, each $R^2$ is the same, each $R^3$ is the same, and/or each Ar is the same;
and/or in each $R^1$, when the substituent in substituted $C_{1-4}$ alkyl, substituted $C_{3-6}$ cycloalkyl and substituted $C_{1-4}$alkoxy are each independently $C_{2-10}$heteroaryl, the term "$C_{2-10}$heteroaryl" as used herein refers to $C_{3-10}$ heteroaryl group containing 1-4 heteroatoms selected from the group consisting of N, O and S;
and/or each in $R^1$, when the substituent in substituted $C_{1-4}$ alkyl, substituted $C_{3-6}$ cycloalkyl and substituted $C_{1-4}$ alkoxy are each independently $C_{2-6}$heterocyclic, the term "$C_{2-6}$heterocyclic" refers to $C_{3-10}$ heteroaryl group containing 1-4 heteroatoms selected from the group consisting of N, O and S;
and/or in each Ar, the term "$C_{2-10}$heteroaryl" as used refers to $C_{5-10}$heteroaryl group containing 1-4 heteroatoms selected from the group consisting of N, O and S.

3. The chiral 1, 3-diaryl imidazole carbene precursor as shown in formula S according to claim 1,
wherein each Ar is independently $C_{6-14}$ aryl;
each $R^1$ is independently selected from the group consisting of $C_{1-4}$ alkyl or $C_{1-4}$ alkoxy
each $R^2$ is independently $C_{1-4}$ alkyl;
each $R^3$ is independently selected from the group consisting of H and $C_{1-4}$ alkyl;
each $R^4$ is independently selected from the group consisting of H and $C_{1-4}$ alkyl
n is 1 or 2; and/or
X is Cl⁻ or Br⁻;
or Ar is independently $C_{6-14}$ aryl;
each $R^1$ is independently selected from the group consisting of $C_{1-4}$ alkyl and $C_{1-4}$ alkoxy each $R^2$ is independently $C_{1-4}$ alkyl;

each $R^3$ is independently selected from the group consisting of $C_{1-4}$ alkyl;

each $R^4$ is independently selected from the group consisting of H and $C_{1-4}$ alkyl;

n is 1 or 2, and/or

X is Cl⁻ or Br⁻;

or

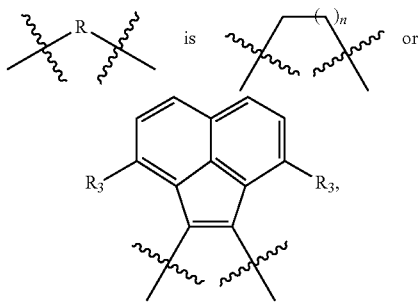

is each Ar is independently selected from $C_{6-14}$ aryl and the Ar is further optionally substituted by one or more of $C_{1-4}$ alkyl or $C_{1-4}$ alkoxy;

each $R^1$ is independently selected from the group consisting of $C_{1-4}$ alkyl and $C_{1-4}$ alkoxy;

each $R^3$ is independently selected from the group consisting of $C_{1-4}$ alkyl;

each $R^4$ is independently selected from the group consisting of H and $C_{1-4}$ alkyl;

n is 1 or 2, and/or

X is Cl⁻ or Br⁻;

or

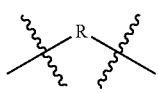

is

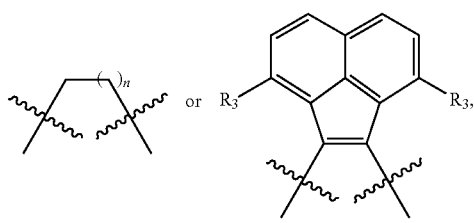

each Ar is independently $C_{6-14}$ aryl; and the Ar is further optionally substituted by one or more selected from $C_{1-4}$ alkyl and $C_{1-4}$ alkoxy;

each $R^1$ is independently $C_{1-4}$ alkyl;

each $R^3$ is independently $C_{1-4}$ alkyl;

each $R^4$ is independently selected from the group consisting of H;

n is 1, and/or

X⁻ is Cl⁻;

or,

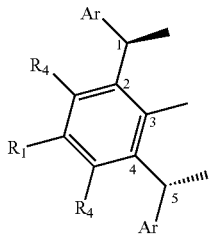

is selected from the group consisting of

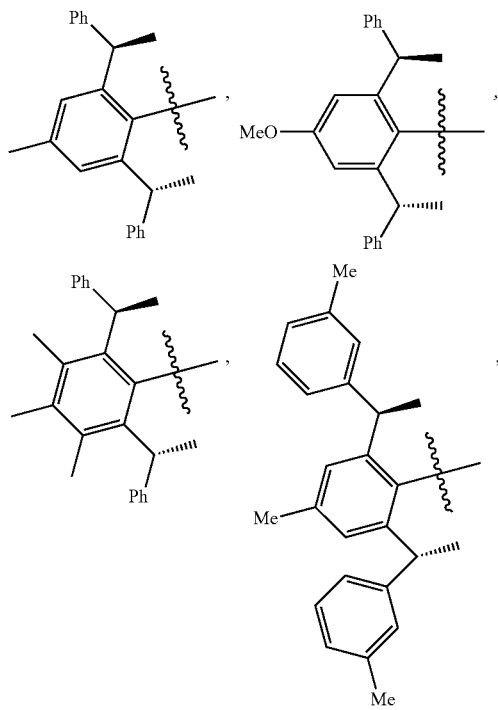

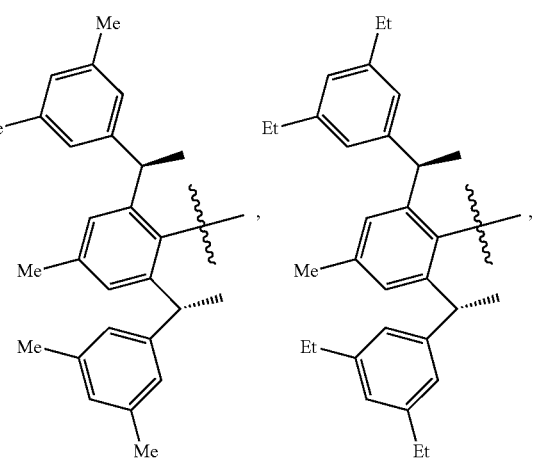

-continued
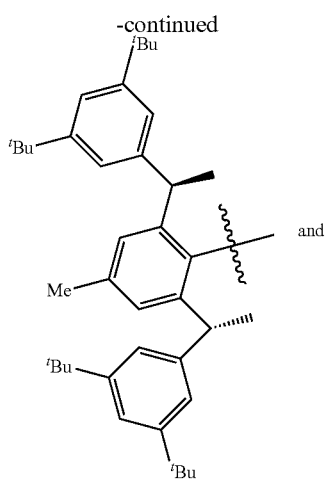
and
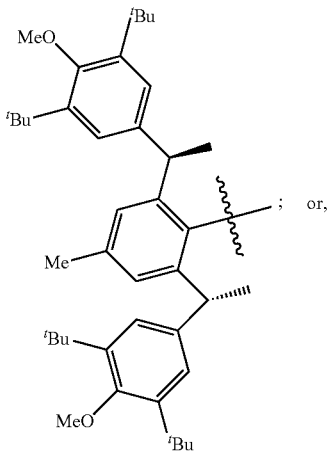
; or,
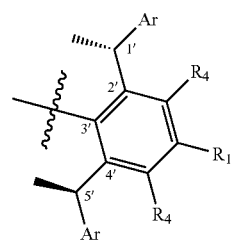
is selected from the group consisting of
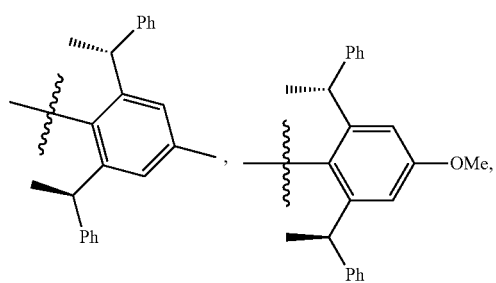
-continued
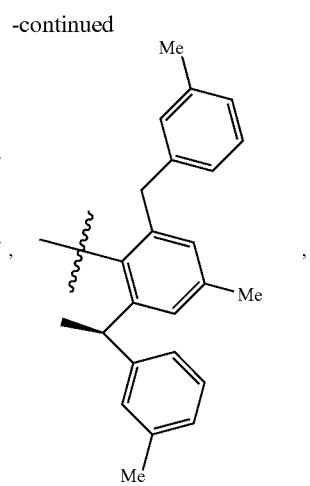
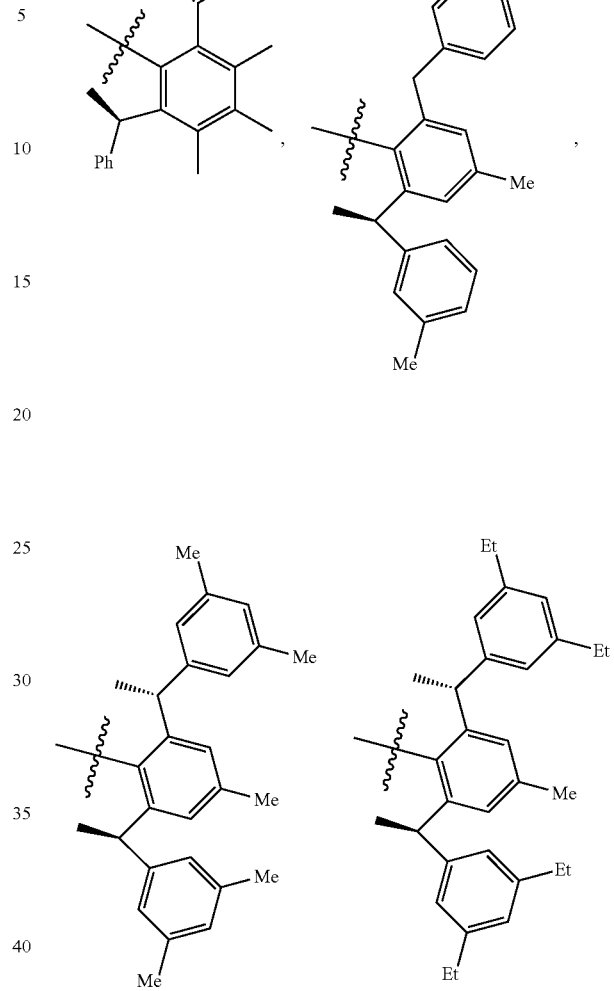

4. The chiral 1, 3-diaryl imidazole carbene precursor as shown in formula S according to claim 1, which is selected from the group consisting of:
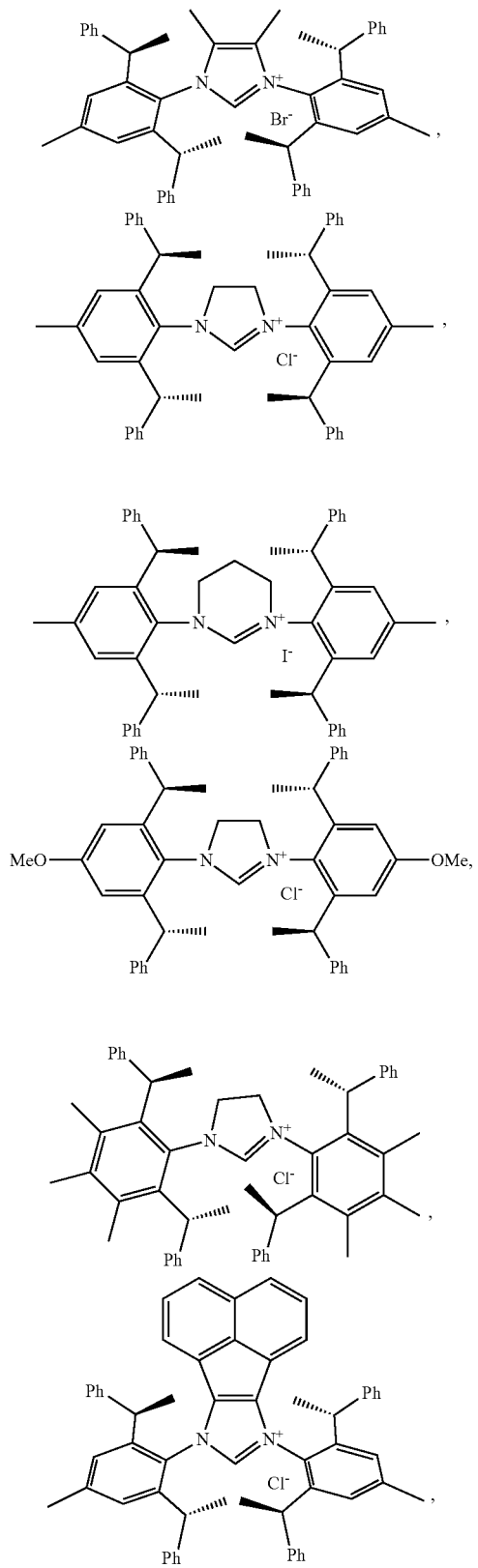
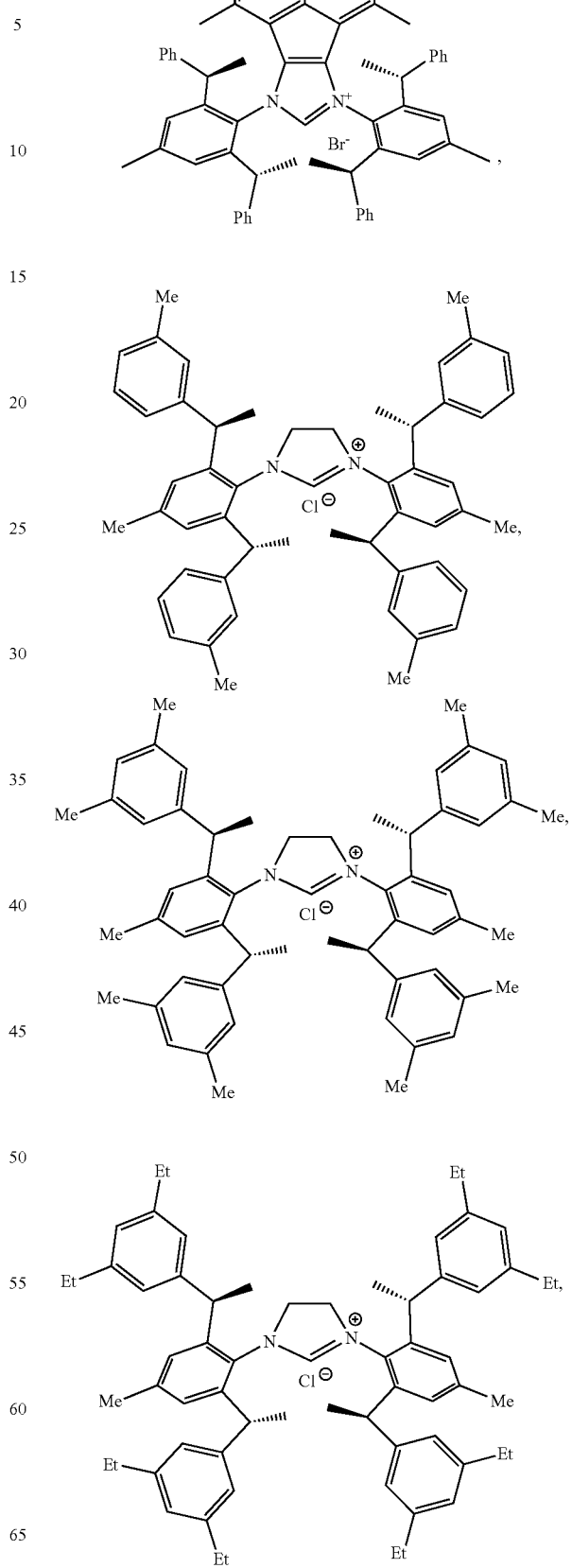

-continued
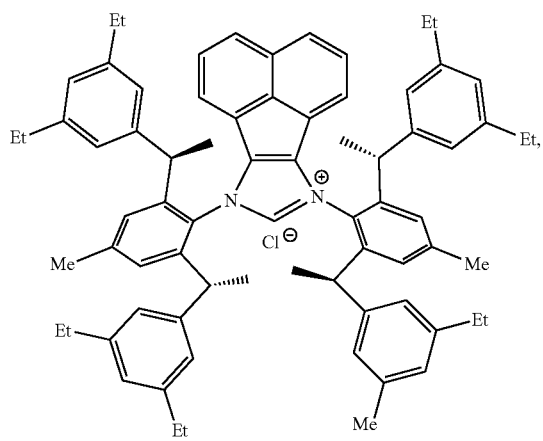
and
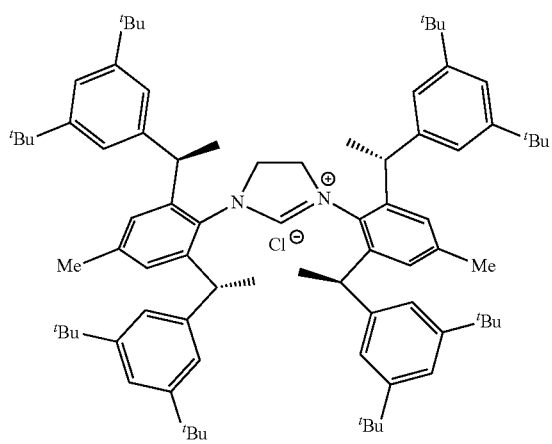
5. A method of preparation of the chiral 1, 3-diaryl imidazole carbene precursor as shown in formula S according to claim 1, which comprises any of the following:
when R is
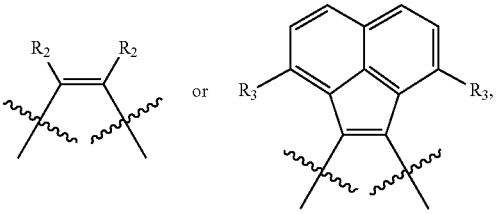
the formula S precursor is prepared by method a), which comprises reacting compounds of formula S' with halomethyl alkyl ether as follows;
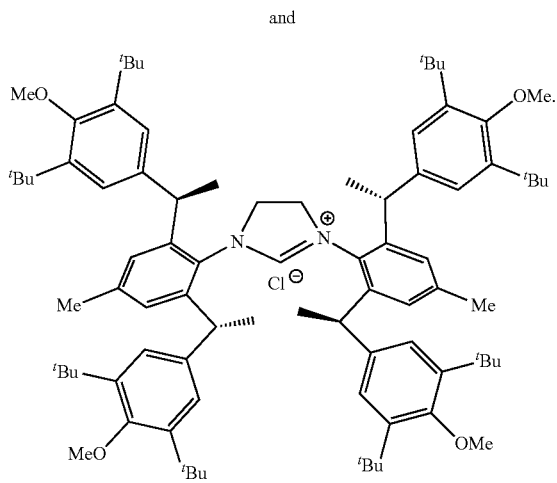
wherein
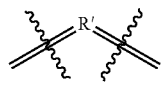
is
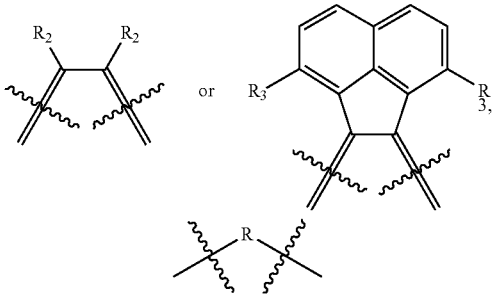

is

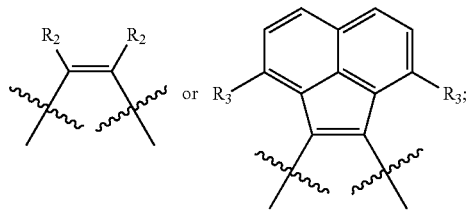

$R_1$, $R_2$, $R_3$, $R_4$, Ar, n and $X^-$ are as defined in claim 1;
or when

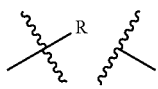

is

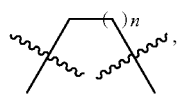

the formula S precursor is prepared by method b) which comprises the following steps: in a solvent, reacting compounds of formula M6 with S2 in the presence of base:

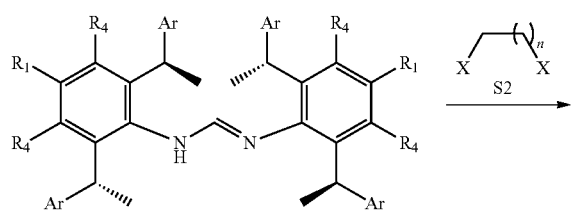

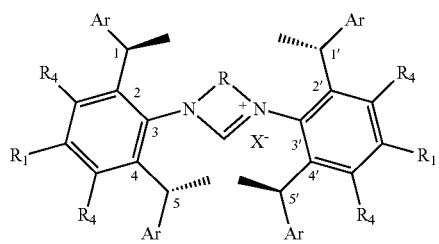

wherein

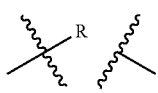

is selected from the

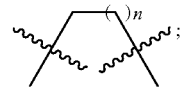

$R_1$, $R_4$, Ar, $X^-$ and n are the same ones according to claim 1. X means halogen consisting of Cl, Br and I;
or when

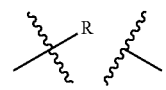

is

the formula S precursor is prepared by method c) which comprises the following steps: reacting compound of formula M8 with triethyl orthoformate with the presence of $NH_4X$ as follows:

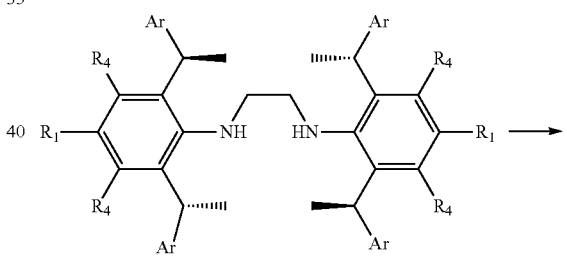

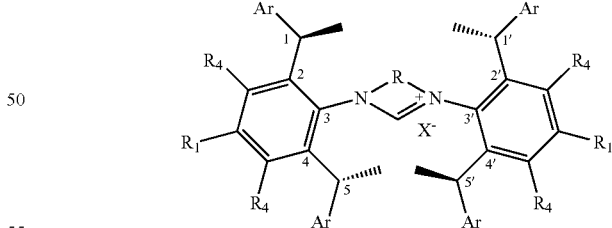

wherein

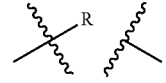

is

$R_1$, $R_4$, Ar and $X^-$ are as defined in claim 1.

6. The method according to claim 5, wherein
in method a), the reaction is conducted under solvent-free condition;
and/or in method a), the halomethyl alkyl ether is chloromethyl ether and/or bromomethyl ether.
and/or in method a), the molar ratio between the compound S' to halomethyl alkyl ether is 1:5 to 1:30;
and/or in method a), the temperature used herein is 80° C. to 130° C.;
and/or in method b), the solvent used herein is one or more selected from the group consisting of nitrile solvents, halogenated hydrocarbon solvents, amide solvents and ether solvents;
and/or in method b), the base used herein is an organic base and/or inorganic base; ;
and/or in method b), the molar ratio of base to the compound M6 is 0.9 to 1.5;
and/or in method b), the molar ratio of the compound S2 to the compound M6 is 1.2 to 5;
and/or in method b), the temperature used herein is 50° C. to 100° C.;
and/or in method c), the formula $NH_4X$ used herein is $NH_4Cl$ or $NH_4Br$;
and/or in method c), the molar ratio of $NH_4X$ to the compound M8 is 1.2 to 3;
and/or in method c), the volume molar ratio of triethyl orthoformate to the compound M8 is 3 to 15 L/mol;
and/or in method c), the temperature used herein is 90° C. to 130° C.

7. The chiral 1, 3-diaryl imidazole carbene precursor as shown in formula S according to claim 1, wherein the carbine precursor is prepared from a compound of formula M6 or M8:

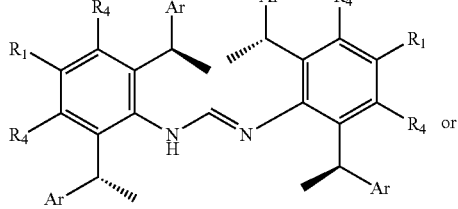

M6 or

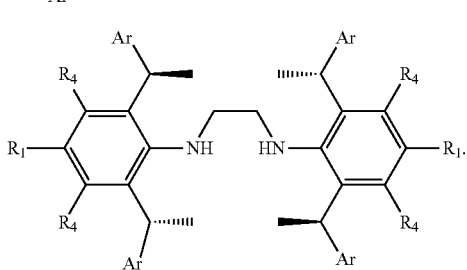

M8

8. The chiral 1, 3-diaryl imidazole carbene precursor as shown in formula S according to claim 1, wherein the copper (I) complex of 1, 3-diaryl imidazole salt carbene precursor is:

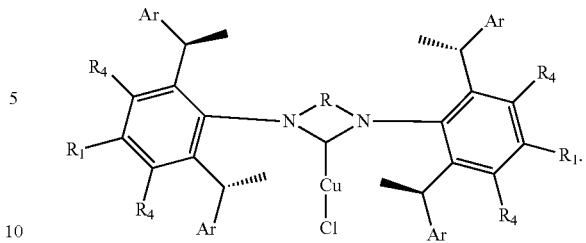

9. The chiral 1, 3-diaryl imidazole carbene precursor as shown in formula S according to claim 8, wherein the complex is compound 35:

35

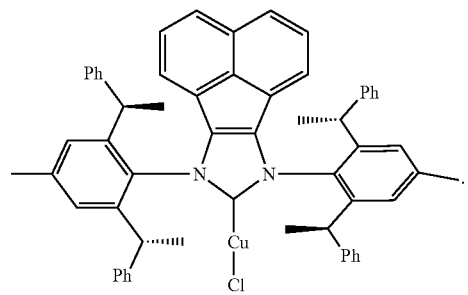

10. The method of preparation of the complex according to claim 8, which comprises the step:

in the organic solvent, reacting the chiral 1, 3-diarylimidazole carbene precursor as shown in formula S with the monovalent copper salt in the presence of a base as follows:

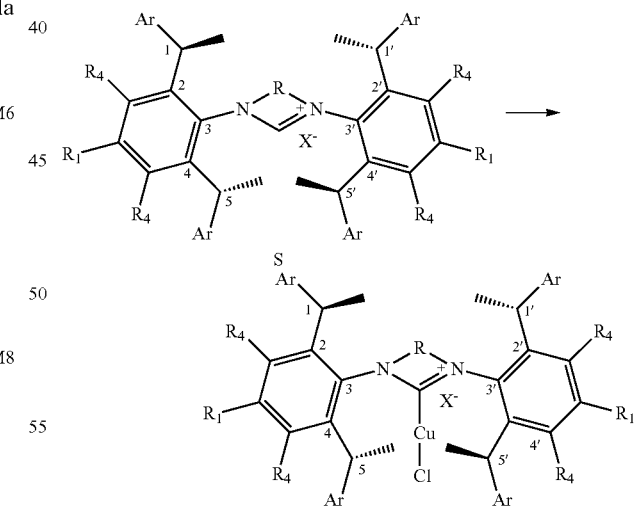

wherein $R_1$, $R_2$, $R_3$, $R_4$, Ar, n and $X^-$ are as defined in claim 8.

11. The method of claim 10,
wherein the organic solvent used herein is one or more low-polarity non-proton solvent selected from the group consisting of alkane solvent, arene solvent and ether solvent;

the base is alkali metal tert-butoxide salts,
and/or the molar ratio of base to the 1, 3-diaryl imidazole salt carbene precursor compound represented by the formula S is 1.0 to 1.2;
and/or the monovalent copper salt used herein is copper halide;
and/or the molar ratio of monovalent copper salt to the compound represented by the formula S used herein is 0.9 to 1.2;
and/or the reaction temperature is room temperature.

12. A crystal form of compound 35, wherein when determined by single-crystal X-ray diffraction spectrum using Cu-Kα radiation, the crystal belongs to a hexagonal system, the space group was P6$_5$, and the final unit cell parameters are: a=13.6295(3)Å, α=90°, b=13.6295(3)Å, β=90°, c=50.1903(16)Å, γ=120°; the volume of the unit cell (V) is 8074.4(4) Å3, and the number of asymmetry units in the unit cell (Z) is 6;

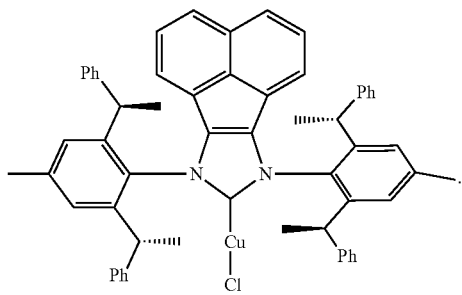

13. The method of synthesizing the crystal form of compound 35 according to claim 12, comprising the following steps:
mixing the compound 35 with an ether solvent before filtered, and then the filtrate is placed under an atmosphere of alkane solvent;
the methods of synthesizing the crystallography of compound 35 comprises the following steps: a solution of compound 35 mixed with an ether solvent is filtered after sonication, and then the filtrate is placed under an atmosphere of alkane solvent; the volume mass ratio of ether solvents to the compound of 35 used herein is 0.1~0.5 L/g; the alkane solvent is selected from n-pentane and/or n-hexane.

14. The copper (I) complex of 1, 3-diaryl imidazole salt carbene precursor according to claim 8, wherein the copper (I) complex of 1.3-diaryl imidazole salt carnene precursor is used in asymmetric catalytic reaction, wherein the asymmetric catalytic reaction is of asymmetric hydroboration of non-activated terminal olefins.

15. The copper (I) complex of 1, 3-diaryl imidazole salt carbene precursor according to claim 14, wherein,
the asymmetric hydroboration of non-activated terminal olefins comprises:
in organic solvent, with the presence of Cu (I)/chiral 1, 3-diarylimidazole carbene precursor, complex-catalyzed the asymmetric hydroboration of non-activated terminal olefins using diboron reagent with the presence of a base.

16. The copper (I) complex of 1, 3-diaryl imidazole salt carbene precursor according to claim 15, wherein
in step a), the organic solvent is one or more low-polarity non-proton solvent selected from the group consisting of alkane solvent, arene solvent, and ether solvent; the alkane solvent is haloalkane solvent and/or unsubstituted alkane solvent;
and/or in step a), the base is alkali metal tert-butoxide salt;
and/or in step a), the molar ratio of base to the non-activated terminal olefins is 1.2 to 2;
and/or in step a), the molar ratio of copper/chiral 1, 3-diarylimidazole carbene precursor complex (I) to the non-activated terminal olefin used herein is 0.01 to 0.05;
and/or in step a), the diboron reagent is

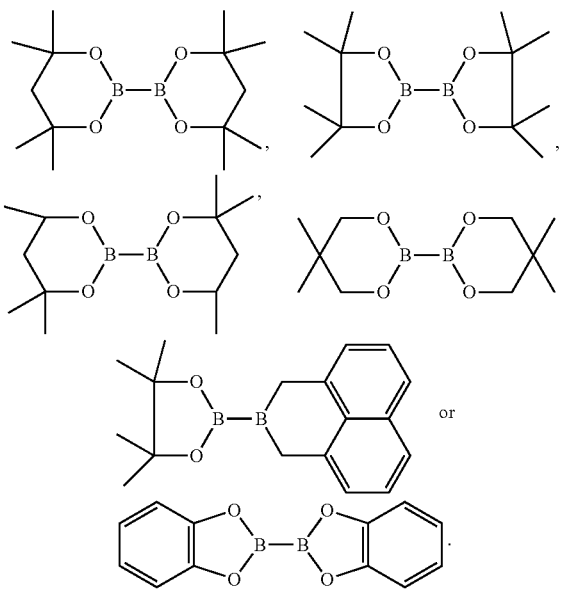

and/or in step a), the molar ratio of diboron to the non-activated terminal olefin is 1.5 to 3;
and/or in step a), the reaction temperature is room temperature,
and/or in step b), the proton source is one or more alcohol, selected from the group consisting of methanol, ethanol, and isopropanol;
and/or in step b), the molar ratio of proton source to the non-activated terminal olefin used herein is 1.5 to 3;
and/or wherein step b), the reaction temperature is room temperature;
and/or wherein step b), the non-activated terminal olefin used herein is of the following structure:

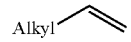

wherein Alkyl represents substituted or unsubstituted $C_{1-10}$ alkyl, and the substituent of the $C_{1-10}$ alkyl is one or more selected from the group consisting of halogen, $C_{6-14}$ aryl, substituted $C_{6-14}$ aryl, $C_{1-10}$alkoxy, substituted $C_{1-10}$ alkoxy, —OR$^{p1}$, —Si(R$^{p5}$)$_3$, —NHC(R$^{p6}$)$_3$, $C_{2-12}$ heteroaryl, substituted $C_{2-12}$ heteroaryl, $C_{3-6}$ cycloalkyl or substituted $C_{3-6}$ cycloalkyl, wherein R$^{p1}$ is selected from the group consisting of $C_{6-14}$ aryl, substituted $C_{6-14}$ aryl, $C_{2-12}$ heteroaryl, substituted $C_{2-12}$ heteroaryl or —SiR$^{p4}$; wherein R$^{p4}$ is $C_{6-14}$ aryl or substituted $C_{6-14}$ aryl; each R$^{p5}$ and R$^{p6}$ are independently $C_{1-4}$ alkyl or $C_{6-14}$ aryl;

the substituent of the $C_{6-14}$ aryl, $C_{1-10}$ alkoxy, $C_{2-12}$heteroaryl and $C_{3-6}$ cycloalkyl is independently one or more selected from the group consisting of halo, cyano, nitro, —COOR$^{p2}$, —C(O)—, $C_{3-6}$ cycloalkyl, substituted $C_{3-6}$ cycloalkyl, $C_{6-14}$ aryl, substituted $C_{6-14}$ aryl and $C_{2-12}$ heteroaryl; R$^{p2}$ is selected from H or $C_{1-4}$alkyl; in said substituent, the substituent of $C_{6-14}$ aryl is one or more selected from the group consisting of halo, —SR$^{p3}$, $C_{1-4}$ alkyl, halogen-substituted $C_{1-4}$ alkyl, $C_{1-4}$ alkoxy, and halogen-substituted $C_{1-4}$ alkoxy; R$^{p3}$ is selected from H or $C_{1-4}$ alkyl; or two adjacent substituents in the substituted $C_{6-14}$ aryl together form a $C_{2-6}$ heterocyclyl based on the carbons to which they are attached; the hetero atom in $C_{2-6}$ heterocyclyl is 1-4 heteroatoms selected from the group consisting of N, O, and S; the substituent of substituted $C_{3-6}$ cycloalkyl is one or more selected from the group consisting of $C_{6-14}$ aryl or $C_{1-4}$alkyl-substituted $C_{2-12}$heteroaryl;

the $C_{2-12}$heteroaryl is a $C_{2-12}$heteroaryl group comprising 1-4 heteroatoms selected from the group consisting of N, O, and S.

\* \* \* \* \*